(12) United States Patent
Mendez et al.

(10) Patent No.: US 8,314,222 B2
(45) Date of Patent: Nov. 20, 2012

(54) SYSTEM FOR CAPTURING AND MODIFYING LARGE PIECES OF GENOMIC DNA AND CONSTRUCTING ORGANISMS WITH CHLOROPLASTS

(75) Inventors: Michael Mendez, Del Mar, CA (US);
Bryan O'Neill, San Diego, CA (US);
Kari Mikkelson, San Diego, CA (US)

(73) Assignee: Sapphire Energy, Inc., San Diego, CA (US)

(*) Notice: Subject to any disclaimer, the term of this patent is extended or adjusted under 35 U.S.C. 154(b) by 745 days.

(21) Appl. No.: 12/287,230

(22) Filed: Oct. 6, 2008

(65) Prior Publication Data
US 2009/0123977 A1    May 14, 2009

Related U.S. Application Data

(60) Provisional application No. 60/978,024, filed on Oct. 5, 2007.

(51) Int. Cl.
| C12N 15/11 | (2006.01) |
|---|---|
| C12N 15/63 | (2006.01) |
| C12N 1/15 | (2006.01) |
| C12N 5/14 | (2006.01) |
| C12N 1/21 | (2006.01) |
| C12N 1/12 | (2006.01) |

(52) U.S. Cl. ............... 536/23.1; 435/320.1; 435/254.11; 435/419; 435/252.3; 435/257.1

(58) Field of Classification Search .................. None
See application file for complete search history.

(56) References Cited

U.S. PATENT DOCUMENTS

| 4,341,038 A | 7/1982 | Bloch et al. |
|---|---|---|
| 5,545,817 A | 8/1996 | McBride et al. |
| 5,866,404 A | 2/1999 | Bradshaw et al. |
| 5,972,614 A | 10/1999 | Ruano et al. |
| 6,872,516 B2 | 3/2005 | Evans et al. |
| 7,083,971 B1 | 8/2006 | Mendez et al. |
| 7,129,391 B1 | 10/2006 | Daniell |
| 2002/0132348 A1 | 9/2002 | Bradshaw et al. |
| 2004/0014174 A1 | 1/2004 | Mayfield et al. |
| 2004/0055209 A1 | 3/2004 | Jakkula et al. |
| 2004/0177402 A1 | 9/2004 | Daniell et al. |
| 2005/0003511 A1 | 1/2005 | Bradshaw et al. |
| 2005/0019924 A1 | 1/2005 | Hitzeman et al. |
| 2005/0260553 A1 | 11/2005 | Berzin et al. |
| 2006/0253935 A1 | 11/2006 | Daniell |
| 2007/0048848 A1 | 3/2007 | Sears |
| 2009/0123977 A1 | 5/2009 | Mendez et al. |

FOREIGN PATENT DOCUMENTS

| EP | 1571220 A2 | 9/2005 |
|---|---|---|
| KR | 970000686 B1 | 1/1997 |
| WO | WO 99/10513 A1 | 3/1999 |
| WO | WO 00/75299 A1 | 12/2000 |
| WO | WO 2005/085454 A2 | 9/2005 |
| WO | WO 2005/108568 A1 | 11/2005 |
| WO | WO 2008/003078 A2 | 1/2008 |
| WO | WO 2008/003078 A3 | 7/2008 |
| WO | WO 2008/150461 A2 | 12/2008 |
| WO | WO 2008/150461 A3 | 2/2009 |
| WO | WO 2008/150461 A4 | 4/2009 |
| WO | WO 2009/103065 A2 | 8/2009 |

OTHER PUBLICATIONS

Erion et al., "Cloning, mapping and in vitro transcription-translation of the gene from the large subunit of ribulose-1,5-biphosphage carboylase from spinach chloroplasts." PNAS, 1981 vol. 78, pp. 3459-3463.
Itaya et al., "Bottom-up genome assembly using the *Bacillus subtilis* genome vector." Nature Methods, 2008 Viol.5, pp. 41-43.
Lafontaine et al., "One-step PCT mediated strategy for the construction of conditionally expressed and epitope tagged yeast proteins." Nucleic Acid Research, vol. 24 No. 17, 1996, pp. 3469-3472.
Li et al., "Molecular cloning of the 4.1. kilobase Sdal-1 fragment of the spinach chloroplast DNA (English abstract only)" Acta Genetics Sinica, 1986 vol. 13, pp. 11-16.
Poteete et al., "Gentamicin and other cassettes for chromosomal gene replacement in *Escherichia coli*" BioTechniques, vol. 41 2006, pp. 261-262.
Verma et al., "Chloroplast vector systems for biotechnology applications." Plant Physiology, 2007 vol. 145, pp. 1129-1143.
Boynton, et al. Chloroplast transformation in *Chlamydomonas* with high velocity microprojectiles. Science. 1988; 240:1534-1538.
Daniell, et al. Transient foreign gene expression in chloroplasts of cultured tobacco cells after biolistic delivery of chloroplast vectors. Proc Natl Acad Sci U S A. Jan. 1990;87(1):88-92.
El-Sheekh, M. Stable chloroplast transformation in *Chlamydomonas reinhardtii* using microprojectile bombardment. Folia Microbiol (Praha). 2000;45(6):496-504.
Gupta, et al. Entire maize chloroplast genome is stably maintained in a yeast artificial chromosome. Plant Mol Biol. Sep. 1991;17(3):361-9.
Hokanson, et al. Hybrid yeast-bacteria cloning system used to capture and modify adenoviral and nonviral genomes. Hum Gene Ther. Mar. 1, 2003;14(4):329-39.
Invitrogen website, Pyes-dest52 vector protocols, available from http://tools.invitrogen.com/content/sfs/manuals/pyesdest52__man.pdf, last modified Nov. 20, 2002 [accessed Jan. 29, 2009].
Ohtani, et al. Location and nucleotide sequence of a tobacco chlorophlast DNA segment capable of replication in yeast. Molecular & general genetics, 1984; 195(1-2):1-4.
Rochaix, et al. Construction and characterization of autonomously replicating plasmids in the green unicellular alga *Chlamydomonas reinhardii*. Cell. Apr. 1984;36(4):925-31.

(Continued)

*Primary Examiner* — Michele K Joike
(74) *Attorney, Agent, or Firm* — Sapphire Energy, Inc.

(57) ABSTRACT

The functional analysis of genes frequently requires the manipulation of large genomic regions. A yeast-bacteria shuttle vector is described that can be used to clone large regions of DNA by homologous recombination. Also described is a method for isolating entire genomes, including chloroplast genomes, or large portions thereof, and manipulating the same. Also described are methods for determining minimal genomes, minimal pathway requirements, and minimal organelle genomes.

34 Claims, 15 Drawing Sheets

OTHER PUBLICATIONS

Rochaix, et al. Strategy, progress and prospects of transformation in *Chlamydomonas reinhardii*. NATO advanced science institutes series : Series A : Life sciences (USA). 1985; Serial No. v. 83 p. 579-592.

Uchimiya, et al. Molecular cloning of tobacco chromosomal and chloroplast DNA segments capable of replication in yeast. Molecular & general genetics.1983; 192(1-2):1-4.

Wang, et al. Cloning and delimiting one chloroplast DNA replicative origin of *Chlamydomonas*. Nucleic Acids Res. May 11, 1984;12(9):3857-72.

Bradshaw, et al. A new vector for recombination-based cloning of large DNA fragments from yeast artificial chromosomes. Nucleic Acids Res. Dec. 11, 1995; 23(23):4850-6.

Liang, et al. Site-directed mutagenesis and generation of chimeric viruses by homologous recombination in yeast to facilitate analysis of plant-virus interactions. Mol Plant Microbe Interact. Jun. 2004; 17(6):571-6.

Bradshaw, et al. A new vector for recombination-based cloning of large DNA fragments from yeast artificial chromosomes. Nucleic Acids Res. Dec. 11, 1995;23(23):4850-6.

Liang, et al. Site-directed mutagenesis and generation of chimeric viruses by homologous recombination in yeast to facilitate analysis of plant-virus interactions. Mol. Plant Microbe Interact. Jun. 2004;17(6):571-6.

Venken et al. P[acman]: a BAC transgenic platform for targeted insertion of large DNA fragments in *D.melanogaster*, Science, Dec. 2006, vol. 314, pp. 1747-1571.

Bouton, et al. Fine-structure analysis of the DNA sequence requirements for autonomous replication of *Saccharomyces cerevisiae* plasmids. Mol Cell Biol. Jul. 1986;6(7):2354-63.

Carbon J. Yeast centromeres: structure and function. Cell. Jun. 1984; 37(2):351-3.

Clark,et al. Isolation of a yeast centromere and construction of functional small circular chromosomes. Nature. Oct. 9, 1980; 287(5782):504-9.

Ketner, et al. Efficient manipulation of the human adenovirus genome as an infectious yeast artificial chromosome clone. Proc. Natl. Acad. Sci. USA Jun. 1994, vol. 91, pp. 6186-6190.

Kiss, et al. Two separate regions of the extrachromosomal ribosomal deoxyribonucleic acid of *Tetrahymena thermophila* enable autonomous replication of plasmids in *Saccharomyces cerevisiae*. Mol Cell Biol. 1981.

Murray, et al. Construction of artificial chromosomes in yeast. Nature. Sep. 1983. 15-21;305(5931):189-93.

Stinchcomb, et al. Isolation and characterisation of a yeast chromosomal replicator. Nature. Nov. 1, 1979;282(5734):39-43.

Wang, et al. Strategies for gene disruptions and plasmid constructions in fission yeast, Methods, 2004, vol. 33 No. 3, pp. 199-205.

Adam et al., "Retrofitting YACs for direct NDA transfer into plant cells. " The Plant Journal, 1997, vol. 11, pp. 1349-1358.

Baudin et al., "A simple and efficient method for direct gene deletion in *Saccharomyces cerevisiae*." Nucleic Acids Research, 1993, vol. 21, pp. 3329-3330.

Blattner et al., The complete genome sequence of *Escherichia coli* K-12. Science, 1997, vol. 277, pp. 1453-1462.

Cairns, "The chromosome of *Escherichia coli*." Cold Spring Harbor Symposia on Quantative Biology, 1963, vol. 28, pp. 43-46.

Chattoraj et al., "P1 plasmid replication: Multiple functions of RepA protein at the origin." Proc. Natl. Acad. Sci. USA, 1985, vol. 82, pp. 2588-2592.

Datsenko et al., "One-step inactivation of chromosomal genes in *Escherichia coli* K-12 using PCR products." PNAS, 2000, Vo. 97, pp. 6640-6645.

pYAC3 sequence. Genome—www.stanford.edu/vector.../PYAC3.SEQ.html. 2012.

Saski et al., "Complete chloroplast to genome sequence of Gycine max and comparative analyses with other legume genomes" Plant Molecular Biology, 2005, vol. 59, pp. 309-322.

Wilson et al., "Rapid hypothesis testing with *Candida albicans* through gene disruption with short homology regions." Journal of Bacteriology, 1999, vol. 181, pp. 1868-1874.

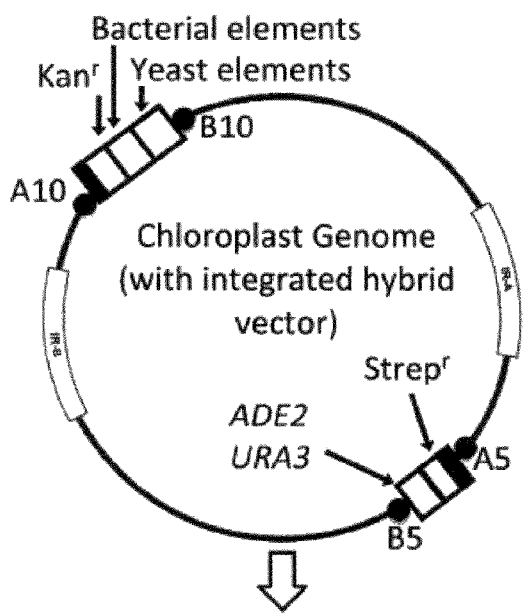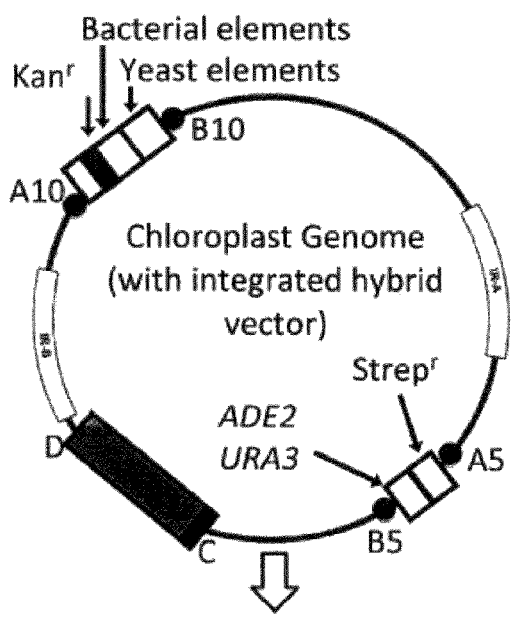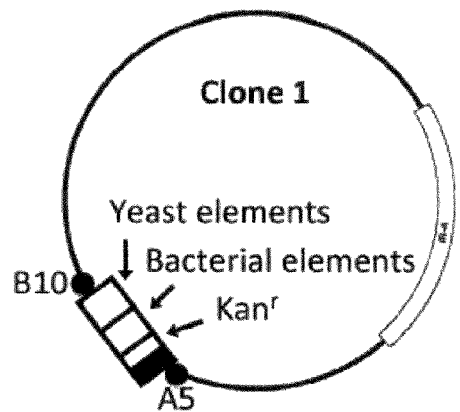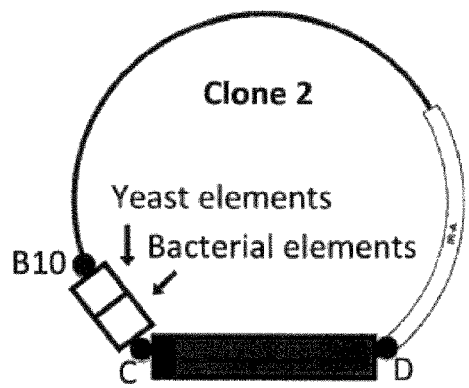
FIG. 8A
FIG. 8B

FIG. 10B Position of integration (xylanase)

FIG. 10C Position of integration (FPP synthase)

SYSTEM FOR CAPTURING AND MODIFYING LARGE PIECES OF GENOMIC DNA AND CONSTRUCTING ORGANISMS WITH CHLOROPLASTS

CROSS-REFERENCE

This application claims priority to and benefit of U.S. Provisional Application No. 60/978,024 (filed Oct. 5, 2007), which application is incorporated herein by reference.

BACKGROUND OF THE INVENTION

For the functional analysis of many genes, investigators need to isolate and manipulate large DNA fragments. The advent of genomics and the study of genomic regions of DNA have generated a need for vectors capable of carrying large DNA regions.

In general, two types of yeast vector systems are presently available. The first type of vector is one capable of transferring small insert DNA between yeast and bacteria. A second type of vector is a fragmenting vector which creates interstitial or terminal deletions in yeast artificial chromosomes (YACs). The small insert shuttle vectors are able to recombine with and recover homologous sequences. They are centromere-based and replicate stably and autonomously in yeast, but also contain a high-copy origin of replication for maintenance as bacterial plasmids. However, these vectors are limited by their small insert capacity. The second type of vector (also known as fragmenting vectors) has recombinogenic sequences, but is unable to transfer the recovered insert DNA to bacteria for large preparations of DNA.

Researchers use fragmentation techniques to narrow down the region of interest in YACs. However, isolating sufficient quantities of YAC DNA from agarose gels for microinjection or electroporation remains cumbersome. Purification remains a problem when the YAC comigrates with an endogenous chromosome. In addition, YACs may be chimeric or contain additional DNA regions that are not required for the particular functional study.

Types of vectors available for cloning large fragments in bacteria are cosmids, P1s and bacterial artificial chromosomes (BACs). These vectors are limited to bacteria and cannot be shuttled to yeast for modification by homologous recombination. Bacterial vectors are also limited in their use for transforming plants and algae. For example, though chloroplasts are thought to originate from the endosymbiosis of photosynthetic bacteria into eukaryotic hosts translation of chloroplasts in more complex. Adding to the complexity of genetically engineering plants and algae is the presence of multiple chloroplasts with multiple copies of the chloroplast genome. Thus, there exists a need for developing a method to express proteins from large fragments of DNA in the chloroplasts of plants and algae

SUMMARY OF THE INVENTION

The present invention relates to compositions and methods of isolating, characterizing, and/or modifying large DNA, including entire genomes of bacteria and chloroplasts. The compositions include shuttle vectors into which target DNA may be inserted. The methods include modifying or manipulating target DNA by removing, adding or rearranging portions and introducing the modified DNA into a host.

One aspect of the present invention provides an isolated vector comprising a yeast element, a bacterial origin of replication, and at least 20 kb genomic DNA. In some vectors, the yeast element is a yeast centromere, a yeast autonomous replicating sequence, yeast auxotrophic marker, or a combination thereof. The DNA may be from a non-vascular photosynthetic organism, for example a macroalgae, microalgae, *Ch. vulgaris, C. reinhardtii, D. salina, S. quadricanda* or *H. pluvalis*. In some embodiments, the genomic DNA is modified, for example by insertion of a heterologous or homologous polynucleotide, deletion of one or more nucleic acid bases, mutation of one or more nucleic acid bases, rearrangement of one or more polynucleotides, or a combination thereof. In some instances, the modification is synthetic. Vectors of the present invention, when transformed into a host cell, may result in production of a product not naturally produced by the host cell. Some examples of such products include biomass-degrading enzymes, a fatty acids, terpenes or terpenoids. In some host cells, expression of the vector results in an increase production of a product naturally produced by said host cell, for example, a biomass-degrading enzyme, a terpene or a terpenoid. The vectors of the present invention may further comprise one or more selection markers, for example, a yeast marker, a yeast antibiotic resistance marker, a yeast auxotrophic marker, a bacterial marker, a bacterial antibiotic resistance marker, a bacterial auxotrophic marker, an algae marker, an algae antibiotic resistance marker, an algae auxotrophic marker, or a combination thereof. Vectors of the present invention may also contain chloroplast genomic DNA which comprises 1) 1-200 genes; 2) all essential chloroplast genes; and/or 3) 30-400 kb.

Also described herein is a host cell comprising the vectors described herein. Exemplary host cells may be naturally non-photosynthetic or photosynthetic and include, for example, *Saccharomyces cerevisiae, Escherichia coli*, macroalgae, microalgae, *Ch. vulgaris, C. reinhardtii, D. salina, S. quadricanda* or *H. pluvalis*.

In another aspect of the invention, a method for producing a vector is provided where the method involves inserting targeting DNA into a vector—where the vector comprises a yeast centromere, a yeast autonomous replicating sequence, and a bacterial origin of replication, transforming an organism with the vector and capturing a portion of a chloroplast genome, thus producing a vector with a portion of a chloroplast genome. In some instances, the targeting DNA is chloroplast genomic DNA. This method may be used to capture a portion of a genome which is 10-400 kb in length. In some instances, the capturing step occurs by recombination. The captured portion of a chloroplast genome may be co-transformed into an organism with a vector, thus the recombination step may occur in vivo. Organisms used to practice methods disclosed herein may be eukaryotic and/or photosynthetic. In some instances, the organism is a non-vascular photosynthetic organism, for example a macroalgae, microalgae, *Ch. vulgaris, C. reinhardtii, D. salina, S. quadricanda* or *H. pluvalis*. Organisms used to practice methods disclosed herein may also be non-photosynthetic, for example yeast. In some instances, a non-photosynthetic organism may contain exogenous chloroplast DNA. In some embodiments, an additional step of modifying a portion of a chloroplast genome is utilized. A modification may be achieved through homologous recombination. Such recombination may occur in an organism, for example a eukaryotic and/or photosynthetic organism. In some instances, the organism is a non-vascular photosynthetic organism, for example a macroalgae, microalgae, *Ch. vulgaris, C. reinhardtii, D. salina, S. quadricanda* or *H. pluvalis*. In other instances, the organism may be non-photosynthetic, for example a yeast. In embodiments with a modification step, the step may comprise addition of a polynucleotide, deletion of one or more nucleic acid bases, mutation of one or more nucleic acid bases, rearrangement or a polynucleotide, or combination thereof.

Further disclosed herein is an isolated vector comprising essential chloroplast genes, a selectable marker and a manipulation in one or more nucleic acids in the vector. In some instances, essential chloroplast genes are cloned from a non-vascular photoshynthetic organism such as macroalgae, microalgae, *Ch. vulgaris, C. reinhardtii, D. salina, S. quadricanda* or *H. pluvalis*. Essential chloroplast genes for use in the vectors described herein may be synthetic. The vectors described herein may further comprise an expression cassette, which may further comprise a region for integration into target DNA, for example organelle DNA. The vectors described herein may also contain one or more selection markers, for example, an auxotrophic marker, an antibiotic resistance marker, a chloroplast marker, or combinations thereof. In some instances, the essential chloroplast genes are those required for chloroplast function, photosynthesis, carbon fixation, production of one or more hydrocarbons, or a combination thereof. Essential chloroplast genes may comprise up to 200 genes and/or consist of up to 400 kb. In some of the vectors described herein a manipulation in one or more nucleic acids is an addition, deletion, mutation, or rearrangement. In some instances, expression of the vector in a host cell produces a product not naturally produced by said host cell. In other instances, expression of a vector of the present invention results in an increase production of a product naturally produced by said host cell. Examples of such products are biomass degrading enzymes, fatty acids, terpenes or terpenoids.

As described herein, one aspect of the present invention is an isolated chloroplast comprising a vector of the present invention. In another aspect, a host cell comprising a vector of the present invention is provided. Host cells useful in the present invention may be naturally non-photosynthetic or naturally photosynthetic. Examples of organisms useful for the present invention include *Saccharomyces cerevisiae, Escherichia coli*, macroalgae, microalgae, *Ch. vulgaris, C. reinhardtii, D. salina, S. quadricanda* or *H. pluvalis*.

In another aspect of the present invention, a method for transforming a cell or organism is provided where the method comprises inserting into said cell or organism a vector comprising all essential chloroplast genes and optionally one or more genes not naturally occurring in said cell or organism. In some embodiments, the method further comprises the step of eliminating substantially all chloroplast genomes in said cell or organism. A cell or organism useful for this method may be photosynthetic, non-photosynthetic and/or eukaryotic. A cell or organism useful for this method may be non-vascular. In some instances, the vector for use in this method may also comprise an expression cassette and the expression cassette may be capable of integrating into non-nuclear DNA. In one embodiment the one or more genes not naturally occurring in the cell or organism is a gene in the isoprenoid pathway, MVA pathway, or MEP pathway. In another embodiment, the essential chloroplast genes are those that are required for chloroplast function, photosynthesis, carbon fixation, production of one or more hydrocarbons, or a combination thereof.

Further provided herein is a method for modifying an organism comprising the steps of transforming the organism with a vector comprising one or more polynucleotides sufficient to perform chloroplast function. In some instances, a vector useful for this method further comprises a sequence for production or secretion of a compound from said organism. In some instances, the compound is an isoprenoid. In other instances, the vector comprises all essential chloroplast genes. In still other instances, the essential chloroplast genes are rearranged or mutated. An organism useful for some embodiments comprises essentially no chloroplast genome prior to transformation.

Yet another method provided herein is a method for making a product from an organism comprising the step of transforming said organism with a vector comprising at least 20 kb of genomic DNA and one or more of the following: (i) a gene not naturally occurring in said organism; (ii) a deletion in a gene naturally occurring in said organism; (iii) a rearrangement of genes naturally occurring in said organism; and (iv) a mutation in a gene naturally occurring in said organism. In some instances, the organism is naturally photosynthetic. In other instances, the additional genes encode enzymes in the isoprenoid pathway, MVA pathway, or MEP pathway. In still another embodiment, the present disclosure provides a method for transforming a cell or organism comprising inserting into said cell or organism a chloroplast and a vector comprising all essential chloroplast genes.

The present disclosure also provides a method of producing an artificial chloroplast genome comprising the steps of: (a) providing a vector comprising one or more essential chloroplast genes; (b) adding to said vector a DNA fragment; (c) transforming a cell or organism with the vector produced by step (b); and (d) determining whether chloroplast function exists with said added DNA fragment. In some instances, the added DNA fragments comprises one or more coding regions for an enzyme in the isoprenoid, MVA or MEP pathway.

The present disclosure also provides a shuttle vector comprising a chloroplast genome. A genome may be modified. Also provided herein is a vector comprising an isolated, functional chloroplast genome. A chloroplast genome useful in such a vector may be modified.

Further provided herein is a method of producing an artificial chloroplast genome comprising the steps of: (a) providing a vector comprising all essential chloroplast genes; and (b) removing, adding, mutating, or rearranging DNA from the chloroplast genome. Such a method may further comprise the steps of transforming a redacted genome into a host organism; and (d) determining chloroplast function in the host organism. In some instances, steps (b), (c), and (d) are repeated. In still other instances, the chloroplast genome is from an organism selected from the group consisting of: macroalgae, microalgae, *Ch. vulgaris, C reinhardtii, D. salina, S. quadricanda* or *H. pluvalis*. In other instances, the host organism is selected from the group consisting of: macroalgae, microalgae, *Ch. vulgaris, C. reinhardtii, D. salina, S. quadricanda* or *H. pluvalis*. For some embodiments, the method may further comprise the step of removing redundant DNA from a chloroplast genome. In other embodiments, the vector comprises all or substantially all of a chloroplast genome. A chloroplast genome useful in the present invention may be cloned from a photosynthetic organism or may be a synthetic chloroplast genome. In some instances, the vector further comprises a gene not naturally occurring in the host organism, for example a gene from the isoprenoid pathway, MVA pathway, or MEP pathway.

Yet another method provided herein is a method of producing an artificial chloroplast genome comprising the steps of: (a) providing a vector comprising an entire chloroplast genome; (b) deleting a portion of said entire chloroplast genome; and (c) determining whether chloroplast function exists without said deleted portion. In another aspect of the present invention, a composition comprising an isolated and functional chloroplast genome is provided. In some instances, a composition comprises a modification to said chloroplast genome.

Further provided herein is an ex vivo vector comprising a nucleic acid comprising at least about 10% of a chloroplast genome and a manipulation in one or more nucleic acids in the vector. In some instances, the nucleic acid is cloned from a non-vascular photosynthetic organism, for example a macroalgae, microalgae, *Ch. vulgaris, C. reinhardtii, D. salina, S. quadricanda* or *H. pluvalis*. In some instances, the nucleic acid is synthetic. A vector of the present invention may further comprise an expression cassette and an expression cassette may further comprise a region for integration into target DNA. In some instances, the target DNA is organelle DNA. A vector useful in-the present invention may further comprise one or more selection markers, for example an auxotrophic marker, an antibiotic resistance marker, a chloroplast marker, or combinations thereof. In some embodiments, a manipulation in one or more nucleic acids in a vector may be an addition, deletion, mutation, or rearrangement. Expression of the vector may result in production of a product not naturally produced by a host cell and/or an increase production of a product naturally produced by a host cell. Examples of some products of the present invention include a terpene, terpenoid, fatty acid, or biomass degrading enzyme.

Also provided herein is an ex vivo vector comprising a nucleic acid comprising at least about 20 kilobases of a chloroplast genome and a manipulation in one or more nucleic acids in said vector. In some instances, the nucleic acid is cloned from a non-vascular photosynthetic organism, for example a macroalgae, microalgae, *Ch. vulgaris, C reinhardtii, D. salina, S. quadricanda* or *H. pluvalis*. In some instances, the nucleic acid is synthetic. A vector of the present invention may further comprise an expression cassette and an expression cassette may further comprise a region for integration into target DNA. In some instances, the target DNA is organelle DNA. A vector useful in the present invention may further comprise one or more selection markers, for example an auxotrophic marker, an antibiotic resistance marker, a chloroplast marker, or combinations thereof. In some embodiments, a manipulation in one or more nucleic acids in a vector may be an addition, deletion, mutation, or rearrangement. Expression of the vector may result in production of a product not naturally produced by a host cell and/or an increase production of a product naturally produced by a host cell. Examples of some products of the present invention include a terpene, terpenoid, fatty acid, or biomass degrading enzyme.

Further provided herein is a method of producing a vector containing a reconstructed genome, comprising: introducing two or more vectors into a host cell, wherein the vectors comprise fragments of a genome, recombining the vectors into a single vector comprising at least about 90% of a genome, thereby producing a vector containing a reconstructed genome. In some instances, the host cell is eukaryotic, for example, *S. cerevisiae*. In other instances, the genome is an organelle genome. The organelle may be a chloroplast, for example a chloroplast from an alga, particularly a microalga such as *Ch. vulgaris, C. reinhardtii, D. salina, S. quadricanda* or *H. pluvalis*. In some instances, the two or more vectors comprise a selectable marker. In other instances, at least one of said fragments is synthetic. In still other instances, a further step comprising modifying a portion of the genome is useful in this method. Such a modification may comprise an addition, deletion, mutation, or rearrangement. In other embodiments, the modification is the addition of an exogenous nucleic acid which results in the production or increased production of a terpene, terpenoid, fatty acid or biomass degrading enzyme.

Incorporation By Reference

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

In the figures, the following abbreviations are used: HIS3: yeast HIS3 gene; TRP1: yeast TRP1 gene; URA3: yeast URA3 gene; ADE2: yeast ADE2 gene; LYS2: yeast LYS2 gene; TEL: yeast telomere; CEN: yeast centromere; ARS: autonomously replicating sequences, yeast origin of replication; 5FOA: 5-fluoroorotic acid; Kan: kanamycin resistance gene; P1 plasmid rep: P1 plasmid replicon; p1 lytic rep: p1 lytic replicon.

FIGS. 8A-8B are schematics showing architecture of isolated ex vivo vectors containing chloroplast genome DNA.

FIGS. 10A-10C are schematics of restriction analysis for manipulation vectors. A) Schematic of vector architecture. B) Analysis of modified vector by restriction analysis with EcoRI

DETAILED DESCRIPTION OF THE INVENTION

Figure 1A:
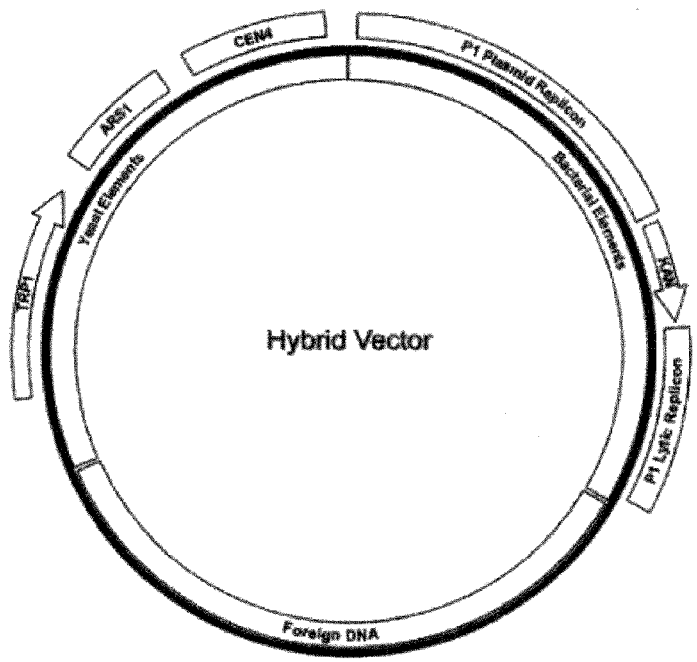
FIG. 1 provides a general description of a hybrid vector of the present invention. A) Vector schematic. B) DNA shuttling between organisms.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of yeast genetics useful for selected aspects of the invention include: Sherman et al. "Laboratory Course Manual Methods in Yeast Genetics", Cold Spring Harbor Laboratory, Cold Spring Harbor, N.Y., 1986 and Guthrie et al., "Guide to Yeast Genetics and Molecular Biology", Academic, New York, 1991.

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted. This invention teaches methods and describes tools for capturing and modifying large pieces of DNA. It is especially useful for modifying genomic DNA, including the whole genome of an organism or organelle, or a part thereof. Novel prophetic uses of the invention are also described. The invention relates to the manipulation and delivery of large nucleic acids. The invention further relates to recombinational cloning vectors and systems and to methods of using the same.

Contemporary methods for genetically engineering genomes (e.g., chloroplast genomes) are time intensive (>1 month) and allow for only a limited number of manipulations at a time. If multiple modifications to a target genome are desired, the process must be iterated, flurther increasing the time required to generate a desired strain. Because metabolic engineering and/or synthetic biology require numerous modifications to a genome, these technologies are not amenable to rapid introduction of modifications to a genome. Thus, a new technology that allows for multiple modification of the chloroplast genome in a short amount of time will enable the application of metabolic engineering and/or synthetic biology to chloroplast genomes. The disclosure herein describes such technology.

The instant invention provides a versatile, recombinational approach to the capture, cloning, and manipulation of large nucleic acids from target cells and organelles (e.g., chloroplasts). One aspect of the present invention provides a recombinational cloning system. More specifically, the invention provides vectors, which in some embodiments, rely on homologous recombination technologies to mediate the isolation and manipulation of large nucleic acid segments. Another aspect of the present invention provides methods for using such recombinational cloning vectors to clone, to manipulate and to deliver large nucleic acids to target cells and/or organelles such as chloroplasts.

In one preferred embodiment, homologous recombination is performed in vitro. In a particularly preferred embodiment of the invention, homologous recombination is performed in vivo. In a more preferred embodiment, homologous recombination occurs in an algae cell. In another more preferred embodiment, homologous recombination occurs in a yeast cell. In one preferred embodiment, homologous recombination occurs in *Saccharomyces cerevisiae* or *Saccharomyces pombe*. In yeast, the combination of efficient recombination processes and the availability of numerous selectable markers provides for rapid and complex engineering of target DNA sequences. Once all of the modifications are made to an ex vivo vector containing chloroplast genome DNA, the entire vector can be introduced into a chloroplast in a single transformation step. Thus, employing yeast technology will enable the application of metabolic engineering and/or synthetic biology to chloroplast genomes. One aspect of the present invention provides an isolated vector comprising a yeast element, a bacterial origin of replication, and at least 20 kb genomic DNA. In some vectors, the yeast element is a yeast centromere, a yeast autonomous replicating sequence, or a combination thereof. The DNA may be from a non-vascular photosynthetic organism, for example a macroalgae, microalgae, *Ch. vulgaris*, *C. reinhardtii*, *D. salina*, *S. quadricanda* or *H. pluvalis*. In some embodiments, the genomic DNA is modified, for example by insertion of a heterologous or homologous polynucleotide, deletion of one or more nucleic acid bases, mutation of one or more nucleic acid bases, rearrangement of one or more polynucleotides, or a combination thereof. In some instances, the modification is synthetic. Vectors of the present invention, when transformed into a host cell, may result in production of a product not naturally produced by the host cell. Some examples of such products include biomass-degrading enzymes, a fatty acids, terpenes or terpenoids. In some host cells, expression of the vector results in an increase production of a product naturally produced by said host cell, for example, a biomass-degrading enzyme, a terpene or a terpenoid. The vectors of the present invention may further comprise one or more selection markers, for example, a yeast marker, a yeast antibiotic resistance marker, a bacterial marker, a bacterial antibiotic resistance marker, an algae marker, an algae antibiotic resistance marker or a combination thereof. Vectors of the present invention may also contain chloroplast genomic DNA which comprises 1) 1-200 genes; 2) all essential chloroplast genes; and/or 3) 30-400 kb.

Also described herein is a host cell comprising the vectors described herein. Exemplary host cells may be naturally non-photosynthetic or photosynthetic and include, for example, *Saccharomyces cerevisiae*, *Escherichia coli*, macroalgae, microalgae, *Ch. vulgaris*, *C. reinhardtii*, *D. salina*, *S. quadricanda* or *H. pluvalis*.

In another aspect of the invention, a method for producing a vector is provided where the method involves inserting targeting DNA into a vector—where the vector comprises a yeast centromere, a yeast autonomous replicating sequence, and a bacterial origin of replication, transforming an organism with the vector and capturing a portion of a chloroplast genome, thus producing a vector with a portion of a chloroplast genome. In some instances, the targeting DNA is chloroplast genomic DNA. This method may be used to capture a portion of a genome which is 10-400 kb in length. In some instances, the capturing step occurs by recombination. The captured portion of a chloroplast genome may be co-transformed into an organism with a vector, thus the recombination step may occur in vivo. Organisms used to practice methods disclosed herein may be eukaryotic and/or photosynthetic. In some instances, the organism is a non-vascular photosynthetic organism, for example a macroalgae, microalgae, *Ch. vulgaris, C. reinhardtii, D. salina, S. quadricanda* or *H. pluvalis*. Organisms used to practice methods disclosed herein may also be non-photosynthetic, for example yeast. In some instances, a non-photosynthetic organism may contain exogenous chloroplast DNA. In some embodiments, an additional step of modifying a portion of a chloroplast genome is utilized. A modification may be achieved through homologous recombination. Such recombination may occur in an organism, for example a eukaryotic and/or photosynthetic organism. In some instances, the organism is a non-vascular photosynthetic organism, for example a macroalgae, microalgae, *Ch. vulgaris, C. reinhardtii, D. salina, S. quadricanda* or *H. pluvalis*. In other instances, the organism may be non-photosynthetic, for example a yeast. In embodiments with a modification step, the step may comprise addition of a polynucleotide, deletion of one or more nucleic acid bases, mutation of one or more nucleic acid bases, rearrangement or a polynucleotide, or combination thereof.

Further disclosed herein is an isolated vector comprising essential chloroplast genes, a selectable marker and a manipulation in one or more nucleic acids in the vector. In some instances, essential chloroplast genes are cloned from a non-vascular photoshynthetic organism such as macroalgae, microalgae, *Ch. vulgaris, C. reinhardtii, D. salina, S. quadricanda* or *H. pluvalis*. Essential chloroplast genes for use in the vectors described herein may be synthetic. The vectors described herein may further comprise an expression cassette, which may further comprise a region for integration into target DNA, for example organelle DNA. The vectors described herein may also contain one or more selection markers, for example, an auxotrophic marker, an antibiotic resistance marker, a chloroplast narker, or combinations thereof. In some instances, the essential chloroplast genes are those required for chloroplast function, photosynthesis, carbon fixation, production of one or more hydrocarbons, or a combination thereof. Essential chloroplast genes may comprise up to 200 genes and/or consist of up to 400 kb. In some of the vectors described herein a manipulation in one or more nucleic acids is an addition, deletion, mutation, or rearrangement. In some instances, expression of the vector in a host cell produces a product not naturally produced by said host cell. In other instances, expression of a vector of the present invention results in an increase production of a product naturally produced by said host cell. Examples of such products are biomass degrading enzymes, fatty acids, terpenes or terpenoids.

As described herein, one aspect of the present invention is an isolated chloroplast comprising a vector of the present invention. In another aspect, a host cell comprising a vector of the present invention is provided. Host cells useful in the present invention may be naturally non-photosynthetic or naturally photosynthetic. Examples of organisms useful for the present invention include *Saccharomyces cerevisiae, Escherichia coli*, macroalgae, microalgae, *Ch. vulgaris, C reinhardtii, D. salina, S. quadricanda* or *H. pluvalis*.

In another aspect of the present invention, a method for transforming a cell or organism is provided where the method comprises inserting into said cell or organism a vector comprising all essential chloroplast genes and optionally one or more genes not naturally occurring in said cell or organism. In some embodiments, the method further comprises the step of eliminating substantially all chloroplast genomes in said cell or organism. A cell or organism useful for this method may be photosynthetic, non-photosynthetic and/or eukaryotic. A cell or organism useful for this method may be non-vascular. In some instances, the vector for use in this method may also comprise an expression cassette and the expression cassette may be capable of integrating into non-nuclear DNA. In one embodiment the one or more genes not naturally occurring in the cell or organism is a gene in the isoprenoid pathway, MVA pathway, or MEP pathway. In another embodiment, the essential chloroplast genes are those that are required for chloroplast function, photosynthesis, carbon fixation, production of one or more hydrocarbons, or a combination thereof.

Further provided herein is a method for modifying an organism comprising the steps of transforming the organism with a vector comprising one or more polynucleotides sufficient to perform chloroplast function. In some instances, a vector useful for this method further comprises a sequence for production or secretion of a compound from said organism. In some instances, the compound is an isoprenoid. In other instances, the vector comprises all essential chloroplast genes. In still other instances, the essential chloroplast genes are rearranged or mutated. An organism useful for some embodiments comprises essentially no chloroplast genome prior to transformation.

Yet another method provided herein is a method for making a product from an organism comprising the step of transforming said organism with a vector comprising at least 20 kb of genomic DNA and one or more of the following: (i) a gene not naturally occurring in said organism; (ii) a deletion in a gene naturally occurring in said organism; (iii) a rearrangement of genes naturally occurring in said organism; and (iv) a mutation in a gene naturally occurring in said organism. In some instances, the organism is naturally photosynthetic. In other instances, the additional genes encode enzymes in the isoprenoid pathway, MVA pathway, or MEP pathway. In still another embodiment, the present disclosure provides a method for transforming a cell or organism comprising inserting into said cell or organism a chloroplast and a vector comprising all essential chloroplast genes.

The present disclosure also provides a method of producing an artificial chloroplast genome comprising the steps of: (a) providing a vector comprising one or more essential chloroplast genes; (b) adding to said vector a DNA fragment; (c) transforming a cell or organism with the vector produced by step (b); and (d) determining whether chloroplast function exists with said added DNA fragment. In some instances, the added DNA fragments comprises one or more coding regions for an enzyme in the isoprenoid, MVA or MEP pathway.

The present disclosure also provides a shuttle vector comprising a chloroplast genome. A genome may be modified. Also provided herein is a vector comprising an isolated, functional chloroplast genome. A chloroplast genome useful in such a vector may be modified.

Further provided herein is a method of producing an artificial chloroplast genome comprising the steps of: (a) providing a vector comprising all essential chloroplast genes; and (b) removing, adding, mutating, or rearranging DNA from the chloroplast genome. Such a method may further comprise the steps of transforming a redacted genome into a host organism;

and (d) determining chloroplast function in the host organism. In some instances, steps (b), (c), and (d) are repeated. In still other instances, the chloroplast genome is from an organism selected from the group consisting of: macroalgae, microalgae, *Ch. vulgaris, C. reinhardtii, D. salina, S. quadricanda* or *H. pluvalis*. In other instances, the host organism is selected from the group consisting of: macroalgae, microalgae, *Ch. vulgaris, C. reinhardtii, D. salina, S. quadricanda* or *H. pluvalis*. For some embodiments, the method may further comprise the step of removing redundant DNA from a chloroplast genome. In other embodiments, the vector comprises all or substantially all of a chloroplast genome. A chloroplast genome useful in the present invention may be cloned from a photosynthetic organism or may be a synthetic chloroplast genome. In some instances, the vector further comprises a gene not naturally occurring in the host organism, for example a gene from the isoprenoid pathway, MVA pathway, or MEP pathway.

Yet another method provided herein is a method of producing an artificial chloroplast genome comprising the steps of: (a) providing a vector comprising an entire chloroplast genome; (b) deleting a portion of said entire chloroplast genome; and (c) determining whether chloroplast function exists without said deleted portion. In another aspect of the present invention, a composition comprising an isolated and functional chloroplast genome is provided. In some instances, a composition comprises a modification to said chloroplast genome.

Further provided herein is an ex vivo vector comprising a nucleic acid comprising at least about 10% of a chloroplast genome and a manipulation in one or more nucleic acids in the vector. In some instances, the nucleic acid is cloned from a non-vascular photosynthetic organism, for example a macroalgae, microalgae, *Ch. vulgaris, C. reinhardtii, D. salina, S. quadricanda* or *H. pluvalis*. In some instances, the nucleic acid is synthetic. A vector of the present invention may further comprise an expression cassette and an expression cassette may further comprise a region for integration into target DNA. In some instances, the target DNA is organelle DNA. A vector useful in the present invention may flurther comprise one or more selection markers, for example an auxotrophic marker, an antibiotic resistance marker, a chloroplast marker, or combinations thereof. In some embodiments, a manipulation in one or more nucleic acids in a vector may be an addition, deletion, mutation, or rearrangement. Expression of the vector may result in production of a product not naturally produced by a host cell and/or an increase production of a product naturally produced by a host cell. Examples of some products of the present invention include a terpene, terpenoid, fatty acid, or biomass degrading enzyme.

Also provided herein is an ex vivo vector comprising a nucleic acid comprising at least about 20 kilobases of a chloroplast genome and a manipulation in one or more nucleic acids in said vector. In some instances, the nucleic acid is cloned from a non-vascular photosynthetic organism, for example a macroalgae, microalgae, *Ch. vulgaris, C. reinhardtii, D. salina, S. quadricanda* or *H. pluvalis*. In some instances, the nucleic acid is synthetic. A vector of the present invention may further comprise an expression cassette and an expression cassette may further comprise a region for integration into target DNA. In some instances, the target DNA is organelle DNA. A vector useful in the present invention may further comprise one or more selection markers, for example an auxotrophic marker, an antibiotic resistance marker, a chloroplast marker, or combinations thereof. In some embodiments, a manipulation in one or more nucleic acids in a vector may be an addition, deletion, mutation, or rearrangement. Expression of the vector may result in production of a product not naturally produced by a host cell and/or an increase production of a product naturally produced by a host cell. Examples of some products of the present invention include a terpene, terpenoid, fatty acid, or biomass degrading enzyme.

Further provided herein is a method of producing a vector containing a reconstructed genome, comprising: introducing two or more vectors into a host cell, wherein the vectors comprise fragments of a genome, recombining the vectors into a single vector comprising at least about 90% of a genome, thereby producing a vector containing a reconstructed genome. In some instances, the host cell is eukaryotic, for example, *S. cerevisiae*. In other instances, the genome is an organelle genome. The organelle may be a chloroplast, for example a chloroplast from an alga, particularly a microalga such as *Ch. vulgaris, C. reinhardtii, D. salina, S. quadricanda* or *H. pluvalis*. In some instances, the two or more vectors comprise a selectable marker. In other instances, at least one of said fragments is synthetic. In still other instances, a further step comprising modifying a portion of the genome is useful in this method. Such a modification may comprise an addition, deletion, mutation, or rearrangement. In other embodiments, the modification is the addition of an exogenous nucleic acid which results in the production or increased production of a terpene, terpenoid, fatty acid or biomass degrading enzyme.

Large DNA Cloning and Content

An advantage of this invention is that it provides for the cloning, manipulation, and delivery of a vector containing chloroplast genome DNA consisting of up to all chloroplast genes (or sequences). The chloroplast genome DNA contained in the vector can be obtained by recombination of a hybrid cloning vector with one contiguous fragment of DNA or by recombination of two or more contiguous fragments of DNA.

The methods and compositions of the present invention may include captured and/or modified large pieces of DNA may comprise DNA from an organelle, such as mitochondrial DNA or plastid DNA (e.g., chloroplast DNA). The captured and/or modified large pieces of DNA may also comprise the entirety of an organelle's genome, e.g., a chloroplast genome. In other embodiments, the captured and/or modified large pieces of DNA comprise a portion of a chloroplast genome. A chloroplast genome may originate from any vascular or non-vascular plant, including algae, bryophytes (e.g., mosses, ferns), gymnosperms (e.g., conifers), and angiosperms (e.g., flowering plants—trees, grasses, herbs, shrubs). A chloroplast genome, or essential portions thereof, may comprise synthetic DNA, rearranged DNA, deletions, additions, and/or mutations. A chloroplast genome, or portions thereof, may comprise a one or more deletions, additions, mutations, and/or rearrangements. The deletions, additions, mutations, and/or rearrangements may be naturally found in an organism, for example a naturally occurring mutation, or may not be naturally found in nature. The chloroplast or plastid genomes of a number of organisms are widely available, for example, at the public database from the NCBI Organelle Genomes section available at http://www.ncbi.nlm.nih.gov/genomes/static/euk_o.html.

The target DNA sequence described herein may comprise at least 1, 2, 3, 4, or 5 deletions, additions, mutations, and/or rearrangements as compared to a control sequence (naturally occurring sequence). In some embodiments, the mutations may be functional or nonfunctional. For example, a functional mutation may have an effect on a cellular function when the mutation is present in a host cell as compared to a control cell without the mutation. A non-functional mutation may be silent in function, for example, there is no discernable difference in phenotype of a host cell without the mutation as compared to a cell with the mutation.

Captured and/or modified large pieces of DNA (e.g., target DNA), may comprise a minimal or minimized chloroplast genome (e.g., the minimum number of genes and/or DNA fragment, required for chloroplast functionality). The captured and/or modified DNA may comprise the essential chloroplast genes, it may comprise a portion or all, or substantially all of the essential chloroplast genes. An essential gene may be a gene that is essential for one or more metabolic processes or biochemical pathways. An essential gene may be a gene required for chloroplast function, such as photosynthesis, carbon fixation, or hydrocarbon production. An essential gene may also be a gene that is essential for gene expression, such as transcription, translation, or other process(es) that affect gene expression. The essential genes may comprise mutations or rearrangements. Essential genes may also comprise a minimally functional set of genes to perform a function. For example, a particular function (e.g., photosynthesis) may be performed inefficiently by a set of genes/gene products, however, this set would still comprise essential genes because the function is still performed.

Modified DNA may comprise at least 5, 10, 15, 20, 25, 30, 40, or 50 essential genes. In some embodiments, the DNA may comprise essential chloroplast genomic sequence of up to 150 kb in length. The DNA may comprise essential chloroplast genes as well as non-essential chloroplast gene sequences. The DNA may be single stranded or double stranded, linear or circular, relaxed or supercoiled. The DNA may also be in the form of an expression cassette. For example, an expression cassette may comprise an essential gene to be expressed in a host cell. The expression cassette may comprise one or more essential genes as well as DNA sequences that promote the expression of the essential genes. The expression cassette may also comprise a region for integration into target DNA of a host. The expression cassette may also comprise one or more essential genes and one or more genes not naturally occurring in a host cell comprising the expression cassette. One of ordinary skill in the arts will easily ascertain various combinations of the aforementioned aspects of the expression cassettes.

In other instances, captured and/or modified pieces of DNA may comprise the entire genome of a plastid or organelle. For example, about 10%, 11%, 12%, 13%, 14%, 15%, 16%, 17%, 18%, 19%, 20%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%; 80%, 81%, 82%, 83%, 84%, 85%, 86%, 87%, 88%, 89%, 90%, 91%, 92%, 93%, 94%, 95%, 96%, 97%, 98%, 99% of a plastid genome, or more. In one embodiment the captured and/or modified large pieces of DNA may comprise 10-100%, 20-100%, 30-100%, 40-100%, 50-100%, 60-100%, 70-100%, 80-100%, or 90-100% of the entire genome of a plastid or cell.

In still other instances, the captured and/or modified large pieces of DNA may comprise about 10 kb, 11 kb, 12 kb, 13 kb, 14 kb, 15 kb, 16 kb, 17 kb, 18 kb, 19 kb, 20 kb, 21 kb, 22 kb, 23 kb, 24 kb, 25 kb, 26 kb, 27 kb, 28 kb, 29 kb, 30 kb, 31 kb, 32 kb, 33 kb, 34 kb, 35 kb, 36 kb, 37 kb, 38 kb, 39 kb, 40 kb, 41 kb, 42 kb, 43 kb, 44 kb, 45 kb, 46 kb, 47 kb, 48 kb, 49 kb, 50 kb, 51 kb, 52 kb, 53 kb, 54 kb, 55 kb, 56 kb, 57 kb, 58 kb, 59 kb, 60 kb, 61 kb, 62 kb, 63 kb, 64 kb, 65 kb, 66 kb, 67 kb, 68 kb, 69 kb, 70 kb, 71 kb, 72 kb, 73 kb, 74 kb, 75 kb, 76 kb, 77 kb, 78 kb, 79 kb, 80 kb, 81 kb, 82 kb, 83 kb, 84 kb, 85 kb, 86 kb, 87 kb, 88 kb, 89 kb, 90 kb, 91 kb, 92 kb, 93 kb, 94 kb, 95 kb, 96 kb, 97 kb, 98 kb, 99 kb, 100 kb, 101 kb, 102 kb, 103 kb, 104 kb, 105 kb, 106 kb, 107 kb, 108 kb, 109 kb, 110 kb, 111 kb, 112 kb, 113 kb, 114 kb, 115 kb, 116 kb, 117 kb, 118 kb, 119 kb, 120 kb, 121 kb,122 kb, 123 kb, 124 kb, 125 kb, 126 kb, 127 kb, 128 kb, 129 kb, 130 kb, 131 kb, 132 kb, 133 kb, 134 kb, 135 kb, 136 kb, 137 kb, 138 kb, 139 kb, 140 kb, 141 kb, 142 kb, 143 kb, 144 kb, 145 kb, 146 kb, 147 kb, 148 kb, 149 kb, 150 kb, 151 kb, 152 kb, 153 kb, 154 kb, 155 kb, 156 kb, 157 kb, 158 kb, 159 kb, 160 kb, 161 kb, 162 kb, 163 kb, 164 kb, 165 kb, 166 kb, 167 kb, 168 kb, 169 kb, 170 kb, 171 kb, 172 kb, 173 kb, 174 kb, 175 kb, 176 kb, 177 kb, 178 kb, 179 kb, 180 kb, 181 kb, 182 kb, 183 kb, 184 kb, 185 kb, 186 kb, 187 kb, 188 kb, 189 kb, 190 kb, 191 kb, 192 kb, 193 kb, 194 kb, 195 kb, 196 kb, 197 kb, 198 kb, 199 kb, 200 kb, 201 kb, 202 kb, 203 kb, 204 kb, 205 kb, 206 kb, 207 kb, 208 kb, 209 kb, 210 kb, 211 kb, 212 kb, 213 kb, 214 kb, 215 kb, 216 kb, 217 kb, 218 kb, 219 kb, 220 kb, 221 kb, 222 kb, 223 kb, 224 kb, 225 kb, 226 kb, 227 kb, 228 kb, 229 kb, 230 kb, 231 kb, 232 kb, 233 kb, 234 kb, 235 kb, 236 kb, 237 kb, 238 kb, 239 kb, 240 kb, 241 kb, 242 kb, 243 kb, 244 kb, 245 kb, 246 kb, 247 kb, 248 kb, 249 kb, 50 kb, 51 kb, 252 kb, 253 kb, 254 kb, 255 kb, 256 kb, 257 kb, 258 kb, 259 kb, 260 kb, 261 kb, 262 kb, 263 kb, 264 kb, 265 kb, 266 kb, 267 kb, 268 kb, 269 kb, 270 kb, 271 kb, 272 kb, 273 kb, 274 kb, 275 kb, 276 kb, 277 kb, 278 kb, 279 kb, 280 kb, 281 kb, 282 kb, 283 kb, 284 kb, 285 kb, 286 kb, 287 kb, 288 kb, 289 kb, 290 kb, 291 kb, 292 kb, 293 kb, 294 kb, 295 kb, 296 kb, 297 kb, 298 kb, 299 kb, 300 kb, 301 kb, 302 kb, 303 kb, 304 kb, 305 kb, 306 kb, 307 kb, 308 kb, 309 kb, 310 kb, 311 kb, 312 kb, 313 kb, 314 kb, 315 kb, 316 kb, 317 kb, 318 kb, 319 kb, 320 kb, 321 kb, 322 kb, 323 kb, 324 kb, 325 kb, 326 kb, 327 kb, 328 kb, 329 kb, 330 kb, 331 kb, 332 kb, 333 kb, 334 kb, 335 kb, 336 kb, 337 kb, 338 kb, 339 kb, 340 kb, 341 kb, 342 kb, 343 kb, 344 kb, 345 kb, 346 kb, 347 kb, 348 kb, 349 kb, 350 kb, 351 kb, 352 kb, 353 kb, 354 kb, 355 kb, 356 kb, 357 kb, 358 kb, 359 kb, 360 kb, 361 kb, 362 kb, 363 kb, 364 kb, 365 kb, 366 kb, 367 kb, 368 kb, 369 kb, 370 kb, 371 kb, 372 kb, 373 kb, 374 kb, 375 kb, 376 kb, 377 kb, 378 kb, 379 kb, 380 kb, 381 kb, 382 kb, 383 kb, 384 kb, 385 kb, 386 kb, 387 kb, 388 kb, 389 kb, 390 kb, 391 kb, 392 kb, 393 kb, 394 kb, 395 kb, 396 kb, 397 kb, 398 kb, 399 kb, 400 kb or more genomic (e.g., nuclear or organelle) DNA. In some embodiments the captured and or modified large pieces of DNA may comprise about 10-400 kb, 50-350 kb, 100-300 kb, 100-200 kb, 200-300 kb, 150-200 kb, 200-250 kb genomic DNA In still other instances, the captured and or modified large pieces of DNA may comprise about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121,122, 123, 124, 125, 126, 127, 128, 129, 130, 131, 132, 133, 134, 135, 136, 137,138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230,231, 232, 233, 234, 235, 236, 237, 238, 239, 240, 241, 242, 243, 244, 245, 246, 247, 248, 249, 50, 51, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 or more open reading frames, partial open reading frames, pseudogenes and/or repeating sequences.

The present invention also provides vectors comprising a cassette-able chloroplast genome or portion thereof (e.g., a removable DNA fragment comprising a chloroplast genome or functional portion thereof). A vector of the present invention may comprise functional chloroplast units (e.g., a unit essential for metabolic processes, photosynthesis, gene expression, photosystem I, photosystem II). Vectors of the present invention may comprise a transplantable chloroplast genome or portion thereof. Additionally, the vectors of the present invention may comprise a transferable chloroplast genome or portion thereof. In other embodiments, the vectors comprise: 1) one or more large pieces of modified DNA; 2) all genes necessary to carry out photosynthesis; 3) all genes required for chloroplast survival and/or function; 4) essential chloroplast genes; and/or 5) sufficient naturally occurring or modified chloroplast genes to perform one or more chloroplast functions, such as photosynthesis. A vector may comprise a portion, substantially all, or all of the essential chloroplast genes. A vector may comprise at least 5, 10, 15, 20, 25, 30, 40, 50, 60, 70, 80, 90, 100 or more essential genes.

A vector may comprise chloroplast DNA of 10, 20, 30, 40, 50, 60, 70, 80, 90, 100, 110, 120, 130, 140, 150, 160, 170, 180, 190, 200, 210, 220, 230, 240, 250 kb or more in length. A vector may comprise essential chloroplast genes as well as non-essential chloroplast gene sequences. A vector may comprise one or more, or all, essential chloroplast genes and/or one or more genes not naturally occurring in a host cell comprising a vector. In some embodiments, a vector may comprise chloroplast genes and genes not naturally occurring in the chloroplast. A vector may comprise one or more essential chloroplast genes and/or one or more DNA sequences or genes involved in chloroplast function, photosynthesis, carbon fixation, and/or hydrocarbon production. For example, a vector may comprise a sequence required for photosynthesis and a sequence involved in the isoprenoid production, MVA, and/or MEP pathways, such as a DNA sequence encoding a terpene. synthase, or other polypeptide that produces a hydrocarbon, such as a terpene or isoprenoid. The invention further provides methods for cloning, manipulating and delivering a large target nucleic acid to a cell or particle, such as, for example, yeasts or bacteria. Certain embodiments of this method make use of a hybrid yeast-bacteria cloning system (See, e.g., U.S. Pat. Nos. 5,866,404 and 7,083,971 and Hokanson et al., (2003) Human Gene Ther.: 14: 329-339). The vectors herein (e.g., cloning system) is comprised of a shuttle vector that contains elements for function and replication in both yeast and bacteria, allowing it to stably function and replicate in either organism. This composition of functional and replicative elements yields a hybrid system which enjoys the benefits of both genetic engineering systems. The genetics of yeast (e.g., S. cerevisiae) are well understood and a powerful assortment of molecular biology tools exists for genetic engineering in yeast.

In another aspect the invention produces a gap-filled vector by homologous recombination among the two arms and the target nucleic acid. In still another embodiment, at least one arm further comprises an origin 6f replication. In another embodiment of the invention, each arm further comprises a rare restriction endonuclease recognition site. Homologous recombination may be performed in vitro or in vivo, for example, in a fungal cell (e.g., S. cerevisiae, Sz. pombe or U. maydis). The invention also provides a eukaryotic host cell harboring the recombinational cloning system or vector according to the invention, for example, in a fungal cell (e.g., S. cerevisiae, Sz. pombe or U maydis).

A gap-filled linear vector may be converted to a circular vector in vitro (e.g. using T4 ligase) or in vivo, for example, in a bacterium. The circular vectors of interest can be amplified, purified, cut and used to recover sufficient amounts of DNA to be introduced either directly into a cell or into a suitable delivery system for subsequent delivery to a target cell. The methodology offers great versatility to clone and to modify any large bacterial or non-bacterial genome, and easily facilitate the use thereof as recombinational vectors. Direct delivery of a gap-filled vector into a cell may be performed by methods well known in the field such as, for example, calcium phosphate transformation methodologies or electroporation (see Sambrook et al., supra).

Accordingly, the invention provides a method for producing a recombinant delivery unit including the steps of: (a) producing a gap-filled vector containing a target sequence; (b) optionally circularizing the gap-filled vector segments of the invention; (c) propagating the vector; and (d) introducing the gap-filled vector in a delivery unit.

Bacterial systems are useful for amplifying and purifying DNA, and for functionally testing the genetic modifications and their effect on pathways. One embodiment of the present invention provides cloning system will aid in the cloning and modifying of any large genome and easily facilitate the cloning and introduction of pathways. With the ability to deliver whole pathways, certain embodiments of the present invention allow for a system biological approach to problem solving.

In general, target DNA (e.g., genomic DNA) may be captured by creating sites allowing for homologous recombination in the vector. For example, such sites may be created by, but not limited to, gap-repair cloning, wherein a gap is created in the vector, usually by restrictive enzyme digestion prior to transformation into the yeast. When the target DNA is mixed with the vector, the target DNA is recombined into the vector. This operation is called "gap filling." This recombination can occur in bacteria, yeast, the original host organism, another organism, or in vitro. In some embodiments, recombination is performed in yeast because of the high rate of homologous recombination. Once captured, the target DNA can be modified in many ways including adding, altering, or removing DNA sequences. In some embodiments, the target DNA is genomic DNA. In other embodiments, the target DNA is organelle (e.g., mitochondria or chloroplast) DNA.

In some embodiments, target DNA is modified by adding, altering or removing genes, coding sequences, partial coding sequences, regulatory elements, positive and/or negative selection markers, recombination sites, restriction sites, and/or codon bias sites. For example, the target DNA sequence may be codon biased for expression in the organism being transformed. The skilled artisan is well aware of the "codon-bias" exhibited by a specific host cell in usage of nucleotide codons to specify a given amino acid. Without being bound by theory, by using a host cell's preferred codons, the rate of translation may be greater. Therefore, when synthesizing a gene for improved expression in a host cell, it may be desirable to design the gene such that its frequency of codon usage approaches the frequency of preferred codon usage of the host cell. The codons of the present invention may be A/T rich, for example, A/T rich in the third nucleotide position of the codons. typically, the A/T rich codon bias is used for algae. In some embodiments, at least 50% of the third nucleotide position of the codons are A or T. In other embodiments, at least 60%, 70%, 80%, 90%, or 99% of the third nucleotide position of the codons are A or T. (see also U.S. Publication No. 2004/0014174).

Such manipulations are well known in the art and can be performed in numerous ways. In some embodiments, the modifications may be performed using cloned sequences. In other embodiments, the modifications may be performed using synthetic DNA.

Genetic manipulations include cloning large pieces of target DNA (e.g., chromosomes, genomes) and/or dividing and reorganizing target DNA based on functional relations between genes, such as metabolic pathways or operons. Genetic manipulations also include introducing and removing metabolic pathways, recombining DNA into functional units (e.g., metabolic pathways, synthetic operons), and/or determining sites of instability in large pieces of DNA (e.g., sites where a native or non-native host tends to delete or recombine a sequence of DNA).

Target DNA may be DNA from a prokaryote. Target DNA may also be genomic DNA, mitochondrial DNA, or chloroplast DNA from a eukaryote. Examples of such organisms from which genomic and/or organelle DNA may serve as target DNA include, but are not limited to Z. mobilis, algae (e.g., macroalgae or microalgae, such as *Chlamydomonas reinhardtii*), a rhodophyte, a chlorophyte, a heterokontophyte, a tribophyte, a glaucophyte, a chlorarachniophyte, a euglenoid, a haptophyte, a cryptomonad, a dinoflagellum, or a phytoplankton. One of skill in the art will recognize that these organisms are listed only as examples and that the methods disclosed herein are applicable to the large DNA from any organism, including bacteria, plants, fungi, protists, and animals. Genetic manipulations of the present invention may include stabilizing large pieces of DNA by removing or inserting sequences that force transformed cells to preserve certain sequences of DNA and to stably maintain the sequences in its progeny. Genetic manipulations may also include altering codons of the target DNA, vector DNA, and/or synthetic DNA to reflect any codon bias of the host organism. Additionally, genetic manipulations of the present invention may include determining the minimal set of genes required for an organism to be viable. In another embodiment, the genetic manipulations of the present invention include determining the minimal set of genes required for a certain metabolic pathway to be created or maintained.

The genetic manipulations of the present invention may include determining redundant genes both within a genome, and between two genomes (e.g., redundancy between the nuclear and chloroplast genome). Additionally, the genetic manipulations of the present invention may include determining a fumctional sequence of DNA that could be artificially synthesized (e.g. the genes in a certain metabolic pathway, the genes of a functional genome). In another embodiment, the genetic manipulations of the present invention include creating DNA and genomes packaged into cassettes (e.g., sites within a vector where genes can be easily inserted or removed). The genetic manipulations of the present invention may also include creating a nuclear or organelle genome that is viable in multiple species (e.g. a transplantable chloroplast genome). Furthermore, the genetic manipulations of the present invention may include a method for testing the viability of any of these manipulations or creations (e.g., transferring a shuttle vector back into a host system and assaying for survival).

Vectors, Markers and Transformation

A vector or other recombinant nucleic acid molecule may include a nucleotide sequence encoding a selectable marker. The term or "selectable marker" or "selection marker" refers to a polynucleotide (or encoded polypeptide) that confers a detectable phenotype. A selectable marker generally encodes a detectable polypeptide, for example, a green fluorescent protein or an enzyme such as luciferase, which, when contacted with an appropriate agent (a particular wavelength of light or luciferin, respectively) generates a signal that can be detected by eye or using appropriate instrumentation (Giacomin, *Plant Sci.* 116:59-72, 1996; Scikantha, *J. Bacteriol.* 178:121, 1996; Gerdes, *FEBS Lett.* 389:44-47, 1996; see, also, Jefferson, *EMBO J.* 6:3901-3907, 1997, fl-glucuronidase). A selectable marker generally is a molecule that, when present or expressed in a cell, provides a selective advantage (or disadvantage) to the cell containing the marker, for example, the ability to grow in the presence of an agent that otherwise would kill the cell.

A selectable marker can provide a means to obtain prokaryotic cells or plant cells or both that express the marker and, therefore, can be useful as a component of a vector of the invention (see, for example, Bock, supra, 2001). Examples of selectable markers include, but are not limited to, those that confer antimetabolite resistance, for example, dihydrofolate reductase, which confers resistance to methotrexate (Reiss, *Plant Physiol.* (*Life Sci. Adv.*) 13:143-149, 1994); neomycin phosphotransferase, which confers resistance to the aminoglycosides neomycin, kanamycin and paromycin (Herrera-Estrella, *EMBO J.* 2:987-995, 1983), hygro, which confers resistance to hygromycin (Marsh, *Gene* 32:481-485, 1984), trpB, which allows cells to utilize indole in place of tryptophan; hisD, which allows cells to utilize histinol in place of histidine (Hartman, *Proc. Natl. Acad. Sci., USA* 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: Current Communications in Molecular Biology, Cold Spring Harbor Laboratory ed.); and deaminase from *Aspergillus terreus*, which confers resistance to Blasticidin S (Tamura, *Biosci. Biotechnol. Biochem.* 59:2336-2338, 1995). Additional selectable markers include those that confer herbicide resistance, for example, phosphinothricin acetyltransferase gene, which confers resistance to phosphinothricin (White et al., *Nucl. Acids Res.* 18:1062, 1990; Spencer et al., *Theor. Appl. Genet.* 79:625-631, 1990), a mutant EPSPV-synthase, which confers glyphosate resistance (Hinchee et al., *BioTechnology* 91:915-922, 1998), a mutant acetolactate synthase, which confers imidazolione or sulfonylurea resistance (Lee et al., *EMBO J.* 7:1241-1248, 1988), a mutant psbA, which confers resistance to atrazine (Smeda et al., *Plant Physiol.* 103:911-917, 1993), or a mutant protoporphyrinogen oxidase (see U.S. Pat. No. 5,767,373), or other markers conferring resistance to an herbicide such as glufosinate. Selectable markers include polynucleotides that confer dihydrofolate reductase (DHFR) or neomycin resistance for eukaryotic cells and tetracycline; ampicillin resistance for prokaryotes such as *E. coli*; and bleomycin, gentamycin, glyphosate, hygromycin, kanamycin, methotrexate, phleomycin, phosphinotricin, spectinomycin, streptomycin, sulfonamide and sulfonylurea resistance in plants (see, for example, Maliga et al., Methods in Plant Molecular Biology, Cold Spring Harbor Laboratory Press, 1995, page 39).

Methods for nuclear and plastid transformation are routine and well known for introducing a polynucleotide into a plant cell chloroplast (see U.S. Pat. Nos. 5,451,513, 5,545,817, and 5,545,818; WO 95/16783; McBride et al., *Proc. Natl. Acad. Sci., USA* 91:7301-7305, 1994). In some embodiments, chloroplast transformation involves introducing regions of chloroplast DNA flanking a desired nucleotide sequence, allowing for homologous recombination of the exogenous DNA into the target chloroplast genome. In some instances one to 1.5 kb flanking nucleotide sequences of chloroplast genomic DNA may be used. Using this method, point mutations in the chloroplast 16S rRNA and rps 12 genes, which confer resistance to spectinomycin and streptomycin, can be utilized as selectable markers for transformation (Svab et al., *Proc. Natl. Acad. Sci., USA* 87:8526-8530, 1990), and can result in stable homoplasmic transformants, at a frequency of approximately one per 100 bombardments of target leaves.

Microprojectile mediated transformation also can be used to introduce a polynucleotide into a plant cell chloroplast (Klein et al., *Nature* 327:70-73, 1987). This method utilizes microprojectiles such as gold or tungsten, which are coated with the desired polynucleotide by precipitation with calcium chloride, spermidine or polyethylene glycol. The microprojectile particles are accelerated at high speed into a plant tissue using a device such as the BIOLISTIC PD-1000 particle gun (BioRad; Hercules Calif.). Methods for the transformation using biolistic methods are well known in the art (see, e.g.; Christou, *Trends in Plant Science* 1:423-431, 1996). Microprojectile mediated transformation has been used, for example, to generate a variety of transgenic plant species, including cotton, tobacco, corn, hybrid poplar and papaya. Important cereal crops such as wheat, oat, barley, sorghum and rice also have been transformed using microprojectile mediated delivery (Duan et al., *Nature Biotech.* 14:494-498, 1996; Shimamoto, *Curr. Opin. Biotech.* 5:158-162, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, the glass bead agitation method, and the like.

Transformation frequency may be increased by replacement of recessive rRNA or r-protein antibiotic resistance genes with a dominant selectable marker, including, but not limited to the bacterial aadA gene (Svab and Maliga, *Proc. Natl. Acad. Sci., USA* 90:913-917, 1993). Approximately 15 to 20 cell division cycles following transformnation are generally required to reach a homoplastidic state. It is apparent to one of skill in the art that a chloroplast may contain multiple copies of its genome, and therefore, the term "homoplasmic" or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein.

Any of the nucleotide sequences of target DNA, vector DNA, or synthetic DNA on the vectors of the invention can further include codons biased for expression of the nucleotide sequences in the organism transformed. In some instances, codons in the nucleotide sequences are A/T rich in a third nucleotide position of the codons. For example, at least 50% of the third nucleotide position of the codons may be A or T. In other instances, the codons are G/C rich, for example at least 50% of the third nucleotide positions of the codons may be G or C.

The nucleotide sequences of the shuttle vectors of the present invention can be adapted for chloroplast expression. For example, a nucleotide sequence herein can comprise a chloroplast specific promoter or chloroplast specific regulatory control region. The nucleotide sequences can also be adapted for nuclear expression. For example, a nucleotide sequence can comprise a nuclear specific promoter or nuclear specific regulatory control regions. The nuclear sequences can encode a protein with a targeting sequence that encodes a chloroplast targeting protein (e.g., a chloroplast transit peptide), or a signal peptide that directs a protein to the endomembrane system for deposition in the endoplasmic reticulum or plasma membrane.

In embodiments where a vector encodes genes capable of fuel production, fuel products are produced by altering the enzymatic content of the cell to increase the biosynthesis of specific fuel molecules. For example, nucleotides sequences (e.g., an ORF isolated from an exogenous source) encoding biosynthetic enzymes can be introduced into the chloroplast of a photosynthetic organism. Nucleotide sequences encoding fuel biosynthetic enzymes can also be introduced into the nuclear genome of the photosynthetic organisms. Nucleotide sequences introduced into the nuclear genome can direct accumulation of the biosynthetic enzyme in the cytoplasm of the cell, or may direct accumulation of the biosynthetic enzyme in the chloroplast of the photosynthetic organism.

Any of the nucleotide sequences herein may further comprise a regulatory control sequence. Regulatory control sequences can include one or more of the following: a promoter, an intron, an exon, processing elements, 3' untranslated region, 5' untranslated region, RNA stability elements, or translational enhancers A promoter may be one or more of the following: a promoter adapted for expression in the organism, an algal promoter, a chloroplast promoter, and a nuclear promoter, any of which may be a native or synthetic promoters. A regulatory control sequence can be inducible or auto-regulatable. A regulatory control sequence can include autologous and/or heterologous sequences. In some cases, control sequences can be flanked by a first homologous sequence and a second homologous sequence. The first and second homologous sequences can each be at least 500 nucleotides in length. The homologous sequences can allow for either homologous recombination or can act to insulate the heterologous sequence to facilitate gene expression.

Vectors may also comprise sequences involved in producing products useful as biopharmaceuticals, such as, but not limited to, antibodies (including functional portions thereof), interleukins and other immune modulators, and antibiotics. See, e.g., Mayfield et al., (2003) *Proc. Nat'l Acad. Sci.:* 100 (438-42) and U.S. Pub. No. 2004/0014174.

Vectors of the present invention may comprise a cassette-able bacterial genome or portion thereof (e.g., a removable DNA fragment comprising a bacterial genome or functional portion thereof). Additionally, vectors of the present invention may comprise functional genomic units (e.g., a unit essential for metabolic processes, biochemical pathways, gene expression). Vectors of the present invention may comprise a transplantable bacterial genome or portion thereof. Vectors of the present invention may comprise a transferable bacterial genome or portion thereof.

In some embodiments, the large piece of target DNA is modified. The modified DNA may comprise all genes necessary to carry out ethanologenesis, all genes required for the Entner-Duodorff pathway, the glucose tolerance pathway, the ethanol tolerance pathway, the carboxylic acid byproduct resistance pathway, the acetic acid tolerance pathway, the sugar transport pathway, sugar fermentation pathways, and/or the cellulose and hemicellulose digestive pathways. Hybrid cloning systems and methods of the invention combine the high versatility of yeast as a system for the capture and manipulation of a given nucleic acid and the high efficiency of bacterial systems for the amplification of such nucleic acid. Recombinational vectors relying on homologous recombination to mediate the isolation, manipulation and delivery of large nucleic acid fragments were constructed. The invention described herein also provides methods for using such recombinational cloning vectors to clone, to manipulate and to deliver large nucleic acids. Finally, the invention provides methods for using such recombinational cloning systems as potentiators of biochemical pathway analysis, organelle analysis, and synthetic chloroplast construction.

The vectors of the present invention may be introduced into yeast. The yeast may be a suitable strain of *Saccharomyces cerevisiae*; however, other yeast models may be utilized. Introduction of vectors into yeast may allow for genetic manipulation of the vectors. Yeast vectors have been described extensively in the literature and methods of manipulating the same also are well known as discussed hereinafter (see e.g., Ketner et al. (1994) *Proc. Natl. Acad. Sci. (USA)* 91:6186 6190).

Following genetic manipulation, the cloning system may allow for the transition to a bacterial environment, suitable for the preparation of larger quantities of nucleic acids. Representative examples of a bacterial type vectors include, but are not limited to, the P1 artificial chromosome, bacterial artificial chromosome (BAC) and single copy plasmid F factors (Shizuya et al. (1992) *Proc. Natl. Acad. Sci.* 89:8794 8797). Similarly, bacterial vectors are well known in the art (e.g., Ioannou et al. (1994) *Nature* 6:84 89). The invention also provides a shuttle vector comprising a yeast selectable marker, a bacterial selectable marker, a telomere, a centromere, a yeast origin of replication, and/or a bacterial origin of replication.

Shuttle vectors of the present invention may enable homologous recombination in yeast to capture and to integrate in a vector of interest a target nucleic acid of interest. Shuttle vectors may allow for the manipulation of target DNA in any of the hosts to which the vectors can be introduced. In some embodiments, after desired manipulations, shuttle vector components may be removed, leaving just the modified target DNA. Such extraction of vector sequences can be performed using standard methodologies and may occur in any host cell. The target nucleic acid of interest can be a large nucleic acid, and can include, for example, a vector, such as a viral vector, including the foreign gene of interest contained therein. The target nucleic acid can also be a bacterial (including archaebacteria and eubacteria), viral, fungal, protist, plant or animal genome, or a portion thereof. For example, the target nucleic acid of one embodiment of the present invention comprises an entire prokaryotic genome. As an additional example, a target nucleic acid of the present invention may comprises the chloroplast genome of a eukaryotic organism.

Shuttle vectors according to the invention may comprise an appropriately oriented DNA that functions as a telomere in yeast and a centromere. Any suitable telomere may be used. Suitable telomeres include without limitation telomeric repeats from many organisms, which can provide telomeric finction in yeast. The terminal repeat sequence in humans $(TTAGGG)_N$, is identical to that in trypanosomes and similar to that in yeast $((TG)_{1-3})_N$ and Tetrahymena $(TTGGG)_N$ (Szostak & Blackburn (1982) *Cell* 29:245 255; Brown (1988) *EMBO J.* 7:2377 2385; and Moyzis et al. (1988) *Proc. Natl. Acad. Sci.* 85:6622 6626).

The term "centromere" is used herein to identify a nucleic acid, which mediates the stable replication and precise partitioning of the vectors of the invention at meiosis and at mitosis thereby ensuring proper segregation into daughter cells. Suitable centromeres include, without limitation, the yeast centromere, CEN4, which confers mitotic and meiotic stability on large linear plasmids (Murray & Szostak (1983) *Nature* 305:189 193; Carbon (1984) *Cell* 37:351 353; and Clark et al. (1990) *Nature* 287:504 509)).

In some embodiments, at least one of the two segments of the circular vector according to the invention includes at least one replication system that is finctional in a host cell/particle of choice. As it will become apparent hereinafter, one of skill will realize that the manipulation, amplification and/or delivery of a target nucleic acid of choice may entail the use of more than one host cell/particle. Accordingly, more than one replication system functional in each host cell/particle of choice may be included.

When a host cell(s) is a prokaryote, particularly *E. coli*, replication system(s) include those which are functional in prokaryotes, such as, for example, P1 plasmid replicon, ori, P1 lytic replicon, ColE1, BAC, single copy plasmid F factors and the like. Either one or both segments, and/or the circular vector, may further include a yeast origin of replication capable of supporting the replication of large nucleic acids. Non-limiting examples of replication regions according to the invention include the autonomously replicating sequence or "ARS element." ARS elements were identified as yeast sequences that conferred high-frequency transformation. *Tetrahymena* DNA termini have been used as ARS elements in yeast along with ARS1 and ARS4 (Kiss et al. (1981)*Mol. Cell Biol.* 1:535 543; Stinchcomb et al. (1979) *Nature* 282:39; and Barton & Smith (1986) *Mol. Cell Biol.* 6:2354). For each segment (e.g., those corresponding to the yeast and bacterial elements of the gap-filling shuttle vector) there may be two or more origins of replication.

The first and/or the second segment according to an aspect of the invention may be joined in a circularized vector form (e.g., plasmid form). Circularization can occur in vivo or in vitro using the segment of interest. Alternatively, a circular vector of interest can be used. As used herein, the term "vector" designates a plasmid or phage DNA or other nucleic acid into which DNA or other nucleic acid may be cloned. The vector may replicate autonomously in a host cell and may be characterized further by one or a small number of restriction endonuclease recognition sites at which such nucleic acids may be cut in a determinable fashion and into which nucleic acid fragments may be inserted. The vector further may contain a selectable marker suitable for the identification of cells transformed with the vector.

Target nucleic acids of the invention may vary considerably in complexity. The target nucleic acid may include viral, prokaryotic or eukaryotic DNA, cDNA, exonic (coding), and/or intronic (noncoding) sequences. Hence, the target nucleic acid of the invention may include one or more genes. A target nucleic acid may be a chromosome, genome, or operon and/or a portion of a chromosome, genome or operon. A target nucleic acid may comprise coding sequences for all the genes in a pathway, the minimum complement of genes necessary for survival of an organelle, and/or the minimum complement of genes necessary for survival of an organism. A target nucleic acid may comprise *Zymomonas mobilis* DNA sequence, including, but not limited to genomic DNA and/or cDNA. A target nucleic acid may comprise eukaryotic chloroplast DNA sequence, including but not limited to, chloroplast genome DNA and/or cDNA. A target nucleic acid may comprise cyanobacteria DNA, including but not limited to genomic DNA and/or cDNA. The target nucleic acid also may be of any origin and/or nature.

It may be desirable for the gene to also comprise a promoter operably linked to the coding sequence in order to effectively promote transcription. Enhancers, repressors and other regulatory sequences may also be included in order to modulate activity of the gene, as is well known in the art. A gene as provided herein can refer to a gene that is found in the genome of the individual host cell (i.e., endogenous) or to a gene that is not found in the genome of the individual host cell (i.e., exogenous or a "foreign gene"). Foreign genes may be from the same species as the host or from different species. For transfection of a cell using DNA containing a gene with the intent that the gene will be expressed in the cell, the DNA may contain any control sequences necessary for expression of the gene in the required orientation for expression. The term "intron" as used herein, refers to a DNA sequence present in a given gene which is not translated into protein and is generally found between exons.

Genetic elements, or polynucleotides comprising a region that encodes a polypeptide or a region that regulates transcription or translation or other processes important to expression of the polypeptide in a host cell, or a polynucleotide comprising both a region that encodes a polypeptide and a region operably linked thereto that regulates expression. Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

Vectors of the present invention may contain sufficient linear identity or similarity (homology) to have the ability to hybridize to a portion of a target nucleic acid made or which is single-stranded, such as a gene, a transcriptional control element or intragenic DNA. Without being bound to theory, such hybridization is ordinarily the result of base-specific hydrogen bonding between complementary strands, preferably to form Watson-Crick base pairs. As a practical matter, such homology can be inferred from the observation of a homologous recombination event. In some embodiments, such homology is from about 8 to about 1000 bases of the linear nucleic acid. In other embodiments, such homology is from about 12 to about 500 bases. One skilled in the art will appreciate that homology may extend over longer stretches of nucleic acids.

Homologous recombination is a type of genetic recombination, a process of physical rearrangement occurring between two strands of DNA. Homologous recombination involves the alignment of similar sequences, a crossover between the aligned DNA strands, and breaking and repair of the DNA to produce an exchange of material between the strands. The process homologous recombination naturally occurs in organisms and is also utilized as a molecular biology technique for introducing genetic changes into organism.

The vectors of the invention may be modified further to include functional entities other than the target sequence which may find use in the preparation of the construct(s), amplification, transformation or transfection of a host cell, and—if applicable—for integration in a host cell. For example, the vector may comprise regions for integration into host DNA. Integration may be into nuclear DNA of a host cell. In some embodiments, integration may be into non-nuclear DNA, such as chloroplast DNA. Other functional entities of the vectors may include, but are not limited to, markers, linkers and restriction sites.

A target nucleic acid may include a regulatory nucleic acid. This refers to any sequence or nucleic acid which modulates (either directly or indirectly, and either up or down) the replication, transcription and/or expression of a nucleic acid controlled thereby. Control by such regulatory nucleic acid may make a nucleic acid constitutively or inducibly transcribed and/or translated. Any of the nucleotide sequences herein may further comprise a regulatory control sequence. Examples of regulatory control sequences can include, without limitation, one or more of the following: a promoter, an intron, an exon, processing elements, 3' untranslated region, 5' untranslated region, RNA stability elements, or translational enhancers. A promoter may be one or more of the following: a promoter adapted for expression in the organism (e.g., bacterial, fungal, viral, plant, mammalian, or protist), an algal promoter, a chloroplast (or other plastid) promoter, a mitochondrial promoter, and a nuclear promoter, any of which may be a native or synthetic promoters. A regulatory control sequence can be inducible or autoregulatable. A regulatory control sequence can include autologous and/or heterologous sequences. In some cases, control sequences can be flanked by a first homologous sequence and a second homologous sequence. The first and second homologous sequences can each be at least 500 nucleotides in length. The homologous sequences can allow for either homologous recombination or can act to insulate the heterologous sequence to facilitate gene expression.

In some instances, target DNA, vector DNA or other DNA present in a shuttle vector of the present invention does not result in production of a polypeptide product but rather allows for secretion of the product from the cell. In these cases, the nucleotide sequence may encode a protein that enhances or initiates or increases the rate of secretion of a product from an organism to the external environment. Thus, segments of vectors and/or vectors of the invention may include a transcriptional regulatory region such as, for example, a transcriptional initiation region. One skilled in the art will appreciate that a multitude of transcriptional initiation sequences have been isolated and are available, including thymidine kinase promoters, beta-actin promoters, immunoglobin promoters, methallothionein promoters, human cytomegalovirus promoters and SV40 promoters.

One embodiment of the invention provides a method of producing a gap-filled vector. A gap-filled vector may undergo homologous recombination and insertion of a target nucleic acid according to the invention by filling in the region (gap) between the sequences homologous to the 5' and the 3' regions of the target nucleic acid. Hence, in some embodiments, one would contact the instant cloning system with a target nucleic acid under conditions that allow homologous recombination.

Another method combines: (i) a first segment including a first nucleic acid homologous to the 5' terminus of a target nucleic acid, a first selectable marker and a first cyclization element; (ii) a target nucleic acid; and (iii) a second segment including a second nucleic acid homologous to the 3' terminus of a target nucleic acid, a second selectable marker and a second cyclization element, under conditions which allow homologous recombination. One embodiment of the invention produces a gap-filled vector by homologous recombination between the two arms and the target nucleic acid. The exchange between the homologous regions found in the arms and the target nucleic acid is effected by homologous recombination at any point between the homologous nucleic acids. With respect to a circular vector of the present invention, the "gap filling" essentially is insertion (i.e., subcloning) of the target sequence into the vector.

Homologous recombination may be effected in vitro according to methodologies well known in the art. For example, the method of the invention can be practiced using yeast lysate preparations. Homologous recombination may take place in vivo. Hence, the method of the invention may be practiced using any host cell capable of supporting homologous recombination events such as, for example, bacteria, yeast and mammalian cells. One skilled in the art will appreciate that the choice of a suitable host depends on the particular combination of selectable markers used in the cloning system of the method.

Techniques that may be used to introduce the vector into a host cell of interest include calcium phosphate/DNA coprecipitation, electroporation, bacterial-protoplast fusion, microinjection of DNA into the nucleus and so on. One of skill will appreciate that a number of protocols may be used virtually interchangeably, for example, to transfect mammalian cells, as set forth for example in Keown et al. (Meth. Enzymol. 185:527 537, 1990).

Transformation may be achieved by using a soil bacterium, such as *Agrobacterium tumefaciens*. *Agrobacterium tumefaciens* may carry an engineered plasmid vector, or carrier of selected extra genes. Plant tissue, such as leaves, are cut in small pieces, eg. 10×10 mm, and soaked for 10 minutes in a fluid containing suspended *Agrobacterium*. Some cells along the cut is transformed by the bacterium, that inserts its DNA into the cell. Placed on selectable rooting and shooting media, the plants will regrow. Some plants species can be transformed just by dipping the flowers into suspension of *Agrobacteria* and then planting the seeds in a selective medium.

Another methodology is use of a "gene gun" approach. The gene gun is part of a method called the biolistic (also known as bioballistic) method, and under certain conditions, DNA (or RNA) become "sticky," adhering to biologically inert particles such as metal atoms (usually tungsten or gold). By accelerating this DNA-particle complex in a partial vacuum and placing the target tissue within the acceleration path, DNA is effectively introduced. Uncoated metal particles could also be shot through a solution containing DNA surrounding the cell thus picking up the genetic material and proceeding into the living cell. A perforated plate stops the shell cartridge but allows the slivers of metal to pass through and into the living cells on the other side. The cells that take up the desired DNA, identified through the use of a marker gene (in plants the use of GUS is most common), are then cultured to replicate the gene and possibly cloned. The biolistic method is most useful for inserting genes into plant cells such as pesticide or herbicide resistance. Different methods have been used to accelerate the particles: these include pneumatic devices; instruments utilizing a mechanical impulse or macroprojectile; centripetal, magnetic or electrostatic forces; spray or vaccination guns; and apparatus based on acceleration by shock wave, such as electric discharge (for example, see Christou and McCabe, 1992, Agracetus, Inc. Particle Gun Transformation of Crop Plants Using Electric Discharge (ACCELL™ Technology)).

Transformation can be performed, for example, according to the method of Cohen et al. (Proc. Natl. Acad. Sci. USA, 69:2110 (1972)), the protoplast method (Mol. Gen. Genet., 168:111 (1979)), or the competent method (J. Mol. Biol., 56:209 (1971)) when the hosts are bacteria (*E. coli, Bacillus subtilis*, and such), the method of Hinnen et al. (Proc. Natl. Acad. Sci. USA, 75:1927 (1978)), or the lithium method (J. Bacteriol., 153:163 (1983)) when the host is *S. cerevisiae*, the method of Graham (Virology, 52:456 (1973)) when the hosts are animal cells, and the method of Summers et al. (Mol. Cell. Biol., 3:2156-2165 (1983)) when the hosts are insect cells.

Typically, following a transformation event, potential transformants are plated on nutrient media for selection and/or cultivation.

The nutrient media preferably comprises a carbon source, an inorganic nitrogen source, or an organic nitrogen source necessary for the growth of host cells (transformants). Examples of the carbon source are glucose, dextran, soluble starch, and sucrose, and examples of the inorganic or organic nitrogen source are ammonium salts, nitrates, amino acids, corn steep liquor, peptone, casein, meat extract, soy bean cake, and potato extract. If desired, the media may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, etc.). Media for some photosynthetic organisms may not require a carbon source as such organisms may be photoautotrophs and, thus, can produce their own carbon sources.

Cultivation and/or selection are performed by methods known in the art. Cultivation and selection conditions such as temperature, pH of the media, and cultivation time are selected appropriately for the vectors, host cells and methods of the present invention. One of skill in the art will recognize that there are numerous specific media and cultivation/selection conditions which can be used depending on the type of host cell (transformant) and the nature of the vector (e.g., which selectable markers are present). The media herein are merely described by way of example and are not limiting.

When the hosts are bacteria, actinomycetes, yeast, or filamentous fungi, media comprising the nutrient source(s) mentioned above are appropriate. When the host is *E. coli*, examples of preferable media are LB media, M9 media (Miller et al. Exp. Mol. Genet., Cold Spring Harbor Laboratory, p.431 (1972)), and so on. When the host is yeast, an example of medium is Burkhoter minimal medium (Bostian, *Proc. Natl. Acad Sci. USA*, 77:4505 (1980)).

The selection of vectors in yeast may be accomplished by the use of yeast selectable markers. Examples include, but are not limited to, HIS3, TRP1, URA3, LEU2 and ADE markers. In some embodiments of the invention, a vector or segment thereof may comprise two or more selectable markers. Thus, in one embodiment, a segment of a vector of the present invention may comprise an ADE marker to be lost upon homologous recombination with the target nucleic acid, and a HIS3 marker. The other segment may comprise a TRP1 marker. Selection is achieved by growing transformed cells on a suitable drop-out selection media (see e.g., Watson et al. (1992) Recombinant DNA, 2.sup.nd ed., Freeman and Co., New York, N.Y.). For example, HIS3 allows for selection of cells containing the first segment. TRP1 allows for selection of cells containing the second segment. ADE allows screening and selection of clones in which homologous recombination took place. ADE enables color selection (red).

Recombinant yeast cells may be selected using the selectable markers described herein according to methods well known in the art. Hence, one skilled in the art will appreciate that recombinant yeast cells harboring a gap-filled vector of the invention may be selected on the basis of the selectable markers included therein. For example, recombinant vectors carrying HIS3 and TRP1 may be selected by growing transformed yeast cells in the presence of drop-out selection media lacking histidine and tryptophan. Isolated positive clones may be purified further and analyzed to ascertain the presence and structure of the recombinant vector of the invention by, e.g., restriction analysis, electrophoresis, Southern blot analysis, polymerase chain reaction or the like. The invention further provides gap-filled vectors engineered according to the method of the invention. Such a vector is the product of homologous recombination between the segments or vectors of the invention and a target nucleic acid of choice. The invention also provides a prokaryotic cell and/or a eukaryotic host cell harboring the cloning system or vector according to the invention. The organism can be unicellular or multicellular. The organism may be naturally photosynthetic or naturally non-photosynthetic. Other examples of organisms that can be transformed include vascular and non-vascular organisms. When hosts, such as plant, yeast, animal, algal, or insect cells are used, a vector of the present invention may contain, at least, a promoter, an initiation codon, the polynucleotide encoding a protein, and a termination codon. The vectors of the present invention may also contain, if required, a polynucleotide for gene amplification (marker) that is usually used.

Products

The vectors of the present invention may comprise sequences that result in production of a product naturally, or not naturally, produced in the organism comprising the vector. In some instances the product encoded by one or more sequences on a vector is a polypeptide, for example an enzyme. Enzymes utilized in practicing the present invention may be encoded by nucleotide sequences derived from any organism, including bacteria, plants, fungi and animals. Vectors may also comprise nucleotide sequences that affect the production or secretion of a product from the organism. In some instances, such nucleotide sequence(s) encode one or more enzymes that function in isoprenoid biosynthetic pathway. Examples of polypeptides in the isoprenoid biosynthetic pathway include synthases such as C5, C10, C15, C20, C30, and C40 synthases. In some instances, the enzymes are isoprenoid producing enzymes. In some instances, an isoprenoid producing enzyme produces isoprenoids with two phosphate groups (e.g., GPP synthase, FPP synthase, DMAPP synthase). In other instances, isoprenoid producing enzymes produce isoprenoids with zero, one, three or more phosphates or may produce isoprenoids with other functional groups. Polynucleotides encoding enzymes and other proteins useful in the present invention may be isolated and/or synthesized by any means known in the art, including, but not limited to cloning, sub-cloning, and PCR.

An isoprenoid producing enzyme for use in the present invention may also be botryococcene synthase, β-caryophyllene synthase, germacrene A synthase, 8-epicedrol synthase, valencene synthase, (+)-δ-cadinene synthase, germacrene C synthase, (E)-β-farnesene synthase, casbene synthase, vetispiradiene synthase, 5-epi-aristolochene synthase, aristolchene synthase, α-humulene, (E,E)-α-farnesene synthase, (−)-β-pinene synthase, γ-terpinene synthase, limonene cyclase, linalool synthase, (+)-bornyl diphosphate synthase, levopimaradiene synthase, isopimaradiene synthase, (E)-γ-bisabolene synthase, copalyl pyrophosphate synthase, kaurene synthase, longifolene synthase, γ-humulene synthase, δ-selinene synthase, β-phellandrene synthase, terpinolene synthase, (+)-3-carene synthase, syn-copalyl diphosphate synthase, α-terpineol synthase, syn-pimara-7,15-diene synthase, ent-sandaaracopimaradiene synthase, sterner-13-ene synthase, E-β-ocimene, S-linalool synthase, geraniol synthase, γ-terpinene synthase, linalool synthase, E-β-ocimene synthase, epi-cedrol synthase, α-zingiberene synthase, guaiadiene synthase, cascarilladiene synthase, cis-muuroladiene synthase, aphidicolan-16b-ol synthase, elizabethatriene synthase, sandalol synthase, patchoulol synthase, zinzanol synthase, cedrol synthase, scareol synthase, copalol synthase, or manool synthase.

Other enzymes which may be produced by vectors of the present invention include biomass-degrading enzymes. Non-limiting examples of biomass-degrading enzymes include: cellulolytic enzymes, hemicellulolytic enzymes, pectinolytic enzymes, xylanases, ligninolytic enzymes, cellulases, cellobiases, softening enzymes (e.g., endopolygalacturonase), amylases, lipases, proteases, RNAses, DNAses, inulinase, lysing enzymes, phospholipases, pectinase, pullulanase, glucose isomerase, endoxylanase, beta-xylosidase, alpha-L-arabinofuranosidase, alpha-glucoronidase, alpha-galactosidase, acetylxylan esterase, and feruloyl esterase. Examples of genes that encode such enzymes include, but are not limited to, amylases, cellulases, hemicellulases, (e.g., β-glucosidase, endocellulase, exocellulase), exo-β-glucanase, endo-β-glucanase and xylanse (endoxylanase and exoxylanse). Examples of ligninolytic enzymes include, but are not limited to, lignin peroxidase and manganese peroxidase from *Phanerochaete chryososporium*. One of skill in the art will recognize that these enzymes are only a partial list of enzymes which could be used in the present invention.

The present invention contemplates making enzymes that contribute to the production of fatty acids, lipids or oils by transforming host cells (e.g., alga cells such as *C. reinhardtii, D. salina, H. pluvalis* and cyanobacterial cells) and/or organisms comprising host cells with nucleic acids encoding one or more different enzymes. In some embodiments the enzymes that contribute to the production of fatty acids, lipids or oils are anabolic enzymes. Some examples of anabolic enzymes that contribute to the synthesis of fatty acids include, but are not limited to, acetyl-CoA carboxylase, ketoreductase, thioesterase, malonyltransferase, dehydratase, acyl-CoA ligase, ketoacylsynthase, enoylreductase and a desaturase. In some embodiments the enzymes are catabolic or biodegrading enzymes. In some embodiments, a single enzyme is produced.

Some host cells may be transformed with multiple genes encoding one or more enzymes. For example, a single transformed cell may contain exogenous nucleic acids encoding enzymes that make up an entire fatty acid synthesis pathway. One example of a pathway might include genes encoding an acetyl CoA carboxylase, a malonyltransferase, a ketoacylsynthase, and a thioesterase. Cells transformed with entire pathways and/or enzymes extracted from them, can synthesize complete fatty acids or intermediates of the fatty acid synthesis pathway. In some embodiments constructs may contain multiple copies of the same gene, and/or multiple genes encoding the same enzyme from different organisms, and/or multiple genes with mutations in one or more parts of the coding sequences.

In some instances, a product (e.g. fuel, fragrance, insecticide) is a hydrocarbon-rich molecule, e.g. a terpene. A terpene (classified by the number of isoprene units) can be a hemiterpene, monoterpene, sesquiterpene, diterpene, triterpene, or tetraterpene. In specific embodiments the terpene is a terpenoid (aka isoprenoid), such as a steroid or carotenoid. Subclasses of carotenoids include carotenes and xanthophylls. In specific embodiments, a fuel product is limonene, 1, 8-cineole, α-pinene, camphene, (+)-sabinene, myrcene, abietadiene, taxadiene, famesyl pyrophosphate, amorphadiene, (E)-α-bisabolene, beta carotene, alpha carotene, lycopene, or diapophytoene. Some of these terpenes are pure hydrocarbons (e.g. limonene) and others are hydrocarbon derivatives (e.g. cineole).

Examples of fuel products include petrochemical products and their precursors and all other substances that may be useful in the petrochemical industry. Fuel products include, for example, petroleum products, and precursors of petroleum, as well as petrochemicals and precursors thereof. The fuel product may be used for generating substances, or materials, useful in the petrochemical industry, including petroleum products and petrochemicals. The fuel or fuel products may be used in a combustor such as a boiler, kiln, dryer or furnace. Other examples of combustors are internal combustion engines such as vehicle engines or generators, including gasoline engines, diesel engines, jet engines, and others. Fuel products may also be used to produce plastics, resins, fibers, elastomers, lubricants, and gels.

Examples of products contemplated herein include hydrocarbon products and hydrocarbon derivative products. A hydrocarbon product is one that consists of only hydrogen molecules and carbon molecules. A hydrocarbon derivative product is a hydrocarbon product with one or more heteroatoms, wherein the heteroatom is any atom that is not hydrogen or carbon. Examples of heteroatoms include, but not limited to, nitrogen, oxygen, sulfur, and phosphorus. Some products are hydrocarbon-rich, wherein as least 50%, 60%, 70%, 80%, 90%, or 95% of the product by weight is made up carbon and hydrogen.

Fuel products, such as hydrocarbons, may be precursors or products conventionally derived from crude oil, or petroleum, such as, but not limited to, liquid petroleum gas, naptha (ligroin), gasoline, kerosene, diesel, lubricating oil, heavy gas, coke, asphalt, tar, and waxes. For example, fuel products may include small alkanes (for example, 1 to approximately 4 carbons) such as methane, ethane, propane, or butane, which may be used for heating (such as in cooking) or making plastics. Fuel products may also include molecules with a carbon backbone of approximately 5 to approximately 9 carbon atoms, such as naptha or ligroin, or their precursors. Other fuel products may be about 5 to about 12 carbon atoms or cycloalkanes used as gasoline or motor fuel. Molecules and aromatics of approximately 10 to approximately 18 carbons, such as kerosene, or its precursors, may also be fuel products. Fuel products may also include molecules, or their precursors, with more than 12 carbons, such as used for lubricating oil. Other fuel products include heavy gas or fuel oil, or their precursors, typically containing alkanes, cycloalkanes, and aromatics of approximately 20 to approximately 70 carbons. Fuel products also includes other residuals from crude oil, such as coke, asphalt, tar, and waxes, generally containing multiple rings with about 70 or more carbons, and their precursors.

Host Cells and Organisms

Examples of organisms that can be transformed using the vectors and methods herein include vascular and non-vascular organisms. The organism can be prokaroytic or eukaroytic. The organism can be unicellular or multicellular.

Eukaryotic cells, such as a fungal cell (e.g., *Saccharomyces cerevisiae, Schizosaccharomyces pombe* or *Ustilago maydis*) may be transformed using the methods and compositions of the present invention. Methods for introducing nucleic acids in a fungal/yeast cells are well known in the art. Hence, such a step may be accomplished by conventional transformation methodologies. Non-limiting examples of suitable methodologies include electroporation, alkali cations protocols and spheroplast transformation.

Examples of non-vascular photosynthetic organisms include bryophtyes, such as marchantiophytes or anthocerotophytes. In some instances the organism is a cyanobacteria. In some instances, the organism is algae (e.g., macroalgae or microalgae). The algae can be unicellular or multicellular algae. In some instances the organism is a rhodophyte, chlorophyte, heterokontophyte, tribophyte, glaucophyte, chlorarachniophyte, euglenoid, haptophyte, cryptomonad, dinoflagellur, or phytoplankton.

The methods of the present invention are exemplified using the microalga, *C. reinhardtii*. The use of microalgae to express a polypeptide or protein complex according to a method of the invention provides the advantage that large populations of the microalgae can be grown, including commercially (Cyanotech Corp.; Kailua-Kona Hi.), thus allowing for production and, if desired, isolation of large amounts of a desired product. However, the ability to express, for example, functional polypeptides, including protein complexes, in the chloroplasts of any plant and/or modifiy the chloroplasts or any plant allows for production of crops of such plants and, therefore, the ability to conveniently produce large amounts of the polypeptides. Accordingly, the methods of the invention can be practiced using any plant having chloroplasts, including, for example, macroalgae, for example, marine algae and seaweeds, as well as plants that grow in soil, for example, com (*Zea mays*), *Brassica* sp. (e.g., *B. napus, B. rapa, B. juncea*), particularly those *Brassica* species usefuil as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea ultilane*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugar cane (*Saccharum* spp.), oats, duckweed (*Lemna*), barley, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C melo*). Ornamentals such as azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum are also included. Additional ornamentals useful for practicing a method of the invention include impatiens, Begonia, Pelargonium, Viola, Cyclamen, Verbena, Vinca, Tagetes, Primula, Saint Paulia, Agertum, Amaranthus, Antihirrhinum, Aquilegia, Cineraria, Clover, Cosmo, Cowpea, Dahlia, Datura, Delphinium, Gerbera, Gladiolus, Gloxinia, Hippeastrum, Mesembryanthemum, Salpiglossos, and Zinnia. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga ultilane*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Leguminous plants useful for practicing a method of the invention include beans and peas. Beans include guar, locust bean, fenugreek, soybean, garden beans, cowpea, mung bean, lima bean, fava bean, lentils, chickpea, etc. Legumes include, but are not limited to, *Arachis*, e.g., peanuts, *Vicia*, e.g., crown vetch, hairy vetch, adzuki bean, mung bean, and chickpea, *Lupinus*, e.g., lupine, trifolium, *Phaseolus*, e.g., common bean and lima bean, *Pisum*, e.g., field bean, *Melilotus*, e.g., clover, *Medicago*, e.g., alfalfa, *Lotus*, e.g., trefoil, lens, e.g., lentil, and false indigo. Preferred forage and turf grass for use in the methods of the invention include alfalfa, orchard grass, tall fescue, perennial ryegrass, creeping bent grass, and redtop. Other plants useful in the invention include Acacia, aneth, artichoke, arugula, blackberry, canola, cilantro, clementines, escarole, eucalyptus, fennel, grapefruit, honey dew, jicama, kiwifruit, lemon, lime, mushroom, nut, okra, orange, parsley, persimmon, plantain, pomegranate, poplar, radiata pine, radicchio, Southern pine, sweetgum, tangerine, triticale, vine, yams, apple, pear, quince, cherry, apricot, melon, hemp, buckwheat, grape, raspberry, chenopodium, blueberry, nectarine, peach, plum, strawberry, watermelon, eggplant, pepper, cauliflower, *Brassica*, e.g., broccoli, cabbage, ultilan sprouts, onion, carrot, leek, beet, broad bean, celery, radish, pumpkin, endive, gourd, garlic, snapbean, spinach, squash, turnip, ultilane, chicory, groundnut and zucchini. Thus, the compositions contemplated herein include host organisms comprising any of the above nucleic acids. The host organism can be any chloroplast-containing organism.

The term "plant" is used broadly herein to refer to a eukaryotic organism containing plastids, particularly chloroplasts, and includes any such organism at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or a cultured cell, or can be part of higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like.

Eukaryotic host cells may be a fungal cell (e.g., *S. cerevisiae*, *Sz. pombe* or *U. maydis*). Examples of prokaryotic host cells include *E. coli* and *B. subtilis*, cyanobacteria and photosynthetic bacteria (e.g. species of the genus *Synechocystis* or the genus *Synechococcus* or the genus *Athrospira*). Examples of non-vascular plants which may be a host organism (or the source of target DNA) include bryophtyes, such as marchantiophytes or anthocerotophytes. In some instances, the organism is algae (e.g., macroalgae or microalgae, such as *Chlamydomonas reinhardtii, Chorella vulgaris, Dunaliella salina, Haematococcus pluvalis, Scenedesmus* ssp.). The algae can be unicellular or multicellular algae. In some instances the organism is a rhodophyte, chlorophyte, heterokontophyte, tribophyte, glaucophyte, chlorarachniophyte, euglenoid, haptophyte, cryptomonad, dinoflagellum, or phytoplankton. In other instancesOne of skill in the art will recognize that these organisms are given merely as examples and other organisms may be substituted where appropriate positive and negative selectable markers are available.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

EXAMPLES

Example 1

DNA Purification and Analysis

DNA is isolated and analyzed according to methods known in the art.

To prepare DNA from *Chlamydomonas reinhardtii* to use as a template for PCR, $10^6$ algae cells (from agar plate or liquid culture) are suspended in 10 mnM EDTA and heated to 95° C. for 10 minutes, then cooled to near 23° C. The solution is added to the PCR mixture directly.

To prepare purified chloroplast DNA from *Chlamydomonas reinhardtii*, $5 \times 10^8$ algae cells are collected from liquid culture by centrifagation at 3000×g for 10 min, washed once with water, centrifuged at 3000×g for 10 min, resuspended in 10 mL of lysis solution (10 mM Tris pH=8.0, 10 mM EDTA, 150 mM NaCl, 2% SDS, 2% Sarkosyl, and 25 ug/mL Pronase (Roche)), and incubated at 37° C. for 1 hour. The lysate is then gently extracted with phenol/chloroform followed by two chloroform washes. Total DNA is isolated by ethanol precipitation and resuspension in resuspension buffer (10 mnM Tris pH=7.4, 1 mM EDTA, and 0.1 mg/mL RNase). Chloroplast DNA can be purified by adding of denaturing solution (200 mM NaOH and 1% SDS (w/v)) is added to the resuspended DNA and inverted several times. Neutralizing solution (3.0 M potassium acetate, pH=5.5) is added, mixed, incubated on ice for 10 min and centrifuged at 15000 RPM for 30 min. The supernatant is decanted and applied to a QIAGEN-tip 500 and the DNA is isolated according to the QIAGEN Plasmid Maxi Kit.

An alternative method for preparing purified chloroplast DNA from *Chlamydomonas reinhardtii* involves embedding algae cells or purified chloroplasts in low-melt agarose plugs to prevent shearing of the DNA. Chloroplasts are isolated by lysing whole cells in a nitrogen decompression chamber and separating intact cells and debris from the chloroplasts by percoll density gradient centrifugation. To lyse the cells and/or chloroplasts, the plugs are incubated at 55° C. for 36 hours in lysis buffer (0.5 M EDTA, 1% Sarkosyl, 0.2 mg/mL proteinase K). When lysis is complete, plugs are washed 3 times with TE, and then stored in storage buffer (10 mM Tris pH=7.4, 1 mM EDTA). To release chloroplast DNA into solution, the plugs are washed 3 times with 30 mM NaCl, and melted at 65° C. for 10 min. The melted plugs are shifted to 42° C. and treated with β-agarase (New England Biolabs) for 1 hour. The solution of DNA can be used directly for downstream applications or ethanol precipitated to concentrate the sample.

To prepare DNA from yeast to use as a template for PCR, $10^6$ yeast cells (from agar plate or liquid culture) are suspended in lysis buffer (6 mM KHPO4, pH=7.5, 6 mM NaCl, 3% glycerol, lU/mL zymolyase) and heated to 37° C. for 30 min, 95° C. for 10 minutes, then cooled to near 23° C. The solution is added to the PCR mixture directly.

To prepare plasmid DNA from yeast, desired clones are grown in selective liquid media (e.g., CSM-Trp) to saturation at 30° C. Cells are collected by centrifugation at 3000×g for 10 minutes and resuspended in 150 uL of lysis buffer (1 M sorbitol, 0.1 M sodium citrate, 0.06 M EDTA pH=7.0, 100 mM beta-mercaptoethanol, and 2.5 mg/mL zymolyase). The solution is incubated for 1 hr at 37° C. 300 uL of denaturing solution (1% SDS and 0.2N NaOH) is added and solution is incubated at 60° C. for 15 min. 150 uL of neutralizing solution (3M potassium acetate, pH=4.8) is added and the solution is incubated on ice for 10 min. The solution is centrifuged at 14,000 RPM for 10 min and the supernatant is transferred to another tube. 1 mL of isopropanol is added, the mixture is gently mixed and centrifuged at 14,000 RPM for 10 min. The pellet is washed once with 1 mL of 70% ethanol and centrifuged at 14,000 RPM for 10 min. The DNA pellet is air-dried and resuspended in 60 uL of resuspension buffer (10 mM Tris pH=7.4, 1 mM EDTA, and 0.1 mg/mL RNase).

To prepare plasmid DNA from bacteria, cells are grown to saturation at 37° C. in LB containing the appropriate antibiotic (Kan or Amp). If the DNA of interest contains standard replication elements, cells are harvested by centrifugation. If the DNA of interest contains P1 replication elements, saturated cell cultures are diluted 1:20 in LB+Kan+IPTG and grown for 4 hours at 37° C., then harvested. The Plasmid Maxi kit (QIAGEN) is used to prepare plasmid DNA from the cell pellets.

For illustrative purposes, and without limiting the invention to the specific methods described, DNA samples prepared from algae, yeast, or bacteria (in plugs or in solution) are analyzed by pulse-field gel electrophoresis (PFGE), or digested with the appropriate restriction endonuclease (e.g., SmaI) and analyzed by PFGE, conventional agarose gel electrophoresis, and/or Southern blot. Standard protocols useful for these purposes are fully described in Gemmill et al. (in "Advances in Genome Biology", Vol. 1, "Unfolding The Genome," pp 217 251, edited by Ram S. Verma).

One of skill will appreciate that many other methods known in the art may be substituted in lieu of the ones specifically described or referenced.

Example 2

Transformation Methods

*E. coli* strains DH10B or Genehog are made electrocompetent by growing the cells to an $OD_{600}$ of 0.7, then collected and washed twice with ice-cold 10% glycerol, flash frozen in a dry-ice ethanol bath and kept at −80° C. Total yeast or algae DNA is prepared and electroporated into *E. coli* by using, for example, a 0.1 cm cuvette at 1,800 V, 200 ohms and 25 mF in a Bio-Rad Gene Pulsar Electroporator. Cells are allowed to recover and clones are selected on agar growth media containing one or more antibiotics, such as kanamycin (50 μg/mL), ampicillin (100 μg/mL), gentamycin (50 μg/mL), tetracycline (51 μg/mL), or chloramphenicol (34 μg/mL).

Yeast strains YPH857, YPH858 or AB 1380 may be transformed by the lithium acetate method as described in Sheistl & Geitz (Curr. Genet. 16:339 346, 1989) and Sherman et al., "Laboratory Course Manual Methods in Yeast Genetics" (Cold Spring Harbor Laboratory Press, Cold Spring Harbor, 1986) or a spheroplast method such as the one described by Sipiczki et al., *Curr. Microbiol.*, 12(3):169-173 (1985). Yeast transformants are selected and screened on agar media lacking amino and/or nucleic acids, such as tryptophan, leucine, or uracil. Standard methods for yeast growth and phenotype testing are employed as described by Sherman et al., supra.

Algae strains cscl37c (mt+), W1.1, or W1-1 may be transformed by particle bombardment. Cells are grown to late log phase (approximately 7 days) in TAP medium in the presence or absence of 0.5 mM 5-fluorodeoxyuridine (Gorman and Levine, *Proc. Natl. Acad. Sci., USA* 54:1665-1669, 1965, which is incorporated herein by reference) at 23° C. under constant illumination of 450 Lux on a rotary shaker set at 100 rpm. Fifty ml of cells are harvested by centrifugation at 4,000×g at 23° C. for 5 min. The supernatant is decanted and cells resuspended in 4 ml TAP medium for subsequent chloroplast transformation by particle bombardment (Cohen et al., supra, 1998).

One of skill will appreciate that many other transformation methods known in the art may be substituted in lieu of the ones specifically described or referenced herein.

Example 3

A Hybrid Gap-Filling Vector to Capture a Chloroplast Genome

Figure 1B:
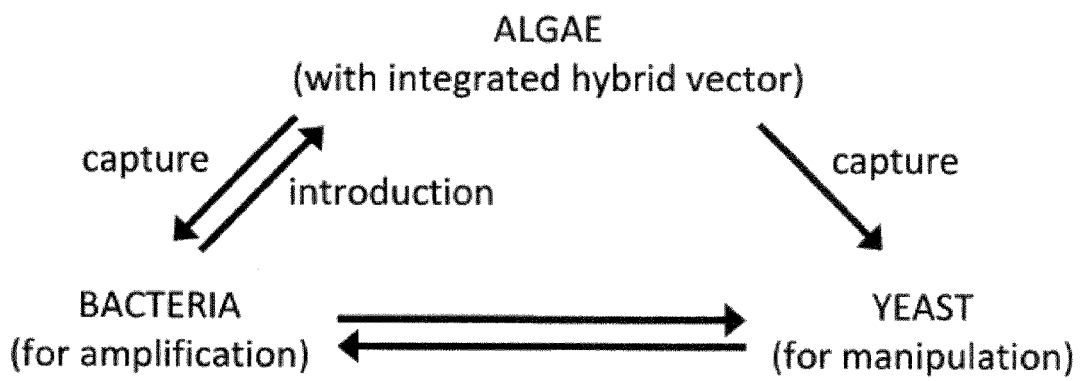

In this example, a system is established using a hybrid gap-filling vector to capture chloroplast DNA (FIG. 1). The hybrid gap filling vector backbone contains yeast elements that allow it to function as a yeast artificial plasmid (YAP) and bacterial elements that allow it to function as a plasmid artificial chromosome (PAC). The yeast elements include a yeast selection marker sequence (e.g. TRP1 or LEU2), a yeast centromere sequence (CEN), and a yeast autonomously replicating nucleotide sequence (ARS). Bacterial elements include a P1 or bacterial origin of replication sequence and a bacterial selection maker sequence (e.g. Kan').

To manipulate the hybrid gap-filling vector, the vector pDOCI (SEQ ID NO. 1) was generated. Portions of pTRP-AU (FIG. 2) were amplified using PCR primer pairs that anneal to sites surrounding the region encompassing TEL, ADE2, and URA3. One pair amplifies a region within the yeast elements (SEQ ID NOs. 21 and 22) and the other pair amplifies a region within the bacterial elements (SEQ ID NOs. 23 and 24). The PCR products were assembled into a single DNA fragment by PCR assembly using a single primer pair (SEQ ID NOs. 21 and 24). The assembled product was digested with NotI and ligated to NotI-digested pUC-SE (SEQ ID NO. 2) to form pDOCI (SEQ ID NO. 1).

To adapt the hybrid gap-filling vector to capture chloroplast DNA, the vector pDOCI-10 (SEQ ID NO. 3) was generated. Portions of the *C. reinhardtii* chloroplast genome were PCR amplified using two primer pairs specific for two adjacent regions (SEQ ID NOs. 25 and 26 and SEQ ID NOs. 27 and 28) near the psbD locus. (FIG. 3; indicated by number 10 surrounded by a box). Each PCR product was digested with NotI and I-SceI and ligated to pDOCI (SEQ ID NO. 1) that was digested with I-SceI to form pDOCI-10 (SEQ ID NO. 3).

To adapt pDOCI-10 to confer antibiotic resistance in algae, a selection marker was cloned. pSE-3HB-Kan (SEQ ID NO. 4), which contains a kanamycin resistance encoding gene from bacteria, which is regulated by the 5' UTR and promoter sequence for the atpA gene from *C. reinhardtii* and the 3' UTR sequence for the rbcL gene from from *C. reinhardtii*, was digested with SnaBI, which liberated the kanamycin resistance cassette. The cassette was ligated to SnaBI-digested pDOCI-10 to form pDOCI-10-Kan (SEQ ID NO. 5).

Figure 2:
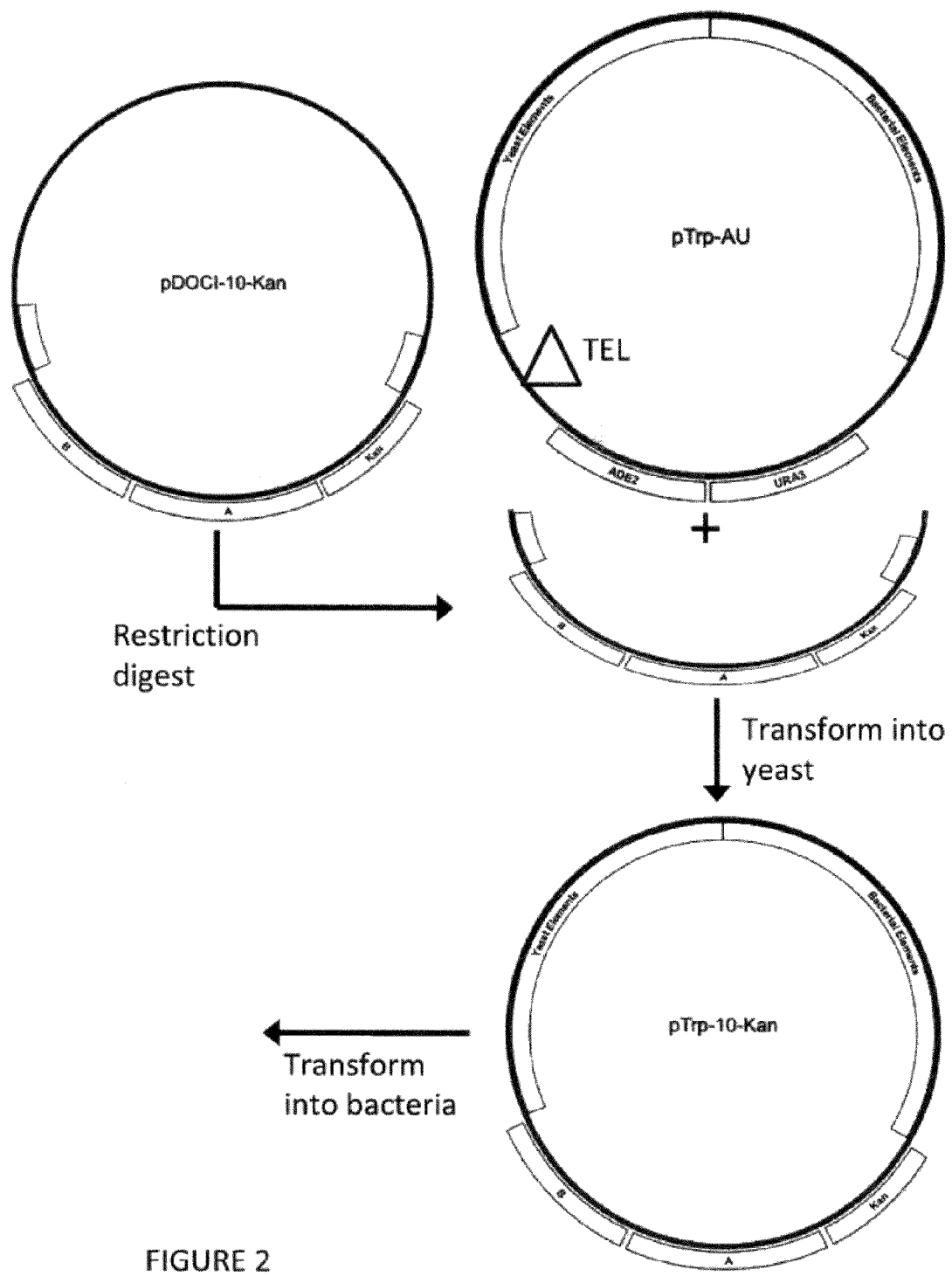
FIG. 2 is a schematic showing construction of a hybrid vector.

The hybrid gap-filling for capturing chloroplast DNA, pTRP-10-Kan (SEQ ID NO. 6), was constructed using recombination in yeast (FIG. 2). Briefly, pDOCI-10-Kan was digested with PacI and AscI to liberate the cassette that introduces chloroplast genome-specific elements into the hybrid gap-filling vector. This cassette was transformed along with pTRP-AU into the yeast strain YPH858 using the lithium acetate method. Homologous recombination takes place in vivo in the transformed yeast cells. Transformants that correctly integrated with cassette were isolated based on growth on CSM-Trp agar media containing 5-fluoroorotic acid (5-FOA) and by red color. 5-FOA selects for clones that lack a functional URA3 gene and the red color results when the ADE2 gene is eliminated. Plasmid DNA was isolated from yeast clones that were grown in CSM-Trp liquid media and transformed into E. coli (DH10B). To generate large amounts of pTRP-10-Kan, DH10B cells harboring pTRP-10-Kan were grown to saturation at 37° C. in LB+Kan (50 ug/mL), and then diluted 1:20 in LB+Kan+IPTG and grown for 4 hours at 37° C. DNA was prepared from the bacterial culture using the Plasmid Maxi kit (QIAGEN).

The composition of the vector was verified by DNA sequencing of the entire plasmid.

Example 4

Vectors to Stabilize and/or Modify Chloroplast Genome DNA in an Exogenous Host

Often, large pieces of heterologous DNA are instable in host organisms such as yeast or bacteria. This may be due to multiple factors, including, but not limited to, the presence of toxic gene products or codon bias and/or lack of selective pressure. Therefore, the target DNA within the shuttle vector may be altered within yeast or bacteria. For example, certain portions of a target DNA sequence (e.g., coding regions or promoters) may be deleted or moved by recombination within the host organism. In a similar way, when a shuttle vector carrying the target DNA is transferred back to the organism (or a closely related species) that donated the target DNA, the target DNA can become unstable.

Such sites of instability and susceptible sequences are readily discovered by determining which pieces of genomic DNA elude capture or disappear over time. These sites can be detected by comparing initially isolated gap-filling target DNA plasmids with plasmids isolated from transformed strains which have been sequentially passaged in the laboratory under conditions which select for the presence of the plasmid-encoded selectable marker (e.g., TRP1) or by comparison with native target DNA (e.g., C. reinhardtii chloroplast DNA). Such comparison may be performed, for example, by restriction fragment length polymorphism (RFLP) analysis or direct sequencing. One of skill in the art will recognize that there are multiple other protocols and methods to determine such differences.

Figure 4A:
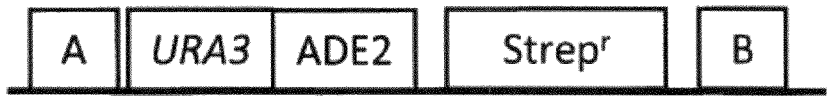
FIGS. 4A-4C are schematics showing sites of integration in chloroplast genome DNA. Circled numbers indicate target sites for modification. The box indicates the site targeted by the hybrid gap-filling vector.

Once identified, such sites and sequences can be forced to remain through selection of markers. FIG. 4 shows examples of arrangements of selectable markers in the multiple cloning site of a vector.

To generate a stabilization vector containing yeast and algae stability elements, the region of DNA in pTrp-AU encompassing the ADE2 and URA3 genes was liberated by digestion with SfiI followed by gel purification of the desired fragment. The fragment was treated with Klenow fragment to create blunt ends and ligated to PmlI-degested pSE-3HB-Strep (SEQ ID NO. 7), creating pSE-3HB-Strep-AU (FIG. 4B). pSE-3HB-Strep is a vector that targets a streptomycin resistance encoding gene from bacteria, which is regulated by the 5' UTR and promoter sequence for the atpA gene from C. reinhardtii and the 3' UTR sequence for the rbcL gene from C. reinhardtii, to the 3HB locus of the C. reinhardtii chloroplast genome.

Figure 3:
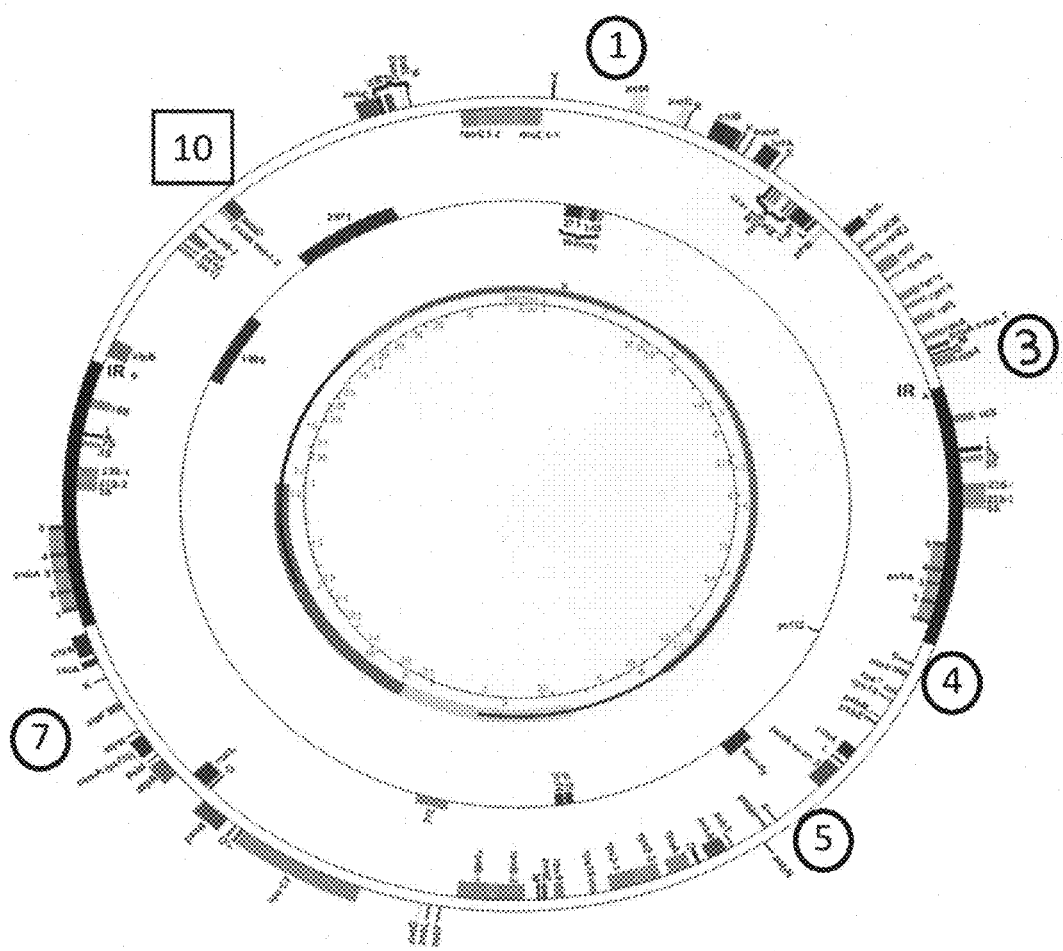
FIG. 3 is a schematic of selectable markers for modification and/or stabilization.

To generate vectors that target other regions of the chloroplast genome, 800-1000 bp regions were amplified using PCR primer pairs that anneal to 5' and 3' regions flanking the sites indicated by numbered circles in FIG. 3 (site 1-5', SEQ ID NOs. 29 and 30; site 1-3', SEQ ID NOs. 31 and 32; site 3-5', SEQ ID NOs. 33 and 34; site 3-3', SEQ ID NOs. 35 and 36; site 4-5', SEQ ID NOs. 37 and 38; site 4-3', SEQ ID NOs. 39 and 40; site 5-5', SEQ ID NOs. 41 and 42; site 5-3', SEQ ID NOs. 43 and 44; and site 7-5', SEQ ID NOs. 45 and 46; site 7-3', SEQ ID NOs. 47 and 48). Each pair of PCR products was digested with NotI and I-SceI, mixed, and ligated to NotI-digested pUC-SE (SEQ ID NO. 2), producing plasmids pUC 1, pUC3, pUC4, pUC5 and pUC7 (named for their position of integration).

Figure 4B:
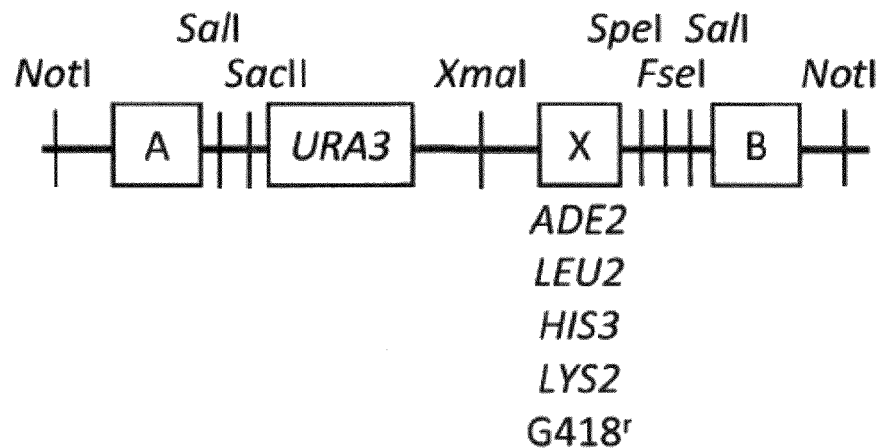

Pairs of yeast selection markers were constructed so that multiple stabilization sites could be employed simultaneously (FIG. 4B). Each marker pair contains the URA3 gene (SEQ ID NO. 8), which was PCR amplified from pRS416. Each marker pair also contains the LEU2 gene (SEQ ID NO. 9) amplified from pRS415, the H153 gene (SEQ ID NO. 10) amplified from pRS413, the ADE2 gene (SEQ ID NO. 11) amplified from pTrp-AU, the LYS2 gene (SEQ ID NO. 12) amplified from S. cerevisiae genomic DNA, or the kanMX6 gene (SEQ ID NO. 13) from pFA6a-kanMX6, which confers resistance to the antifungal agent G418. The primers used for the URA3 gene add the XmaI restriction site to the 5' end (SEQ ID NO. 49) and SalI and SacII to the 3' end (SEQ ID NO. 50). The primers used for the LEU2, HIS3, ADE2, LYS2, and G418' genes add the XmaI restriction site to the 5' end (SEQ ID NO.51 for LEU2, SEQ ID NO. 52 for H153, SEQ ID NO. 53 for ADE2, SEQ ID NO.54 for LYS2, and SEQ ID NO. 55 for G418') and SalI, FseI, and SpeI sites to the 3' end (SEQ ID NO. 56 for LEU2, SEQ ID NO. 57 for H153, SEQ ID NO. 58 for ADE2, SEQ ID NO.59 for LYS2, and SEQ ID NO. 60 for G418'). Each PCR product was digested with XmaI and SalI, mixed pairwise, and ligated into the desired integration vector, resulting in pUC1-URA3/ADE2, pUC3-URA3/LEU2, pUC4-URA3/HIS3, pUC5-URA3/ADE2, and pUC7-URA3/LYS2. URA3 is used in each case because it allows for positive and negative selection. Marker pairs can be introduced based on selection for either gene (in the case of a single modification), the non-URA3 gene in the case of two or more modification. Then the markers can be removed by introducing DNA with terminal sequences homologous to those surrounding the marker pairs and selecting for growth on minimal media containing 5-FOA.

Figure 4C:
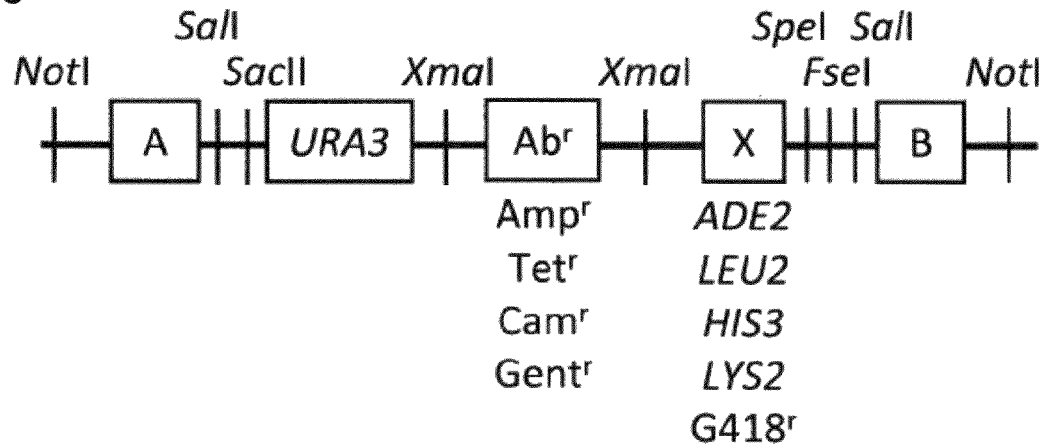

To promote sequence stability in bacteria, antibiotic resistance markers were cloned into the yeast selection marker pairs. The bacterial stability markers include, but are not limited to, the ampicillin resistance gene (Amp$^r$, SEQ ID NO. 14) amplified from pET-21a, the tetracycline resistance gene (Tet$^r$, SEQ ID NO. 15) amplified from pBR322, the chloramphenicol resistance gene (Cam$^r$, SEQ ID NO. 16) amplified from pETcoco-1, and the gentamycin resistance gene (Gent$^r$, SEQ ID NO. 17) amplified from pJQ200. For each gene, primer pairs (SEQ ID NOs. 61 and 62 for Amp$^r$, SEQ ID NOs. 63 and 64 for Tet$^r$, SEQ ID NOs. 65 and 66 for Cam$^r$, and SEQ ID NOs. 67 and 68 for Gent$^r$) that add XmaI sites to both the 5' and 3' ends were used to PCR amplify the antibiotic resistance fragment. Each PCR product was digested with XmaI and ligated into XmaI-digested pUC1-URA3/ADE2, pUC3-URA3/LEU2, pUC4-URA3/HIS3, pUC5-URA3/ADE2, and pUC7-URA3/LYS2. FIG. 4C shows the arrangement of the yeast and bacterial stability markers.

Example 5

Introduction of Hybrid and Stabilization Vectors into a Chloroplast Genome

To generate a *C. reinhardtii* chloroplast genome that contains a hybrid vector with or without a stabilization vector, pTRP-10-Kan and pSE-3HB-Strep-AU were transformed into algae cells. pTRP-10-Kan was digested with NotI to linearize the vector such that the chloroplast targeting elements on are on each end (FIG. 5). pSE-3HB-Strep-AU was transformed as circular DNA.

For these experiments, all transformations are carried out on *C. reinhardtii* strain 137c (mt+). Cells are grown to late log phase (approximately 7 days) in the presence of 0.5 mM 5-fluorodeoxyuridine in TAP medium (Gorman and Levine, *Proc. Natl. Acad. Sci., USA* 54:1665-1669, 1965, which is incorporated herein by reference) at 23° C. under constant illumination of 450 Lux on a rotary shaker set at 100 rpm. Fifty ml of cells are harvested by centrifugation at 4,000×g at 23° C. for 5 min. The supernatant is decanted and cells resuspended in 4 ml TAP medium for subsequent chloroplast transformation by particle bombardment (Cohen et al., supra, 1998). All transformations are carried out under kanamycin selection (100 µg/ml) in which resistance is conferred by the gene encoded by the segment in FIG. 5 labeled "Kan." (Chlamydomonas Stock Center, Duke University).

PCR is used to identify transformed strains. For PCR analysis, $10^6$ algae cells (from agar plate or liquid culture) are suspended in 10 mM EDTA and heated to 95° C. for 10 minutes, then cooled to near 23° C. A PCR cocktail consisting of reaction buffer, MgC12, dNTPs, PCR primer pair(s), DNA polymerase, and water is prepared. Algae lysate in EDTA is added to provide a template for the reaction. The magnesium concentration is varied to compensate for amount and concentration of algae lysate and EDTA added. Annealing temperature gradients are employed to determine optimal annealing temperature for specific primer pairs.

Figure 6:
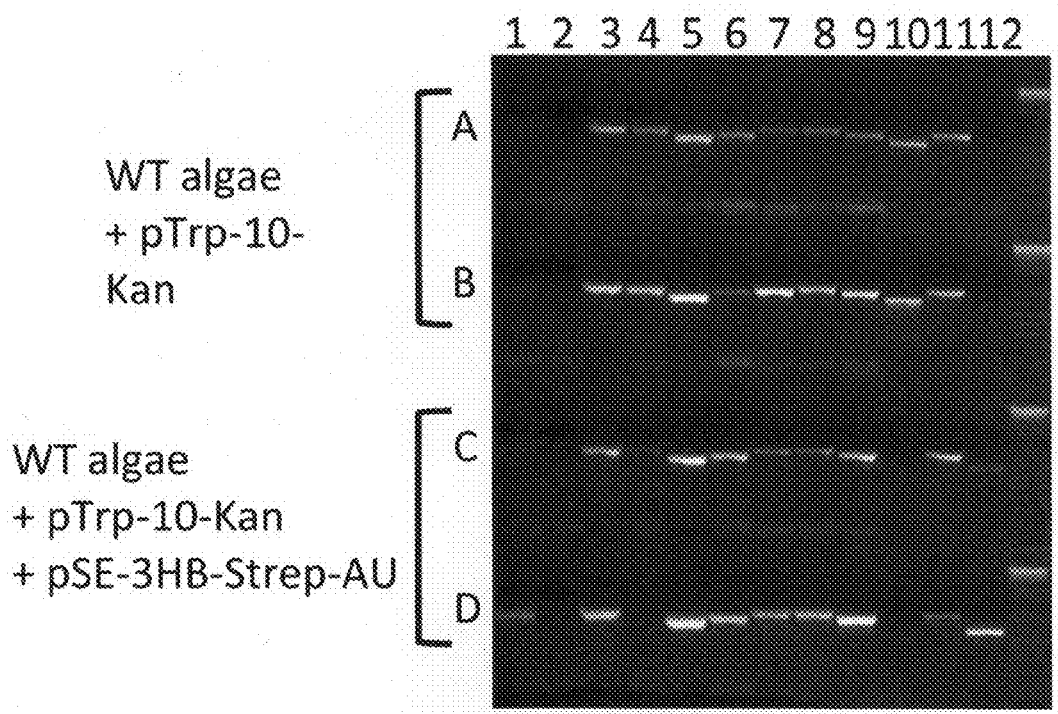
FIG. 6 is PCR data showing integration of hybrid vector (and stabilization vector) in algae.

FIG. 6 shows examples of isolated algae strains that contain pTrp-10-Kan with and without pSE-3HB-Strep-AU. Strains that integrated pTRP-10-Kan were identified using any of a set of primer pairs that amplify different regions in the vector backbone (Lane 1, SEQ ID NOs. 69 and 70; Lane 2, SEQ ID NOs. 71 and 72; Lane 3, SEQ ID NOs. 73 and 74; Lane 4, SEQ ID NOs. 75 and 76; Lane 5, SEQ ID NOs. 77 and 78; Lane 6, SEQ ID NOs. 79 and 80; Lane 7, SEQ ID NOs. 81 and 82; Lane 8, SEQ ID NOs. 83 and 84; and Lane 9, SEQ ID NOs. 85 and 86) or primer pairs that span the junction between pTrp-10-Kan DNA and chloroplast genome DNA (Lane 10, SEQ ID NOs. 87 and 88; Lane 11, SEQ ID NOs. 89 and 90). To identify strains that have integrated pSE-3HB-Strep-AU, primer pairs (SEQ ID NOs. 91 and 92) were used which amplify regions within the ADE2 gene. Desired clones are those that yield PCR products of expected size.

Example 6

Capture of a Chloroplast Genome into an Exogenous Host

In this example, *C. reinhardtii* chloroplast DNA is isolated using standard techniques as described above. *C. reinhardtii* chloroplast DNA containing the pTRP-10-Kan vector with or without pSE-3HB-Strep-AU was used to transform bacteria. Electrocompetent *E. coli* strains DH10B or Genehog were transformed and selected on LB agar growth medium with kanamycin (50 mg/l). DNA from individual clones was isolated by growing the cells to saturation at 37° C. in LB liquid growth medium with kanamycin (50 mg/l). Saturated cell cultures are diluted 1:20 in LB+Kan+IPTG and grown at 37° C. for 4 hours. The Plasmid Maxi kit (QIAGEN) is used to prepare plasmid DNA from the isolated clones.

Figure 7A:
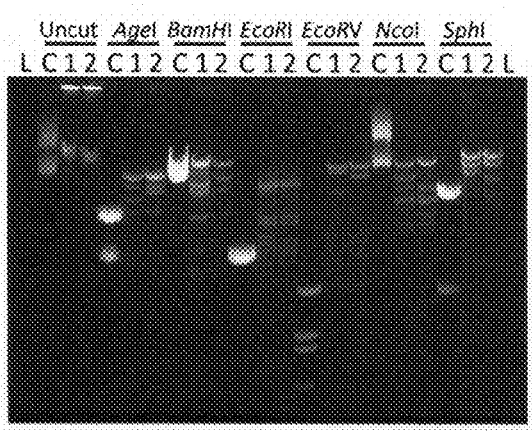
FIG. 7 shows analysis of captured DNA. 7A Restriction digest with EcoRI of isolated vectors containing chloroplast (L, ladder; C, parent hybrid vector; 1, Clone 1; and 2; Clone 2). 7B Restriction digest with EcoRI of isolates of Clone 1 that were passaged through yeast (L, ladder; C,; 1, Clone 1; and A-M; yeast isolates). 7C Southern analysis of Clones 1 and 2 digested with EcoRI and probed with radioactive HindIII-digested total DNA from *C. reinhardtii*.

FIG. 7A shows the restriction analysis of two types of clones obtained from bacterial transformation (Clone 1 and Clone 2) compared to the parent hybrid vector (Clone C). Clones 1 and 2 are composed of >100 kb of DNA while the parent hybrid vector is composed of only 23 kb of DNA, demonstrating that large portions of DNA were indeed captured by the hybrid vector. Restriction mapping indicates that Clone 1 comprises approximately half of the chloroplast genome (FIG. 8A). DNA sequencing of the regions flanking the hybrid vector indicate that a recombination event occurred between the 3' UTR of the *C. reinhardtii* kanamycin resistance cassette (which is the 3' UTR from the rbcL gene in *C. reinhardtii*) and the 3' UTR of the *C. reinhardtii* streptomycin resistance cassette (which is the 3' UTR from the rbcL gene in *C. reinhardtii*). Clone 1 retained the *C. reinhardtii* kanamycin resistance cassette, but lost the *C. reinhardtii* streptomycin resistance cassette. Restriction mapping indicates that Clone 2 also comprises approximately half of the chloroplast genome (FIG. 8B). However, DNA sequencing of the regions flanking the hybrid vector indicate that a different recombination event occurred to give rise to Clone 2. The 5' UTR of the *C. reinhardtii* kanamycin resistance cassette (which is the 5' UTR from the atpA gene in *C. reinhardtii*) recombined with the 5' UTR of the atpA gene in the *C. reinhardtii* chloroplast genome and the inverted repeat B (IR-B in FIG. 8) recombined with inverted repeat A (IR-A in FIG. 8). Clone 2 lost both the *C. reinhardtii* kanamycin resistance cassette and the *C. reinhardtii* streptomycin resistance cassette.

Figure 7B:
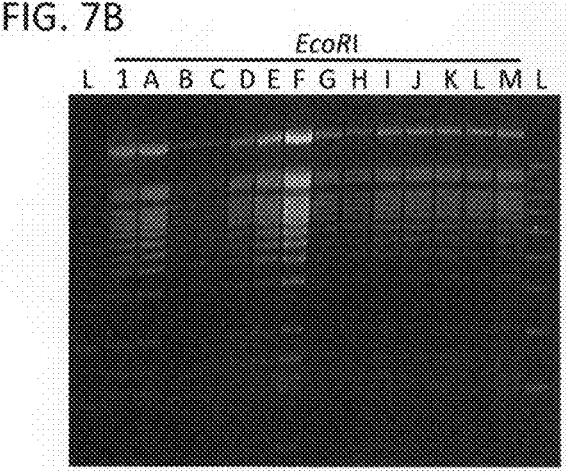

To demonstrate that the hybrid vector would support stable replication in yeast, Clone 1 was transformed into the yeast strain AB1380 by the lithium acetate method and transfomants were selected on CSM-Trp agar media. Transformants were PCR screened using a primer pair (SEQ ID NOs 97 and 98) that amplifies a region with the chloroplast genome DNA of Clone 1. Desired clones are those that give rise to a PCR product of expected size. Individual PCR-positive clones were streaked to generate multiple clones per isolate. DNA was prepared from the isolated yeast clones and transformed into bacteria. Bacteria were PCR screened using a primer pair (SEQ ID NOs 97 and 98) that amplifies a region within the chloroplast genome DNA of Clone 1. Desired clones are those that give PCR products of expected size. DNA was prepared from the isolated bacterial clones and analyzed by restriction digest with EcoRI. FIG. 7B shows that all isolated clones have restriction maps that are identical to the originally isolated Clone 1. Thus, the hybrid vector supports stable replication in yeast.

Figure 7C:
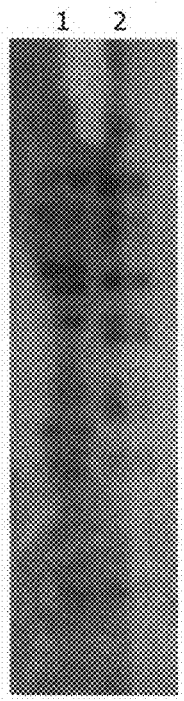

To determine if the captured DNA is indeed chloroplast genome DNA, a Southern blot was performed. Clones 1 and 2 prepared from bacteria were digested with EcoRI, separated by gel electrophoresis, transferred to a membrane, and probed with radioactive HindIII-digested total DNA from *C. reinhardtii*. FIG. 7C shows that the DNA in Clones 1 and 2 give rise to a signal, thus indicating that the captured DNA is chloroplast genome DNA.

Example 7

Reintroduction of Chloroplast Genome DNA into Algae

For these experiments, all transformations are carried out on either *C. reinhardtii* strain W1.1, which expresses SAA from the endogenous psbA loci, or W1-1, which expresses LuxAB from the endogenous psbA loci. Both W1.1 and W1-1 are resistant to spectinomycin by virtue of transformation of p228, which introduces a mutation in the 16S rRNA. Cells are grown to late log phase (approximately 7 days) in TAP medium (Gorman and Levine, *Proc. Natl. Acad. Sci., USA* 54:1665-1669, 1965, which is incorporated herein by reference) at 23° C. under constant illumination of 450 Lux on a rotary shaker set at 100 rpm. Fifty ml of cells are harvested by centrifugation at 4,000×g at 23° C. for 5 min. The supernatant is decanted and cells resuspended in 4 ml HSM medium for subsequent chloroplast transformation by particle bombardment (Cohen et al., supra, 1998). All transformations are carried out on HSM agar.

Figure 9:
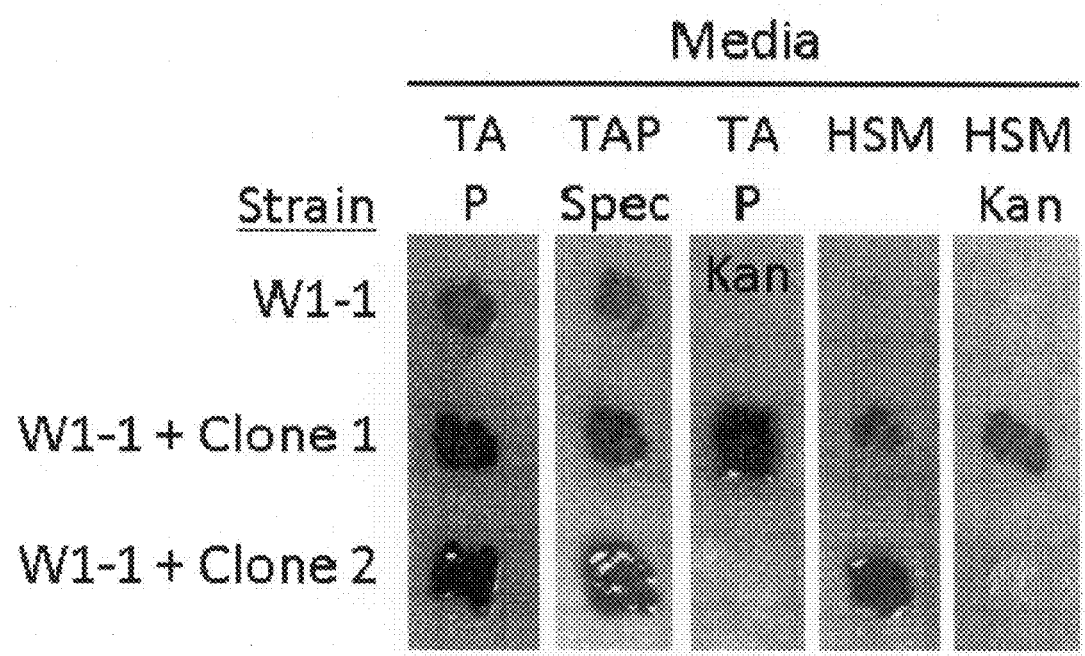
FIG. 9 shows growth of parent and transformed algae cells under various selection conditions.

Transformants were selected by growth on HSM, indicating that function of the psbA gene locus was restored. Clones were also subsequently checked for growth on TAP, TAP with spectinomycin (150 µg/ml), TAP with kanamycin (100 µg/ml), HSM, and HSM with kanamycin (100 µg/ml). FIG. 9 shows that W1-1 transformed with Clone 1 is able to grow on all media types. FIG. 9 also shows that W1-1 transformed with Clone 2 is unable to grow on media containing kanamycin, which is expected since Clone 2 does not contain a Kan resistance marker.

Example 8

Modification of Chloroplasts for Producing Biomass-Degrading Enzymes

Figure 10A:
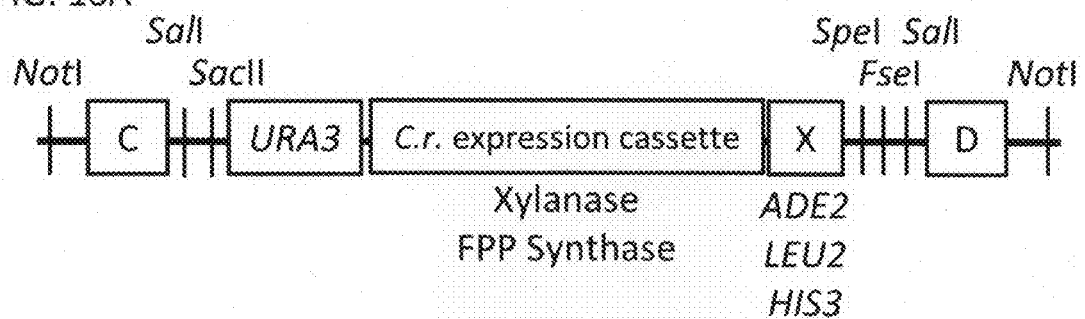

To modify captured chloroplast genome DNA for production of a xylanase, an algae expression cassette was cloned into the yeast marker vectors described in EXAMPLE 4. Briefly, a *C. reinhardtii* chloroplast expression vector was digested with SpeI to liberate a fragment of DNA (SEQ ID NO. 18) with xylanase from *T. reesei* regulated by the 5' UTR for the psbD gene from *C. reinhardtii* and the 3' UTR for the psbA gene from *C. reinhardtii*. The fragment was treated with Klenow fragment to create blunt ends and cloned into SmaI (XmaI) site between the yeast markers in pUC1-URA3/ADE2, pUC3-URA3/LEU2, and pUC4-URA3/HIS3. FIG. 10A shows the arrangement of the various elements in the new vectors.

Chloroplast genome DNA was modified by transforming the modification vector into yeast that harbored the captured DNA. For transformation, all modification vectors were linearized by digestion with NotI. Yeast harboring Clone 1 (from EXAMPLE 6) were grown to saturation in CSM-Trp media at 30° C., then diluted 1:20 in YPAD and grown for 4 hours at 30° C. Yeast were transformed using the lithium-acetate method and transformants were selected for by growth on CSM-Ura media. Transformants were propagated on CSM-Trp-Ura media and then PCR screened using primers specific for the xylanase expression cassette (SEQ ID NOs 95 and 96) and a region within the chloroplast genome DNA (SEQ ID NOs 97 and 98). Desired clones are those that give PCR products of expected size for both reactions. DNA was prepared from the isolated yeast clones and transformed into bacteria. Bacteria were PCR screened using primers specific for the xylanase expression cassette (SEQ ID NOs 95 and 96) and a region within the chloroplast genome DNA (SEQ ID NOs 97 and 98). Desired clones are those that give PCR products of expected size for both reactions. DNA was prepared from the isolated bacterial clones and analyzed by restriction digest with EcoRI. FIG. 10B shows that clones were isolated that have restriction maps that are consistent with integration of the xylanase expression cassette in the desired position.

For these experiments, all transformations are carried out on either *C. reinhardtii* strain W1.1, which expresses SAA from the endogenous psbA loci, or W1-1, which expresses LuxAB from the endogenous psbA loci. Both W1.1 and W1-1 are resistant to spectinomycin by virtue of transformation of p228, which introduces a mutation in the 16S rRNA. Cells are grown to late log phase (approximately 7 days) in TAP medium (Gorman and Levine, *Proc. Natl. Acad Sci., USA* 54:1665-1669, 1965, which is incorporated herein by reference) at $2^{3°}$ C. under constant illumination of 450 Lux on a rotary shaker set at 100 rpm. Fifty ml of cells are harvested by centrifugation at 4,000×g at $2^{3°}$ C. for 5 min. The supernatant is decanted and cells resuspended in 4 ml HSM medium for subsequent chloroplast transformation by particle bombardment (Cohen et al., supra, 1998). All transformations are carried out on HSM agar.

Transformants were identified by growth on HSM, indicating that function of the psbA gene locus was restored. PCR is used to identify transformants that also contain the endoxylanase expression cassette. For PCR analysis, $10^6$ algae cells (from agar plate or liquid culture) are suspended in 10 mM EDTA and heated to 95° C. for 10 minutes, then cooled to near 23° C. A PCR cocktail consisting of reaction buffer, MgCl2, dNTPs, PCR primer pair(s) (Table 2), DNA polymerase, and water is prepared. Algae lysate in EDTA is added to provide a template for the reaction. The magnesium concentration is varied to compensate for amount and concentration of algae lysate and EDTA added. Annealing temperature gradients are employed to determine optimal annealing temperature for specific primer pairs.

Figure 11A:
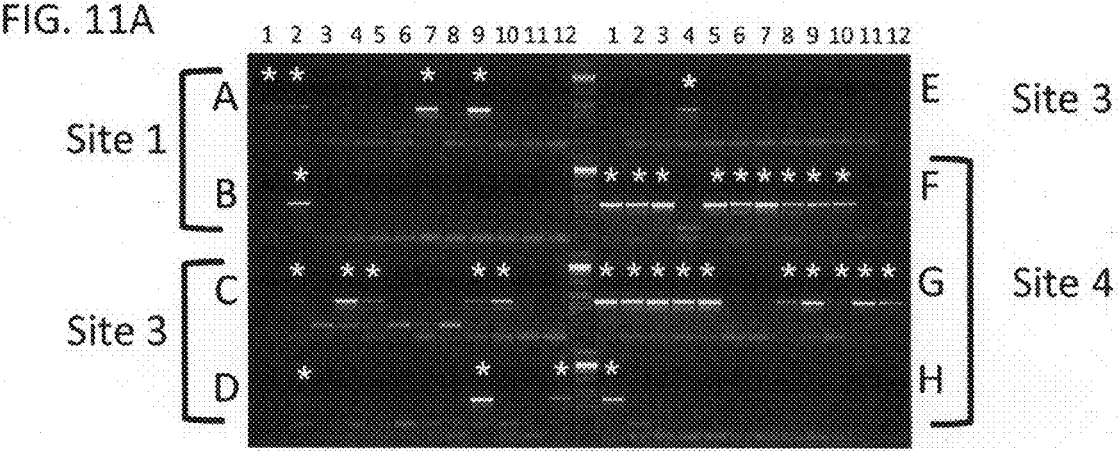
FIG. 11 shows modification of a chloroplast genome to produce a biomass-degrading enzyme. 11A PCR screen of isolated transformants. 11B Endoxylanase activity from isolated transformants.

To identify strains that have the endoxylanase expression cassette, a primer pair (SEQ ID NOs 95 and 96) was used which amplifies a region within the endoxylanase expression cassette. Desired clones are those that yield PCR products of expected size. FIG. 11A shows that multiple algae strains were obtained that contain the endoxylanase expression cassette (PCR products indicated with asterisk).

To determine whether finctional xylanase is expressed, enzyme activity is examined. Patches of cells (approximately 2 mg per patch) from TAP agar plates containing kanamycin (100 lg/mL) were resuspended in 50 ul of 100 mM sodium acetate pH 4.8 in a round bottom 96 well plate (Corning). Resuspended cells were lysed by addition of 20 ul of Bug-Buster Protein Extraction Reagent (Novagen) and shaken for five minutes at room temperature. Cell lysate (50 ul) was transferred to a black 96 well plate, and the chlorophyll fluorescence of the resulting wells was measured in a SpectraMax M2 microplate reader (Molecular Devices), with an excitation wavelength of 440 nm and an emission wavelength of 740 nm, with a 695 nm cutoff filter. The measured chlorophyll signal in RFUs (relative fluorescence units) was used to normalize the xylanase activity signal to the amount of biomass added to the reaction.

Figure 10A:
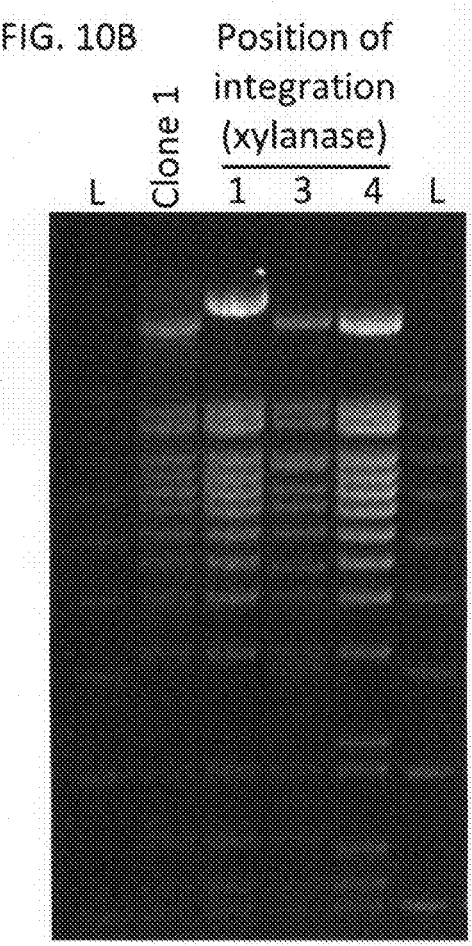
Figure 10A:
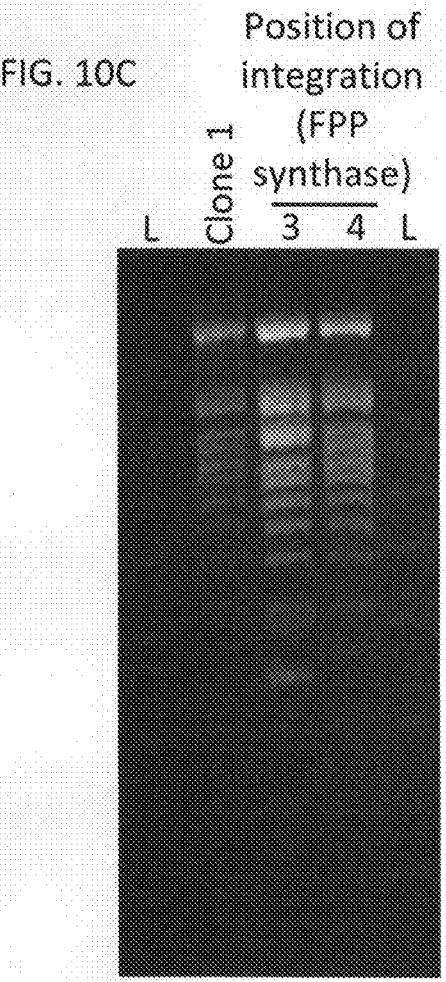
Figure 11B:
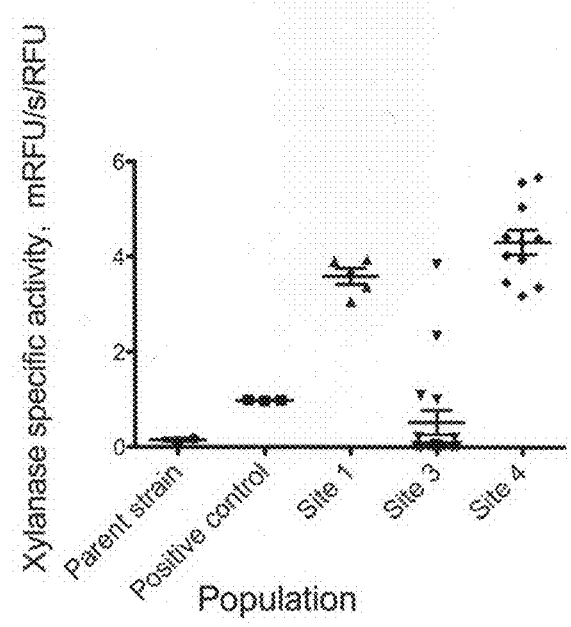

After measurement of the chlorophyll fluorescence, xylanase substrate was added. EnzCheck Ultra Xylanase substrate (Invitrogen) was dissolved at a concentration of 50 ug/ml in 100 mM sodium acetate pH 4.8, and 50 ul of substrate was added to each well of the microplate. The fluorescent signal was measured in a SpectraMax M2 microplate reader (Molecular Devices), with an excitation wavelength of 360 nm and an emission wavelength of 460 nm, without a cutoff filter and with the plate chamber set to 42 degrees Celsius. The fluorescence signal was measured for 15 minutes, and the enzyme velocity was calculated with Softmax Pro v5.2 (Molecular Devices). Enzyme velocities were recorded as RFU/minute. Enzyme specific activities were calculated as milliRFU per minute per RFU of chlorophyll fluorescence. FIG. 11B shows that multiple algae strains containing the xylanase expression cassette at site 1, 3, and 4 (see FIGS. 3 and 10) were obtained that produce functional xylanase enzyme.

Example 9

Modification of a Chloroplast Genome to Produce Terpenes

To modify captured chloroplast genome DNA for production of an FPP synthase, an algae expression cassette was cloned into the yeast marker vectors described in EXAMPLE 4. Briefly, a *C. reinhardtii* chloroplast expression vector was digested with SpeI to liberate a fragment of DNA (SEQ ID NO. 19) with FPP synthase from *G. gallus* regulated by the 5' UTR for the psbD gene from *C. reinhardtii* and the 3' UTR for the psbA gene from *C. reinhardtii*. The fragment was treated with Klenow fragment to create blunt ends and cloned into SmaI (XmaI) site between the yeast markers in pUC1-URA3/ADE2, pUC3-URA3/LEU2, and pUC4-URA3/HIS3. FIG. 10A shows the arrangement of the various elements in the new vectors.

Chloroplast genome DNA was modified by transforming the modification vector into yeast that harbored the captured DNA. For transformation, all modification vectors were linearized by digestion with NotI. Yeast harboring Clone 1 (from EXAMPLE 6) were grown to saturation in CSM-Trp media at 30° C., then diluted 1:20 in YPAD and grown for 4 hours at 30° C. Yeast were transformed using the lithium-acetate method and transformants were selected for by growth on CSM-Ura media. Transformants were propagated on CSM-Trp-Ura media and then PCR screened using primers specific for the FPP synthase expression cassette (SEQ ID NOs 95 and 99) and a region within the chloroplast genome DNA (SEQ ID NOs 97 and 98). Desired clones are those that gave PCR products of expected size for both reactions. DNA was prepared from the isolated yeast clones and transformed into bacteria. Bacteria were PCR screened using primers specific for the FPP synthase expression cassette (SEQ ID NOs 95 and 99) and a region within the chloroplast genome DNA (SEQ IDs 97 and 98). Desired clones are those that gave PCR products of expected size for both reactions. DNA was prepared from the isolated bacterial clones and analyzed by restriction digest. FIG. 10C shows that clones were isolated that have restriction maps that are consistent with integration of the FPP synthase expression cassette in the desired position.

For these experiments, all transformations are carried out on either *C. reinhardtii* strain W1.1, which expresses SAA from the endogenous psbA loci, or W1-1, which expresses LuxAB from the endogenouspsbA loci. Both W1.1 and W1-1 are resistant to spectinomycin by virtue of transformation of p228, which introduces a mutation in the 16S rRNA. Cells are grown to late log phase (approximately 7 days) in TAP medium (Gorman and Levine, *Proc. Natl. Acad. Sci., USA* 54:1665-1669, 1965, which is incorporated herein by reference) at 23° C. under constant illumination of 450 Lux on a rotary shaker set at 100 rpm. Fifty ml of cells are harvested by centrifugation at 4,000×g at 23° C. for 5 min. The supernatant is decanted and cells resuspended in 4 ml HSM medium for subsequent chloroplast transformation by particle bombardment (Cohen et al., supra, 1998). All transformations are carried out on HSM agar.

Transformants were identified by growth on HSM, indicating that function of the psbA gene locus was restored. PCR is used to identify transformants that also contain the FPP synthase expression cassette. For PCR analysis, $10^6$ algae cells (from agar plate or liquid culture) are suspended in 10 mM EDTA and heated to 95° C. for 10 minutes, then cooled to near 23° C. A PCR cocktail consisting of reaction buffer, MgC12, dNTPs, PCR primer pair(s), DNA polymerase, and water is prepared. Algae lysate in EDTA is added to provide a template for the reaction. The magnesium concentration is varied to compensate for amount and concentration of algae lysate and EDTA added. Annealing temperature gradients are employed to determine optimal annealing temperature for specific primer pairs.

Figure 12A:
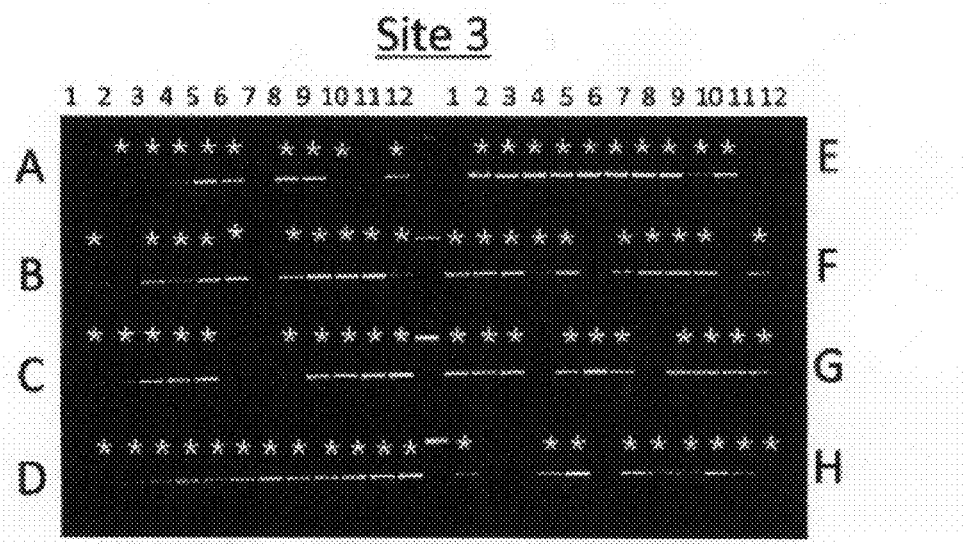
FIG. 12 shows a PCR screen of isolated transformants modified to produce isoprenoids with the FPP synthase expression cassette targeted to site 3 (12A) or site 4 (12B).
Figure 12B:
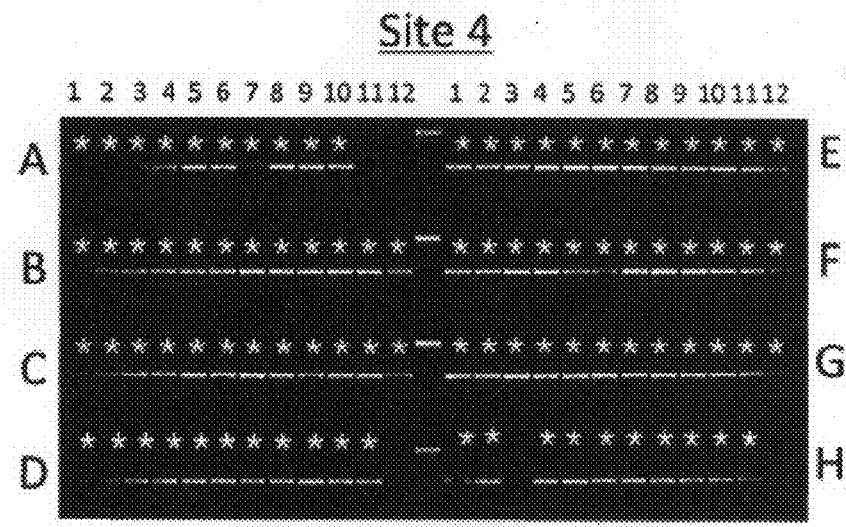

To identify strains that have the FPP synthase expression cassette, a primer pair was used which amplifies a region within the endoxylanase expression cassette. Desired clones are those that yield PCR products of expected size. Multiple algae strains were obtained that contain the FPP synthase expression cassette at (FIG. 12, PCR products indicated with asterisk).

Example 11

Gap-Filling a Partial Chloroplast Genome

Figure 13:
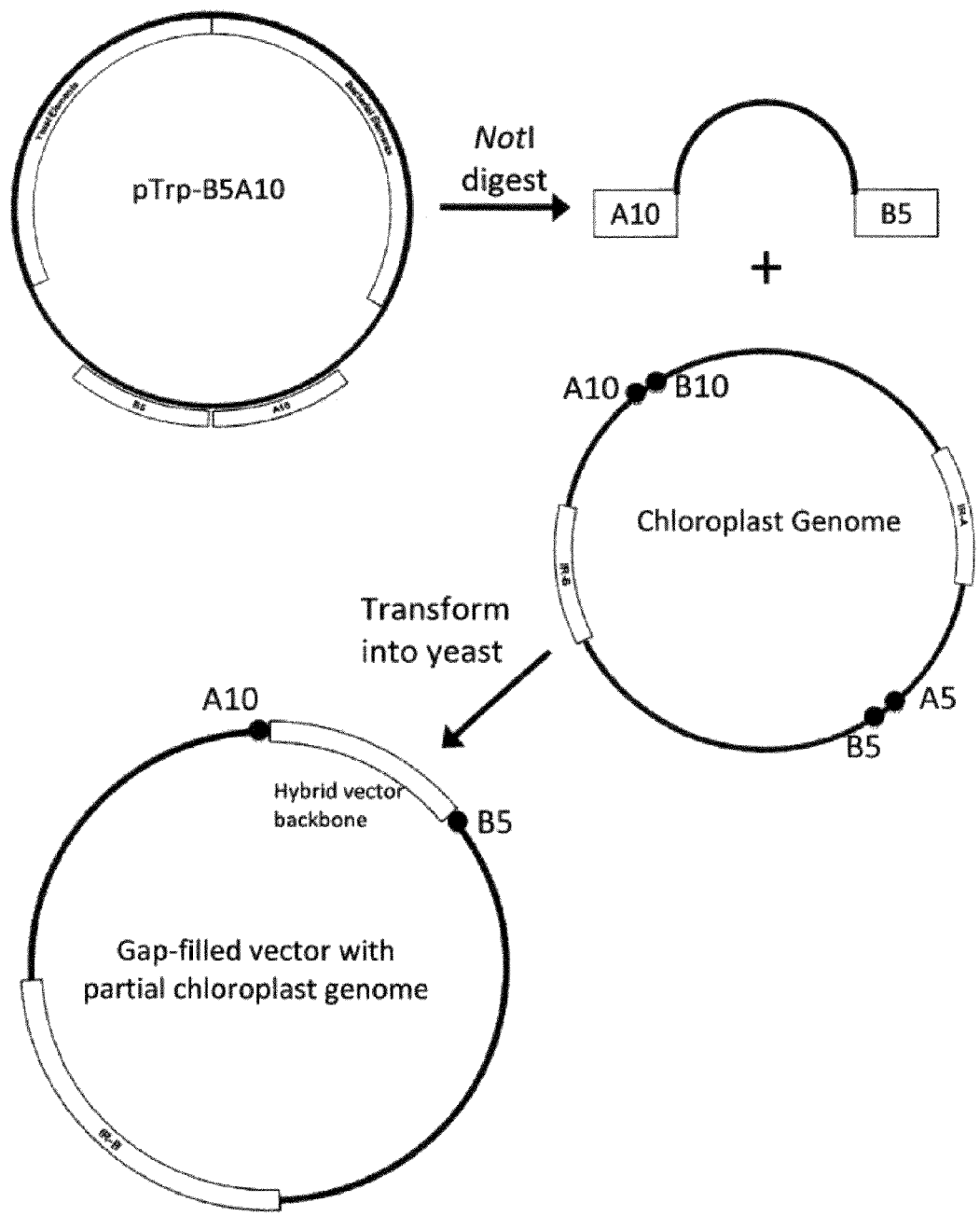
FIG. 13 is a schematic showing capture of a partial chloroplast genome using recombination in yeast.

In this example, a system is established using a hybrid gap-filling vector to capture chloroplast DNA by recombination in yeast (FIG. 13). To adapt the hybrid gap-filling vector to capture chloroplast DNA, the vector pDOCI-B5A 10 (SEQ ID NO. 20) was generated. Portions of the *C. reinhardtii* chloroplast genome were PCR amplified using two primer pairs specific for a region adjacent the psbD gene (A10, SEQ ID NOs. 27 and 28) and a region adjacent the near the psbH gene (B5, SEQ ID NOs. 787 and 788). Each PCR product was digested with NotI and I-SceI and ligated to pDOCI (SEQ ID NO. 1) that was digested with I-SceI to form pDOCI-B5A10 (SEQ ID NO. 20).

The hybrid gap-filling for capturing chloroplast DNA, pTRP-B5A10, was constructed using recombination in yeast. Briefly, pDOCI-B5A10 (SEQ ID NO. 20) was digested with PacI and AscI to liberate the cassette that introduces chloroplast genome-specific elements into the hybrid gap-filling vector. This cassette was transformed along with pTRP-AU into the yeast strain YPH858 using the lithium acetate method. Homologous recombination takes place in vivo in the transformed yeast cells. Transformants that correctly integrated with cassette were isolated based on growth on CSM-Trp agar media containing 5-fluorooratic acid (5-FOA) and by red color. 5-FOA selects for clones that lack a finctional URA3 gene and the red color results when the ADE2 gene is eliminated. Plasmid DNA was isolated from yeast clones that were grown in CSM-Trp liquid media and transformed into *E. coli* (DH10B). To generate large amounts of pTRP-10-Kan, DH10B cells harboring pTRP-10-Kan were grown to saturation at 37° C. in LB+Kan (50 ug/rML), and then diluted 1:20 in LB+Kan+IPTG and grown for 4 hours at 37° C. DNA was prepared from the bacterial culture using the Plasmid Maxi kit (QIAGEN).

The desired genomic DNA is captured by using the sites in a gap filling vector that have high homology to the regions of the target genomic DNA (indicated by A10 and B5 in FIG. 13). Linearized gap filling vector DNA and chloroplast genome DNA are used to transform *S. cerevisiae* using the lithium acetate or spheroplast methods as described in EXAMPLE 2. Homologous recombination takes place in vivo in the transformed yeast cells. Once the target DNA is captured by the vector via homologous recombination, the DNA can be stably replicated in both yeast and bacterial systems. As indicated in FIG. 1, the gap filling vector contains the selectable marker TRP 1. Therefore, the yeast cells are plated on tryptophan-free medium to screen for positive transformants. Transformed strains growing on the tryptophan-free medium are screened for the presence of target DNA inserts in the gap filling plasmid. Such screening can be by any known method in the art, for example, restriction enzyme digestion, PCR and/or gel electrophoresis.

Yeast transformants screened by PCR using primers specific for chloroplast genome DNA (SEQ IDs 89 and 90). Desired clones are those that give a PCR product of expected size. DNA is prepared from the isolated yeast clones and transformed into bacteria. Bacterial transformants are PCR screened using primers specific for chloroplast genome DNA (SEQ IDs 89 and 90). Desired clones are those that give a PCR product of expected size. DNA is prepared from the isolated bacterial clones and analyzed by restriction digest with EcoRI.

Example 12

Gap-Filling a Complete Chloroplast Genome

Figure 14:
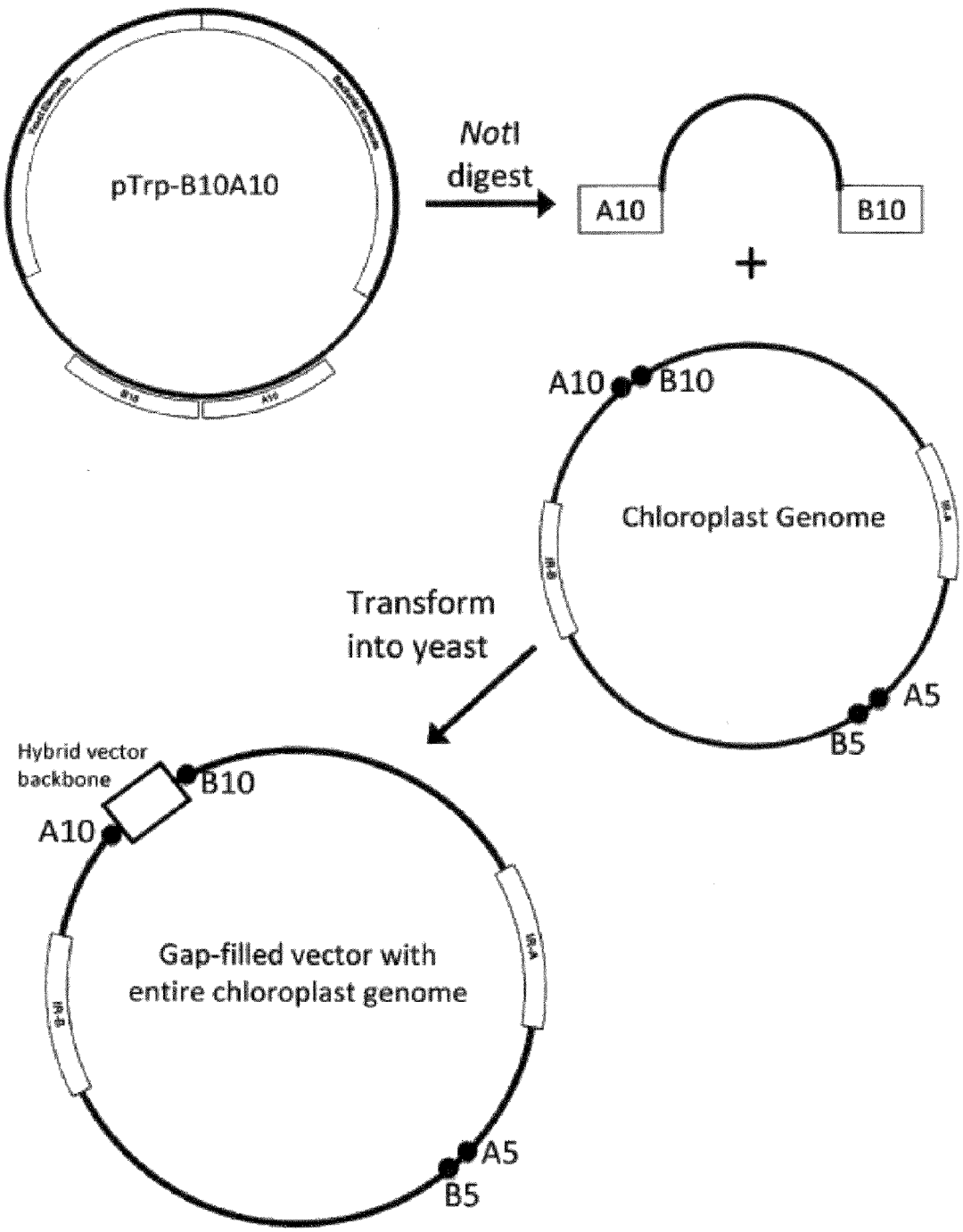
FIG. 14 is a schematic showing capture of an entire chloroplast genome using recombination in yeast.

In this example, a system is established using a hybrid gap-filling vector to capture a complete chloroplast genome by recombination in yeast (FIG. 14). The hybrid gap-filling for capturing chloroplast DNA, pTRP-10, was constructed using recombination in yeast. Briefly, pDOCI-10 (described in EXAMPLE 3, SEQ ID NO. 3) was digested with PacI and AscI to liberate the cassette that introduces chloroplast genome-specific elements into the hybrid gap-filling vector. This cassette was transformed along with pTRP-AU into the yeast strain YPH858 using the lithium acetate method. Homologous recombination takes place in vivo in the transformed yeast cells. Transformants that correctly integrated with cassette were isolated based on growth on CSM-Trp agar media containing 5-fluorooratic acid (5-FOA) and by red color. 5-FOA selects for clones that lack a functional URA3 gene and the red color results when the ADE2 gene is eliminated. Plasmid DNA was isolated from yeast clones that were grown in CSM-Trp liquid media and transformed into E. coli (DH10B). To generate large amounts of pTRP-10-Kan, DH10B cells harboring pTRP-10-Kan were grown to saturation at 37° C. in LB+Kan (50 ug/mL), and then diluted 1:20 in LB+Kan+IPTG and grown for 4 hours at 37° C. DNA was prepared from the bacterial culture using the Plasmid Maxi kit (QIAGEN).

The desired genomic DNA is captured by using the sites in a gap filling vector that have high homology to the adjacent regions of the target genomic DNA (indicated by A10 and B10 in FIG. 14). Linearized gap filling vector DNA and chloroplast genome DNA are used to transform S. cerevisiae using the lithium acetate or spheroplast methods as described in EXAMPLE 2. Homologous recombination takes place in vivo in the transformed yeast cells. Once the target DNA is captured by the vector via homologous recombination, the DNA can be stably replicated in both yeast and bacterial systems. As indicated in FIG. 1, the gap filling vector contains the selectable marker TRP1. Therefore, the yeast cells are plated on tryptophan-free medium to screen for positive transformants. Transformed strains growing on the tryptophan-free medium are screened for the presence of target DNA inserts in the gap filling plasmid. Such screening can be by any known method in the art, for example, restriction enzyme digestion, PCR and/or gel electrophoresis.

Yeast transformants screened by PCR using primers specific for chloroplast genome DNA (SEQ IDs 89 and 90). Desired clones are those that give a PCR product of expected size. DNA is prepared from the isolated yeast clones and transformed into bacteria. Bacterial transformants are PCR screened using primers specific for chloroplast genome DNA (SEQ IDs 89 and 90). Desired clones are those that give a PCR product of expected size. DNA is prepared from the isolated bacterial clones and analyzed by restriction digest with EcoRI.

Example 13

Reassembly on a Complete Chloroplast Genome

Figure 15:
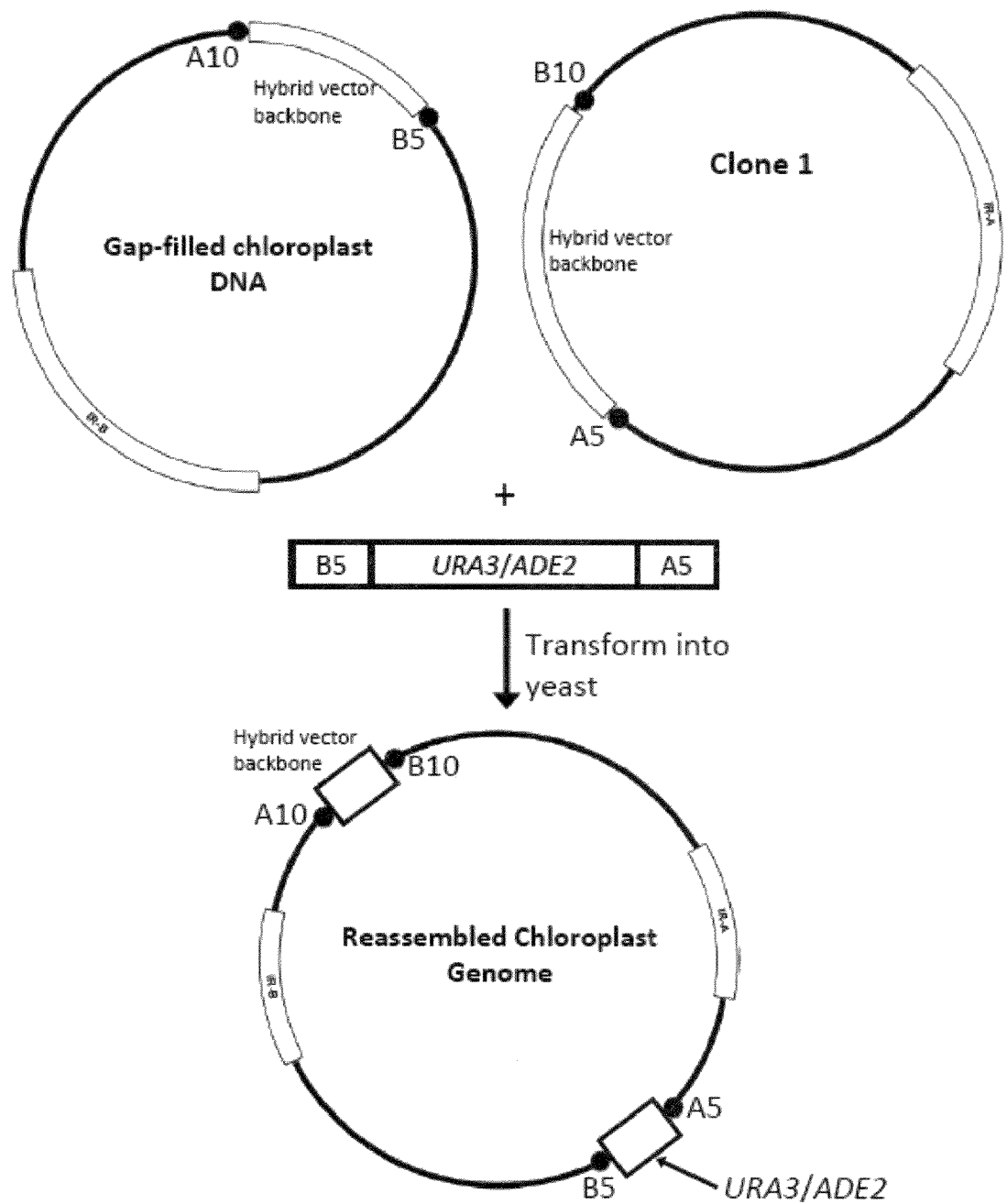
FIG. 15 is a schematic showing reassembly of an entire chloroplast genome using recombination in yeast.

In some instances, the chloroplast genome may be divided into different plasmids, which, in total, comprise the entirety of the genome (FIG. 15). In such instances, capture of smaller portions may facilitate rapid and complex modification of multiple positions within the genome. The chloroplast genome fragments are then combined to reform a complete (and possibly modified) chloroplast genome.

Figure 5:
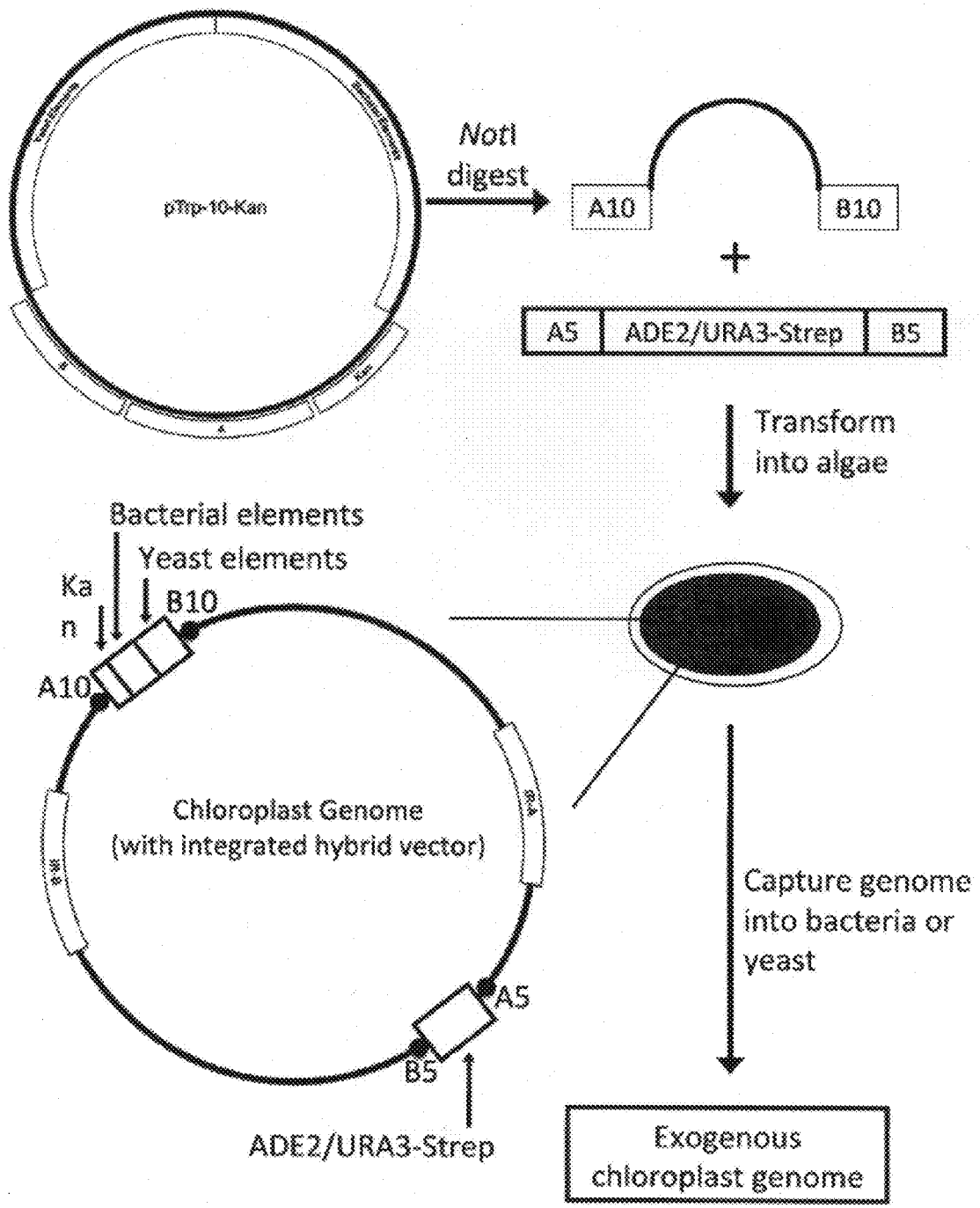
FIG. 5 is a schematic for introduction of hybrid vector into chloroplast genome DNA.

In this example, the chloroplast is divided between two vectors. One vector consists of the chloroplast genome DNA from B5 to A10, or nucleotide 76,400 to 176,500 (according to the sequence available from NCBI, NC_005353), respectively. This vector may be obtained by the procedure describe in EXAMPLE 11. The other vector consists of the chloroplast genome DNA from B10 to A5, or nucleotide 176,500 to 76,400 (according to the sequence available from NCBI, NC_005353), respectively. This vector is the same one as Clone 1 described in may be obtained by the procedure described in EXAMPLE 6. Both vector share the hybrid vector sequence and can use that as a region of homology for recombination. In this example, the recombination event insert the hybrid vector sequenc between regions A10 and B10 (FIG. 5). However, there is no homology sufficient to facilitate recombination that joins regions A5 and B5 (FIG. 5). Thus, a third vector is added that has selectable markers between sequences homologous to A5 and B5.

The chloroplast genome is reassembled by combining all three vectors and transforming S. cerevisiae using the lithium acetate or spheroplast methods as described in EXAMPLE 2. Homologous recombination takes place in vivo in the transformed yeast cells. Once the target DNA is created via homologous recombination, the DNA can be stably replicated in both yeast and bacterial systems. As indicated in FIG. 15, the third vector contains the selectable markers URA3 and ADE2. Therefore, the yeast cells are plated on tryptophan-free medium to screen for positive transformants. Transformed strains growing on the uracil and/or adenine-free medium are screened for the presence of target DNA inserts in the gap filling plasmid. Such screening can be by any known method in the art, for example, restriction enzyme digestion, PCR and/or gel electrophoresis.

Yeast transformants screened by PCR using primers specific for chloroplast genome DNA (SEQ IDs 89 and 90). Desired clones are those that give a PCR product of expected size. DNA is prepared from the isolated yeast clones and transformed into bacteria. Bacterial transformants are PCR screened using primers specific for chloroplast genome DNA (SEQ IDs 89 and 90). Desired clones are those that give a PCR product of expected size. DNA is prepared from the isolated bacterial clones and analyzed by restriction digest with EcoRI.

Example 14

Vectors and Methods to Remove Regions Chloroplast Genome DNA in an Exogenous Host To generate vectors that remove regions of chloroplast genome DNA, 800-1000 bp regions of chloroplast DNA are amplified using PCR primer pairs that anneal to 5' and 3' regions flanking the sites indicated in FIG. 4 (site 1-5', SEQ ID NOs. 1079 and 1080; site 1-3', SEQ ID NOs. 1125 and 1126; site 3-5', SEQ ID NOs. 1083 and 1084; site 3-3', SEQ ID NOs. 1129 and 1130; site 4-5', SEQ ID NOs. 1087 and 1088; site 4-3', SEQ ID NOs. 1133 and 1134; site 5-5', SEQ ID NOs. 789 and 790; site 5-3', SEQ ID NOs. 787 and 788; and site 7-5', SEQ ID NOs. 1091 and 1092; site 7-3', SEQ ID NOs. 1089 and 1090). Pairs of PCR products from the 5' and 3' regions for different sites are digested with NotI and I-SceI, mixed, and ligated to NotI-digested pUC-SE (SEQ ID NO. 2). Pairs of yeast selection markers (described in EXAMPLE 4) are cloned between the 5' and 3' fragments using SalI.

Regions of chloroplast genome DNA are removed by transforming the deletion vector into yeast that harbor the captured DNA. For transformation, all modification vectors were linearized by digestion with NotI. Yeast harboring the desired clone are grown to saturation in CSM-Trp media at 30° C., then diluted 1:20 in YPAD and grown for 4 hours at 30° C. Yeast were transformed using the lithium-acetate method and transformants were selected for by growth on CSM-Ura media. Transformants were propagated on CSM-Trp-Ura media and then PCR screened using primers specific for the targeted region and a region of the chloroplast genome DNA not targeted by the deletion vector. Desired clones are those that give not product for the targeted region, but do give a PCR product of expected size for the untargeted area. DNA is prepared from the isolated yeast clones and transformed into bacteria. Bacteria PCR screened using primers specific for the targeted region and a region of the chloroplast genome DNA not targeted by the deletion vector. Desired clones are those that give not product for the targeted region, but do give a PCR product of expected size for the untargeted area. DNA is prepared from the isolated bacterial clones and analyzed by restriction digest.

Various modifications, processes, as well as numerous structures that may be applicable herein will be apparent. Various aspects, features or embodiments may have been explained or described in relation to understandings, beliefs, theories, underlying assumptions, and/or working or prophetic examples, although it will be understood that any particular understanding, belief, theory, underlying assumption, and/or working or prophetic example is not limiting. Although the various aspects and features may have been described with respect to various embodiments and specific examples herein, it will be understood that any of same is not limniting with respect to the full scope of the appended claims or other claims that may be associated with this application.

What is claimed is:

1. A plurality of vectors for assembling a circular chloroplast genome, comprising
   a plurality of vectors, each comprising at least 20 kb of chloroplast DNA, and collectively comprising all chloroplast genes necessary to carry out photosynthesis;
   wherein each vector in said plurality of vectors comprises two regions for homologous recombination with one or two other vectors in said plurality of vectors,
   wherein at least one vector of said plurality of vectors comprises a yeast DNA replication element and at least one vector of said plurality of vectors comprises a bacterial DNA replication element, wherein said vectors comprising said yeast and bacterial DNA replication elements can be the same or different, and
   wherein at least one vector of said plurality of vectors comprises a yeast stability element comprising at least one yeast selection marker and said at least one vector comprising a stability element does not contain a yeast DNA replication element.

2. The plurality of vectors of claim 1, wherein said plurality of vectors comprises two vectors and each of said vectors comprise two areas for homologous recombination with each other.

3. The plurality of vectors of claim 1, wherein said yeast DNA replication element is a yeast centromere, a yeast autonomous replicating sequence, or both.

4. The plurality of vectors of claim 1, wherein said bacterial DNA replication element is a P1 replication sequence or an F factor replication sequence.

5. The plurality of vectors of claim 1, wherein at least one of said plurality of vectors comprises a single yeast DNA replication element.

6. The plurality of vectors of claim 5, wherein said yeast DNA replication element and said bacterial DNA replication element are contained in the same vector.

7. The plurality of vectors of claim 1, wherein said the chloroplast DNA when assembled into a circular chloroplast genome contains at least 140 kb of DNA.

8. The plurality of vectors of claim 1, wherein at least one of said vectors comprises chemically synthesized DNA.

9. The plurality of vectors of claim 1, wherein at least one of said vectors comprises genomic chloroplast DNA from a photosynthetic organism.

10. The plurality of vectors of claim 9, wherein said genomic chloroplast DNA from a photosynthetic organism comprises at least one modification.

11. The plurality of vectors of claim 10, wherein said at least one modification is insertion of a heterologous or homologous polynucleotide, deletion of one or more nucleic acid bases, insertion of one or more nucleic acid bases, mutation of one or more nucleic acid bases, rearrangement of one or more polynucleotides, or any combination thereof.

12. The plurality of vectors of claim 1, wherein said yeast stability element comprises a pair of yeast selection markers.

13. The plurality of vectors of claim 12, wherein said pair of yeast selection markers is a URA3 gene and an additional yeast selection marker.

14. The plurality of vectors of claim 13, wherein said additional yeast selection marker is an ADE gene, a LEU gene, a HIS gene, a LYS gene or a G418 gene.

15. The plurality of vectors of claim 12, wherein for each vector comprising a yeast stability element, said yeast stability element comprises a different pair of yeast selection markers.

16. A fungal or bacterial host organism comprising the plurality of vectors of claim 1.

17. A method of assembling a circular chloroplast genome, comprising
   obtaining a plurality of vectors, each vector comprising at least 20 kb of chloroplast DNA, and collectively comprising all chloroplast genes necessary to carry out photosynthesis;
   wherein each vector in said plurality of vectors comprises two regions for homologous recombination with one or two other vectors in said plurality of vectors,
   wherein at least one vector of said plurality of vectors comprises a yeast DNA replication element and at least one vector of said plurality of vectors comprises a bacterial DNA replication element, wherein said vectors comprising said yeast and bacterial DNA replication elements can be the same or different, and
   wherein at least one vector of said plurality of vectors comprises a yeast stability element comprising at least one yeast selection marker and said at least one vector comprising a stability element does not contain a yeast DNA replication element;

introducing said plurality of vectors into yeast to assemble said plurality of vectors by homologous recombination to produce an assembled circular chloroplast genome; and selecting for complete assembly of said circular chloroplast genome by selecting for the presence of said at least one stability element.

18. The method of claim 17, wherein said plurality of vectors comprises two vectors and each of said vectors comprise two areas for homologous recombination with each other.

19. The method of claim 17, wherein said yeast DNA replication element is a yeast centromere, a yeast autonomous replicating sequence, or both.

20. The method of claim 17, wherein said bacterial DNA replication element is a P1 replication sequence or an F factor replication sequence.

21. The method of claim 17, wherein at least one of said plurality of vectors comprises a single yeast DNA replication element.

22. The method of claim 17, wherein said yeast DNA replication element and said bacterial DNA replication element are contained in the same vector.

23. The method of claim 17, wherein said chloroplast DNA when assembled into a circular chloroplast genome contains at least 140 kb of DNA.

24. The method of claim 17, where at least one of said vectors comprises chemically synthesized DNA.

25. The method of claim 17, wherein at least one of said vectors comprises genomic chloroplast DNA from a photosynthetic organism.

26. The method of claim 25, wherein said photosynthetic organism is an alga.

27. The method of claim 25, wherein said genomic chloroplast DNA from a photosynthetic organism comprises at least one modification.

28. The method of claim 27, wherein said at least one modification is insertion of a heterologous or homologous polynucleotide, deletion of one or more nucleic acid bases, insertion of one or more nucleic acid bases, mutation of one or more nucleic acid bases, rearrangement of one or more polynucleotides, or any combination thereof.

29. The method of claim 17, wherein said yeast stability element comprises a pair of yeast selection markers.

30. The method of claim 29, wherein said pair of yeast selection markers is a URA3 gene and an additional yeast selection marker.

31. The method of claim 30, wherein said additional yeast selection marker is an ADE gene, a LEU gene, a HIS gene, a LYS gene or a G418 gene.

32. The method of claim 29, wherein for each vector comprising a yeast stability element, said yeast stability element comprises a different pair of yeast selection markers.

33. The method of claim 17, further comprising introducing said assembled circular chloroplast genome into an algal, plant, or cyanobacteria host organism.

34. The method of claim 17, further comprising removing said at least one stability element following selection for complete assembly of said circular chloroplast genome.

* * * * *

SEQUENCE LISTING

```
<160> NUMBER OF SEQ ID NOS: 99

<210> SEQ ID NO 1
<211> LENGTH: 4572
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tcgtgtagat aactacgata cgggagggct taccatctgg ccccagtgct gcaatgatac      60
cgcgagaccc acgctcaccg gctccagatt tatcagcaat aaaccagcca gccggaaggg     120
ccgagcgcag aagtggtcct gcaactttat ccgcctccat ccagtctatt aattgttgcc     180
gggaagctag agtaagtagt tcgccagtta atagtttgcg caacgttgtt gccattgcta     240
caggcatcgt ggtgtcacgc tcgtcgtttg gtatggcttc attcagctcc ggttcccaac     300
gatcaaggcg agttacatga tcccccatgt tgtgcaaaaa agcggttagc tccttcggtc     360
ctccgatcgt tgtcagaagt aagttggccg cagtgttatc actcatggtt atggcagcac     420
tgcataattc tcttactgtc atgccatccg taagatgctt ttctgtgact ggtgagtact     480
caaccaagtc attctgagaa tagtgtatgc ggcgaccgag ttgctcttgc ccggcgtcaa     540
tacgggataa taccgcgcca catagcagaa ctttaaaagt gctcatcatt ggaaaacgtt     600
cttcggggcg aaaactctca aggatcttac cgctgttgag atccagttcg atgtaaccca     660
ctcgtgcacc caactgatct tcagcatctt ttactttcac cagcgtttct gggtgagcaa     720
aaacaggaag gcaaaatgcc gcaaaaaagg gaataagggc gacacggaaa tgttgaatac     780
tcatactctt ccttttcaa tattattgaa gcatttatca gggttattgt ctcatgagcg     840
gatacatatt tgaatgtatt tagaaaaata aacaaatagg ggttccgcgc acatttcccc     900
```

```
gaaaagtgcc acctgacgtc taagaaacca ttattatcat gacattaacc tataaaaata    960
ggcgtatcac gaggcccttt cgtctcgcgc gtttcggtga tgacggtgaa aacctctgac   1020
acatgcagct cccggagacg gtcacagctt gtctgtaagc ggatgccggg agcagacaag   1080
cccgtcaggg cgcgtcagcg ggtgttggcg ggtgtcgggg ctggcttaac tatgcggcat   1140
cagagcagat tgtactgaga gtgcaccata gggcggccgc ggcgcgccgt tccggatctg   1200
catcctgcga tgcagatccg gaacataatg gtgcagggcg ctgacttccg cgtttccaga   1260
ctttacgaaa cacggaaacc gaagaccatt catgttgttg ctcaggtcgc agacgttttg   1320
cagcagcagt cgcttcacgt tcgctcgcgt atcggtgatt cattctgcta accagtaagg   1380
caaccccgcc agcctagccg ggtcctcaac gacaggagca cgatcatgcg cacccgtggc   1440
caggacccaa cgctgcccga gatgcgccgc gtgcggctgc tggagatggc ggacgcgatg   1500
gatatgttct gccaagggtt ggtttgcgca ttcacagttc tccgcaagaa ttgattggct   1560
ccaattcttg gagtggtgaa tccgttagcg aggtgccgcc ggcttccatt caggtcgagg   1620
tggcccggct ccatgcaccg cgacgcaacg cggggaggca gacaaggtat agggcggcgc   1680
ctacaatcca tgccaacccg ttccatgtgc tcgccgaggc ggcataaatc gccgtgacga   1740
tcagcggtcc aatgatcgaa gttaggctgg taagagccgc gagcgatcct tgaagctgtc   1800
cctgatggtc gtcatctacc tgcctggaca gcatggcctg caacgcgggc atcccgatgc   1860
cgccggaagc gagaagaatc ataatgggga aggccatcca gcctcgcgtc gcgaacgcca   1920
gcaagacgta gcccagcgcg tcggccgcca tgccggcgat aatggcctgc ttctcgccga   1980
aacgtttggt ggcgggacca gtgacgaagg cttgagcgag ggcgtgcaag attccgaata   2040
ccgcaagcga caggccgatc atcgtcgcgc tccagcgaaa gcggtcctcg ccgaaaatga   2100
cccagagcgc tgccggcacc tgtcctacga gttgcatgat aaagaagaca gtcataagtg   2160
cggcgacgat agtcatgccc cgcgcccacc ggaaggagct gactgggttg aaggctctca   2220
agggcatcgg tcgagcttga cattgtagga cgtttaaaca ttaccctgtt atccctaggc   2280
cggcctaaga aaccattatt atcatgacat taacctataa aataggcgt atcacgaggc   2340
cctttcgtct tcaagaaatt cggtcgaaaa aagaaaagga gagggccaag agggagggca   2400
ttggtgacta ttgagcacgt gagtatacgt gattaagcac acaaaggcag cttggagtat   2460
gtctgttatt aatttcacag gtagttctgg tccattggtg aaagtttgcg gcttgcagag   2520
cacagaggcc gcagaatgtg ctctagattc cgatgctgac ttgctgggta ttatatgtgt   2580
gcccaataga aagagaacaa ttgacccggt tattgcaagg aaaatttcaa gtcttgtaaa   2640
agcatataaa aatagttcag gcactccgaa atacttggtt ggcgtgtttc gtaatcaacc   2700
taaggaggat gttttggctc tggtcaatga ttacggcatt gatatcgtcc aactgcatgg   2760
agatgagtcg tggcaagaat accaagagtt cctcggtttg ccagttatta aaagactcgt   2820
atttccaaaa gactgcaaca tactactcag tgcagcttca cagaaacctc attcgtttat   2880
tcccttgttt gattcagaag caggtgggac aggtgaactt ttggattgga actcgatttc   2940
tgactgggtt ggaaggcaag agagcccga aagcttacat tttatgttag ctggtggact   3000
gacgccagaa aatgttggtg atgcgcttag attaaatggc gttattggtg ttgatgtaag   3060
cggaggtgtg gagacaaatg gtgtaaaaga ctctaacaaa atagcaaatt tcgtcaaaaa   3120
tgctaagaaa taggttatta ctgagtagta tttatttaag tattgtttgt gcacttgcct   3180
gcaggccttt tgaaaagcaa gcataaaaga tctaaacata aaatctgtaa aataacaaga   3240
tgtaaagata atgctaaatc atttggcttt ttgattgatt gtacaggaaa atatacatcg   3300
```

-continued

```
ttaattaagc ggccgcgagc ttggcgtaat catggtcata gctgtttcct gtgtgaaatt    3360
gttatccgct cacaattcca cacaacatac gagccggaag cataaagtgt aaagcctggg    3420
gtgcctaatg agtgagctaa ctcacattaa ttgcgttgcg ctcactgccc gctttccagt    3480
cgggaaacct gtcgtgccag ctgcattaat gaatcggcca acgcgcgggg agaggcggtt    3540
tgcgtattgg gcgctcttcc gcttcctcgc tcactgactc gctgcgctcg tcgttcggc    3600 tgcggcgagc ggtatcagct cactcaaagg cggtaatacg gttatccaca gaatcagggg    3660
ataacgcagg aaagaacatg tgagcaaaag gccagcaaaa ggccaggaac cgtaaaaagg    3720
ccgcgttgct ggcgttttc cataggctcc gcccccctga cgagcatcac aaaaatcgac    3780
gctcaagtca gaggtggcga aacccgacag gactataaag ataccaggcg tttccccctg    3840
gaagctccct cgtgcgctct cctgttccga cctgccgct taccggatac ctgtccgcct    3900
ttctcccttc gggaagcgtg gcgctttctc atagctcacg ctgtaggtat ctcagttcgg    3960
tgtaggtcgt tcgctccaag ctgggctgtg tgcacgaacc ccccgttcag cccgaccgct    4020
gcgccttatc cggtaactat cgtcttgagt ccaacccggt aagacacgac ttatcgccac    4080
tggcagcagc cactggtaac aggattagca gagcgaggta tgtaggcggt gctacagagt    4140
tcttgaagtg gtggcctaac tacggctaca ctagaagaac agtatttggt atctgcgctc    4200
tgctgaagcc agttaccttc ggaaaaagag ttggtagctc ttgatccggc aaacaaacca    4260
ccgctggtag cggtggtttt tttgtttgca agcagcagat tacgcgcaga aaaaaggat    4320 ctcaagaaga tcctttgatc ttttctacgg ggtctgacgc tcagtggaac gaaaactcac    4380
gttaagggat tttggtcatg agattatcaa aaaggatctt cacctagatc cttttaaatt    4440
aaaaatgaag ttttaaatca atctaaagta tatatgagta aacttggtct gacagttacc    4500
aatgcttaat cagtgaggca cctatctcag cgatctgtct atttcgttca tccatagttg    4560
cctgactccc cg                                                        4572
```

<210> SEQ ID NO 2
<211> LENGTH: 2474
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatagggc ggccgccagc tggaattcta cgtactgcag agtactgcgg ccgcgagctt     240
ggcgtaatca tggtcatagc tgtttcctgt gtgaaattgt tatccgctca caattccaca     300
caacatacga gccggaagca taagtgtaa agcctggggt gcctaatgag tgagctaact     360
cacattaatt gcgttgcgct cactgcccgc tttccagtcg ggaaacctgt cgtgccagct     420
gcattaatga atcggccaac gcgcggggag aggcggtttg cgtattgggc gctcttccgc     480
ttcctcgctc actgactcgc tgcgctcggt cgttcggctg cggcgagcgg tatcagctca     540
ctcaaaggcg gtaatacggt tatccacaga atcagggat aacgcaggaa agaacatgtg     600
agcaaaaggc cagcaaaagg ccaggaaccg taaaaaggcc gcgttgctgg cgtttttcca     660
taggctccgc ccccctgacg agcatcacaa aaatcgacgc tcaagtcaga ggtggcgaaa     720
cccgacagga ctataaagat accaggcgtt tccccctgga agctccctcg tgcgctctcc     780
```

```
tgttccgacc ctgccgctta ccggatacct gtccgccttt ctcccttcgg aagcgtggc      840 gctttctcat agctcacgct gtaggtatct cagttcggtg taggtcgttc gctccaagct     900
gggctgtgtg cacgaacccc ccgttcagcc cgaccgctgc gccttatccg gtaactatcg     960
tcttgagtcc aacccggtaa gacacgactt atcgccactg gcagcagcca ctggtaacag    1020
gattagcaga gcgaggtatg taggcggtgc tacagagttc ttgaagtggt ggcctaacta    1080
cggctacact agaagaacag tatttggtat ctgcgctctg ctgaagccag ttaccttcgg    1140
aaaaagagtt ggtagctctt gatccggcaa acaaaccacc gctggtagcg gtggtttttt    1200
tgtttgcaag cagcagatta cgcgcagaaa aaaggatcc caagaagatc ctttgatctt     1260
ttctacgggg tctgacgctc agtggaacga aaactcacgt taagggattt tggtcatgag    1320
attatcaaaa aggatcttca cctagatcct tttaaattaa aaatgaagtt ttaaatcaat    1380
ctaaagtata tatgagtaaa cttggtctga cagttaccaa tgcttaatca gtgaggcacc    1440
tatctcagcg atctgtctat ttcgttcatc catagttgcc tgactccccg tcgtgtagat    1500
aactacgata cgggagggct taccatctgg ccccagtgct gcaatgatac cgcgagaccc    1560
acgctcaccg gctccagatt tatcagcaat aaaccagcca gccggaaggg ccgagcgcag    1620
aagtggtcct gcaactttat ccgcctccat ccagtctatt aattgttgcc gggaagctag    1680
agtaagtagt tcgccagtta atagtttgcg caacgttgtt gccattgcta caggcatcgt    1740
ggtgtcacgc tcgtcgtttg gtatggcttc attcagctcc ggttcccaac gatcaaggcg    1800
agttacatga tcccccatgt tgtgcaaaaa agcggttagc tccttcggtc ctccgatcgt    1860
tgtcagaagt aagttggccg cagtgttatc actcatggtt atggcagcac tgcataattc    1920
tcttactgtc atgccatccg taagatgctt ttctgtgact ggtgagtact caaccaagtc    1980
attctgagaa tagtgtatgc ggcgaccgag ttgctcttgc ccggcgtcaa tacgggataa    2040
taccgcgcca catagcagaa ctttaaaagt gctcatcatt ggaaaacgtt cttcggggcg    2100
aaaactctca aggatcttac cgctgttgag atccagttcg atgtaaccca ctcgtgcacc    2160
caactgatct tcagcatctt ttactttcac cagcgtttct gggtgagcaa aaacaggaag    2220
gcaaaatgcc gcaaaaaagg aataagggc gacacggaaa tgttgaatac tcatactctt    2280 ccttttcaa tattattgaa gcatttatca gggttattgt ctcatgagcg gatacatatt     2340
tgaatgtatt tagaaaaata aacaaatagg ggttccgcgc acatttcccc gaaaagtgcc    2400
acctgacgtc taagaaacca ttattatcat gacattaacc tataaaaata ggcgtatcac    2460
gaggcccttt cgtc                                                      2474
```

<210> SEQ ID NO 3
<211> LENGTH: 6638
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
tcgtgtagat aactacgata cgggagggct taccatctgg ccccagtgct gcaatgatac     60
cgcgagaccc acgctcaccg gctccagatt tatcagcaat aaaccagcca gccggaaggg    120
ccgagcgcag aagtggtcct gcaactttat ccgcctccat ccagtctatt aattgttgcc    180
gggaagctag agtaagtagt tcgccagtta atagtttgcg caacgttgtt gccattgcta    240
caggcatcgt ggtgtcacgc tcgtcgtttg gtatggcttc attcagctcc ggttcccaac    300
```

```
gatcaaggcg agttacatga tcccccatgt tgtgcaaaaa agcggttagc tccttcggtc    360
ctccgatcgt tgtcagaagt aagttggccg cagtgttatc actcatggtt atggcagcac    420
tgcataattc tcttactgtc atgccatccg taagatgctt ttctgtgact ggtgagtact    480
caaccaagtc attctgagaa tagtgtatgc ggcgaccgag ttgctcttgc ccggcgtcaa    540
tacgggataa taccgcgcca catagcagaa ctttaaaagt gctcatcatt ggaaaacgtt    600
cttcggggcg aaaactctca aggatcttac cgctgttgag atccagttcg atgtaaccca    660
ctcgtgcacc caactgatct tcagcatctt ttactttcac cagcgtttct gggtgagcaa    720
aaacaggaag gcaaaatgcc gcaaaaaagg gaataagggc gacacggaaa tgttgaatac    780
tcatactctt cctttttcaa tattattgaa gcatttatca gggttattgt ctcatgagcg    840
gatacatatt tgaatgtatt tagaaaaata aacaatagg ggttccgcgc acatttcccc    900
gaaaagtgcc acctgacgtc taagaaacca ttattatcat gacattaacc tataaaaata    960
ggcgtatcac gaggcccttt cgtctcgcgc gtttcggtga tgacggtgaa aacctctgac   1020
acatgcagct cccggagacg gtcacagctt gtctgtaagc ggatgccggg agcagacaag   1080
cccgtcaggg cgcgtcagcg ggtgttggcg ggtgtcgggg ctggcttaac tatgcggcat   1140
cagagcagat tgtactgaga gtgcaccata gggcggccgc ggcgcgccgt tccggatctg   1200
catcctgcga tgcagatccg gaacataatg gtgcagggcg ctgacttccg cgttccaga    1260 ctttacgaaa cacggaaacc gaagaccatt catgttgttg ctcaggtcgc agacgttttg   1320
cagcagcagt cgcttcacgt tcgctcgcgt atcggtgatt cattctgcta accagtaagg   1380
caaccccgcc agcctagccg ggtcctcaac gacaggagca cgatcatgcg cacccgtggc   1440
caggacccaa cgctgcccga gatgcgccgc gtgcggctgc tggagatggc ggacgcgatg   1500
gatatgttct gccaagggtt ggtttgcgca ttcacagttc tccgcaagaa ttgattggct   1560
ccaattcttg gagtggtgaa tccgttagcg aggtgccgcc ggcttccatt caggtcgagg   1620
tggcccggct ccatgcaccg cgacgcaacg cggggaggca gacaaggtat agggcggcgc   1680
ctacaatcca tgccaacccg ttccatgtgc tcgccgaggc ggcataaatc gccgtgacga   1740
tcagcggtcc aatgatcgaa gttaggctgg taagagccgc gagcgatcct tgaagctgtc   1800
cctgatggtc gtcatctacc tgcctggaca gcatggcctg caacgcgggc atcccgatgc   1860
cgccggaagc gagaagaatc ataatgggga aggccatcca gcctcgcgtc gcgaacgcca   1920
gcaagacgta gcccagcgcg tcggccgcca tgccggcgat aatggcctgc ttctcgccga   1980
aacgtttggt ggcgggacca gtgacgaagg cttgagcgag ggcgtgcaag attccgaata   2040
ccgcaagcga caggccgatc atcgtcgcgc tccagcgaaa gcggtcctcg ccgaaaatga   2100
cccagagcgc tgccggcacc tgtcctacga gttgcatgat aaagaagaca gtcataagtg   2160
cggcgacgat agtcatgccc cgcgcccacc ggaaggagct gactgggttg aaggctctca   2220
agggcatcgg tcgagcttga cattgtagga cgtttaaaca ttaccctgtt atccctagga   2280
tcctacgtat acatactccg aaggaggaca aatttattta ttgtggtaca ataaataagt   2340
ggtacaataa ataaattgta tgtaaacccc ttccccttcg ggacgtcccc ttacgggaat   2400
ataaatatta gtggcagttg cctgccaaca aatttattta ttgtattaac ataggcagtg   2460
gcggtaccac tgccactggc gtcctaatat aaatatggg caactaaagt ttatcgcagt   2520
attaacatag gcagtggcgg taccactgcc actggcgtcc ccttcggag tatgtaaacc   2580 tgctaccgca gcaaataaat ttattctat tttaatacta caatatttag attcccgtta   2640
ggggataggc caggcaattg tcactggcgt catagtatat caatattgta acagattgac   2700
```

```
acccttttaag taaacatttt ttttaggatt catatgaaat taaatggata tttggtacat    2760
ttaattccac aaaaatgtcc aatacttaaa atacaaaatt aaaagtatta gttgtaaact    2820
tgactaacat tttaaatttt aaatttttc ctaattatat atttacttg caaaatttat      2880
aaaaatttta tgcatttta tatcataata ataaaaccttt tattcatggt ttataatata    2940
ataattgtga tgactatgca caaagcagtt ctagtcccat atataaact atatataacc     3000
cgtttaaaga tttattaaa aatatgtgtg taaaaaatgc ttatttttaa ttttatttta     3060
tataagttat aatattaaat acacaatgat taaaattaaa taataataaa tttaacgtaa    3120
cgatgagttg tttttttatt ttggagatac acgcaatgac aattgcgatc ggtacatatc    3180
aagagaaacg cacatggttc gatgacgctg atgactggct tcgtcaagac cgtttcgtat    3240
tcgtaggttg gtcaggttta ttactattcc cttgtgctta ctttgcaact ccggtccggc    3300
ggccgcctcg agacgacttg tccgcttcat cagacacggc tttcctaacc atcaatggtg    3360
gattttcagg aaagacgttt aaagaagtgg cataaagttt atttgttgaa gaattggttt    3420
tgtttccatt caaagaattg ttagggataa aactttgcat tttttttataa tttgttataa   3480
gtttttcaaa cttatatgtt tttaaaaatg catttaattg cttattaatg cgttcatttt    3540
gtaatgtttc aataggtctt gcttgcgcta atcgcagtat tcccgatact ttgtctgctt    3600
gttttttcggg tattgagaat aagtaagtat aatgatttaa aaagtcatg ttttgattaa    3660
atcttttta tatggttaaa aacattatgg tatatctaaa taaatttatt ttttactaaa    3720
tctccaattt gcaatttaga gatataatta aaactataaa gttatttaag ttaattttgta  3780
atcaaatcca acacaaaaat gtttttatat agttaacatg ttaaatttaa catatgttaa   3840
acaactaaaa ttctgtaaca gagaacaata aaataaatgc tagattttgt gtaatgccga   3900
agtatattta tacttcccc tttcaaaaaa ataaatactc ttgccactaa aattcatttg    3960
cctaggacgt ccccttcccc ttacgggatg tttatatact aggacgtccc cttcccctta   4020
cgggatattt atatactccg aaggacgtcc ccttcgggca aataaatttt agtggcagtt   4080
gcctgccaac tgcctaggca agtaaactta gggattttaa tgcaataaat aaatttgtcc   4140
ccttacggga cgtcagtggc agttgcctgc caactgccta atataaatat tagtggatat   4200
ttatatactc cgaaggaggc agttacctgc caactgccga ggcaaataaa ttttagtggc   4260
agtggtaccg ccactgcctg ctccctcctt cccttcggg caagtaaact tagcatgttg    4320
tcgacattac cctgttatcc ctaggccggc ctaagaaacc attattatca tgacattaac   4380
ctataaaaat aggcgtatca cgaggcccctt tcgtcttcaa gaaattcggt cgaaaaaaga  4440
aaaggagagg gccaagaggg agggcattgg tgactattga gcacgtgagt atacgtgatt   4500
aagcacacaa aggcagcttg gagtatgtct gttattaatt tcacaggtag ttctggtcca   4560
ttggtgaaag tttgcggctt gcagagcaca gaggccgcag aatgtgctct agattccgat   4620
gctgacttgc tgggtattat atgtgtgccc aatagaaaga gaacaattga cccgttatt   4680
gcaaggaaaa tttcaagtct tgtaaaagca tataaaaata gttcaggcac tccgaaatac   4740
ttggttggcg tgtttcgtaa tcaacctaag gaggatgttt tggctctggt caatgattac    4800
ggcattgata tcgtccaact gcatggagat gagtcgtggc aagaatacca agagttcctc   4860
ggtttgccag ttattaaaag actcgtattt ccaaaagact gcaacatact actcagtgca   4920
gcttcacaga aacctcattc gtttattccc ttgtttgatt cagaagcagg tgggacaggt   4980
gaacttttgg attggaactc gatttctgac tgggttggaa ggcaagagag ccccgaaagc   5040
ttacatttta tgttagctgg tggactgacg ccagaaaatg ttggtgatgc gcttagatta   5100
```

```
aatggcgtta ttggtgttga tgtaagcgga ggtgtggaga caaatggtgt aaaagactct     5160
aacaaaatag caaatttcgt caaaaatgct aagaaatagg ttattactga gtagtattta     5220
tttaagtatt gtttgtgcac ttgcctgcag gccttttgaa aagcaagcat aaaagatcta     5280
aacataaaat ctgtaaaata caagatgta aagataatgc taaatcattt ggcttttga      5340 ttgattgtac aggaaaatat acatcgttaa ttaagcggcc gcgagcttgg cgtaatcatg     5400
gtcatagctg tttcctgtgt gaaattgtta tccgctcaca attccacaca acatacgagc     5460
cggaagcata aagtgtaaag cctggggtgc ctaatgagtg agctaactca cattaattgc     5520
gttgcgctca ctgcccgctt tccagtcggg aaacctgtcg tgccagctgc attaatgaat     5580
cggccaacgc gcggggagag gcggtttgcg tattgggcgc tcttccgctt cctcgctcac     5640
tgactcgctg cgctcggtcg ttcggctgcg gcgagcggta tcagctcact caaaggcggt     5700
aatacggtta tccacagaat caggggataa cgcaggaaag aacatgtgag caaaaggcca     5760
gcaaaaggcc aggaaccgta aaaaggccgc gttgctggcg tttttccata ggctccgccc     5820
ccctgacgag catcacaaaa atcgacgctc aagtcagagg tggcgaaacc cgacaggact     5880
ataaagatac caggcgtttc ccctggaag ctccctcgtg cgctctcctg ttccgaccct      5940
gccgcttacc ggatacctgt ccgcctttct cccttcggga agcgtggcgc tttctcatag     6000
ctcacgctgt aggtatctca gttcggtgta ggtcgttcgc tccaagctgg gctgtgtgca     6060 cgaaccccc gttcagcccg accgctgcgc cttatccggt aactatcgtc ttgagtccaa       6120
cccggtaaga cacgacttat cgccactggc agcagccact ggtaacagga ttagcagagc     6180
gaggtatgta ggcggtgcta cagagttctt gaagtggtgg cctaactacg gctacactag     6240
aagaacagta tttggtatct gcgctctgct gaagccagtt accttcggaa aaagagttgg     6300
tagctcttga tccggcaaac aaaccaccgc tggtagcggt ggtttttttg tttgcaagca     6360
gcagattacg cgcagaaaaa aaggatctca agaagatcct ttgatctttt ctacggggtc     6420
tgacgctcag tggaacgaaa actcacgtta agggattttg gtcatgagat tatcaaaaag     6480
gatcttcacc tagatccttt taaattaaaa atgaagtttt aaatcaatct aaagtatata     6540
tgagtaaact tggtctgaca gttaccaatg cttaatcagt gaggcaccta tctcagcgat     6600
ctgtctattt cgttcatcca tagttgcctg actccccg                             6638
```

<210> SEQ ID NO 4
<211> LENGTH: 7855
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
gtgcactctc agtacaatct gctctgatgc cgcatagtta agccagcccc gacacccgcc      60
aacacccgct gacgcgccct gacgggcttg tctgctcccg gcatccgctt acagacaagc     120
tgtgaccgtc tccgggagct gcatgtgtca gaggttttca ccgtcatcac cgaaacgcgc     180
gagacgaaag ggcctcgtga tacgcctatt tttataggtt aatgtcatga taataatggt     240
ttcttagacg tcaggtggca cttttcgggg aaatgtgcgc ggaacccta tttgtttatt      300 tttctaaata cattcaaata tgtatccgct catgagacaa taaccctgat aaatgcttca     360
ataatattga aaaggaaga gtatgagtat tcaacatttc cgtgtcgccc ttattccctt      420
ttttgcggca ttttgccttc ctgttttgc tcacccagaa acgctggtga agtaaaaga       480 tgctgaagat cagttgggtg cacagagtggg ttacatcgaa ctggatctca acagcggtaa     540
```

```
gatccttgag agttttcgcc ccgaagaacg ttttccaatg atgagcactt ttaaagttct    600
gctatgtggc gcggtattat cccgtattga cgccgggcaa gagcaactcg gtcgccgcat    660
acactattct cagaatgact tggttgagta ctcaccagtc acagaaaagc atcttacgga    720
tggcatgaca gtaagagaat tatgcagtgc tgccataacc atgagtgata acactgcggc    780
caacttactt ctgacaacga tcggaggacc gaaggagcta accgcttttt tgcacaacat    840
gggggatcat gtaactcgcc ttgatcgttg gaaccggag ctgaatgaag ccataccaaa    900
cgacgagcgt gacaccacga tgcctgtagc aatggcaaca cgttgcgca aactattaac    960
tggcgaacta cttactctag cttcccggca acaattaata gactggatgg aggcggataa   1020
agttgcagga ccacttctgc gctcggccct ccggctggc tggtttattg ctgataaatc   1080
tggagccggt gagcgtgggt ctcgcggtat cattgcagca ctggggccag atggtaagcc   1140
ctcccgtatc gtagttatct acacgacggg gagtcaggca actatggatg aacgaaatag   1200
acagatcgct gagataggtg cctcactgat taagcattgg taactgtcag accaagttta   1260
ctcatatata ctttagattg atttaaaact tcattttaa tttaaaagga tctaggtgaa   1320
gatccttttt gataatctca tgaccaaaat cccttaacgt gagttttcgt tccactgagc   1380
gtcagacccc gtagaaaaga tcaaaggatc ttcttgagat cctttttttc tgcgcgtaat   1440
ctgctgcttg caaacaaaaa aaccaccgct accagcggtg gtttgtttgc cggatcaaga   1500
gctaccaact ctttttccga aggtaactgg cttcagcaga gcgcagatac caaatactgt   1560
tcttctagtg tagccgtagt taggccacca cttcaagaac tctgtagcac cgcctacata   1620
cctcgctctg ctaatcctgt taccagtggc tgctgccagt ggcgataagt cgtgtcttac   1680
cgggttggac tcaagacgat agttaccgga taaggcgcag cggtcgggct gaacggggggg   1740
ttcgtgcaca cagcccagct tggagcgaac gacctacacc gaactgagat acctacagcg   1800
tgagctatga gaaagcgcca cgcttcccga agggagaaag gcggacaggt atccggtaag   1860
cggcagggtc ggaacaggag agcgcacgag ggagcttcca gggggaaacg cctggtatct   1920
ttatagtcct gtcgggtttc gccacctctg acttgagcgt cgatttttgt gatgctcgtc   1980
aggggggcgg agcctatgga aaaacgccag caacgcggcc ttttacggt tcctggcctt   2040
ttgctggcct tttgctcaca tgttctttcc tgcgttatcc cctgattctg tggataaccg   2100
tattaccgcc tttgagtgag ctgataccgc tcgccgcagc cgaacgaccg agcgcagcga   2160
gtcagtgagc gaggaagcgg aagagcgccc aatacgcaaa ccgcctctcc ccgcgcgttg   2220
gccgattcat taatgcagct ggcacgacag gtttcccgac tggaaagcgg gcagtgagcg   2280
caacgcaatt aatgtgagtt agctcactca ttaggcaccc caggctttac actttatgct   2340
tccggctcgt atgttgtgtg gaattgtgag cggataacaa tttcacacag gaaacagcta   2400
tgaccatgat tacgccaagc tcgcggccgc agtactctgc agattttatg caaaattaaa   2460
gtcttgtgac aacagctttc tccttaagtg caaatatcgc ccattctttc ctcttttcgt   2520
atataaatgc tgtaatagta ggatgtcgta cccgtaaagg tacgacattg aatattaata   2580
tactcctaag tttactttcc caatatttat attaggacgt cccccttcggg taataaaatt   2640
ttagtggcag tggtaccgcc actccctatt ttaatactgc gaaggaggca gttggcaggc   2700
aactcgtcgt tcgcagtata taaatatcca ctaatattta tattcccgta aggggacgtc   2760
ccgaagggga agggaaaga agcagtcgcc tccttgcgaa aaggtttact tgcccgacca   2820
gtgaaaagca tgctgtaaga tataaatcta ccctgaaagg gatgcatttc accataatac   2880
tatacaaatg gtgttaccct ttgaggatca taacggtgct actggaatat atggtctctt   2940
```

```
catggataga cgatagccat ttatttaccc attaagggga cattagtggc ctgtcactgc    3000
tccttacgag acgccagtgg acgttcgtcc tagaaaattt atgcgctgcc tagaagcccc    3060
aaaagggaag tttactgact cgttagagcg tgcgctaaca ggtttaaata cttcaatatg    3120
tatattagga cgccggtggc agtggtaccg ccactgccac cgtcggagga cgtcccttac    3180
ggtatattat atactaggat tttaatactc cgaaggaggc agtggcgtta ccactgccac    3240
taatatttat attcccgtaa gggacgtcct ccttcggagt atgtaaacat tctaagttta    3300
cttgcccaat atttatatta ggcagttggc aggcaactgc tagctctcct ccttcggagt    3360
atgtaaacat cgcagtatat aaatatccac taatatttat attcccgtaa ggggacgtcc    3420
cgaaggggaa ggggaaggac gtcagtggca gttgcctgcc aactgcctag gcaagtaaac    3480
ttaggagtat ataaatatag gcagtcgcgg taccactgcc actgacgtcc tgccaactgc    3540
ctaggcaagt aaacttaagt ggcactaaaa tgcatttgcc cgaagggaa ggaggacgcc    3600 agtggcagtg gtaccgccac tgcctccttc ggagtattaa aatcctagta tgtaaatctg    3660
ctagcgcagg aaataaattt tattctattt atatactccg ttaggaggta agtaaacccc    3720
ttccccttcg ggacgtcagt gcagttgcct gccaactgcc taatataaat attagaccac    3780
taaagtttgg caactgccaa ctgttgtcct tcggaggaaa aaaaatggtt aactcgcaag    3840
cagttaacat aactaaagtt tgttacttta ccgaagacgt ttacccttc tcggttaagg    3900 agacggagac agttgcactg tgactgccta gtatagcaat tttgtttttg tttatatgct    3960
cgacaaaatg actttcataa aaatataaag tagttagcta gttattttat atcactataa    4020
ctagggttct cagaggcacc gaagtcactt gtaaaaatag tactttttaa cttgtttaat    4080
cttcgtgttc ttcaaaagga tcacgtaatt tttttgaagg tggaccaaaa ctaacataaa    4140
ctgaatagcc agttacactt aacagaagaa accataaaaa aaaggtaaag aaaaaagctg    4200
gactttccat agctcattta ataataaaat tattctcttt tcaacatatc tcttagatag    4260
ttcaaaagac ttgacgactg tgtcccacat ttttaaacaa aattaatcta ctcaaaattt    4320
tgccctgaga aagaataact tacttcgttt ttgcagtagc cattcatgtc actttgaaac    4380
tgtccttaca aagttaaaca ttaattaaaa attatttaat tttatataa caaatattat    4440 attaaataaa aaatgaacaa agaacttcta agatcgtctt tagtgagtaa ttaaagagtt    4500
ttacttacca gacaaggcag ttttttcatt cttttaaagc aggcagttct gaagggaaa    4560 agggactgcc tactgcggtc ctaggtaaat acatttttat gcaatttatt tcttgtgcta    4620
gtaggtttct atactcacaa gaagcaaccc cttgacgaga aacgttatc ctcagagtat    4680 ttataatcct gagagggaat gcactgaaga atatttttcct tatttttttac agaaagtaaa    4740 taaaatagcg ctaataacgc ttaattcatt taatcaatta tggcaacagg aacttctaaa    4800
gctaaaccat caaaagtaaa ttcagacttc caagaacctg gtttagttac accattaggt    4860
actttattac gtccacttaa ctcagaagca ggtaaagtat taccaggctg gggtacaact    4920
gttttaatgg ctgtatttat ccttttattt gcagcattct tattaatcat tttagaaatt    4980
tacaacagtt ctttaatttt agatgacgtt tctatgagtt gggaaacttt agctaaagtt    5040
tcttaatttt atttaacaca acataaaat ataaaactgt ttgttaaggc tagctgctaa    5100
gtcttctttt cgctaaggta aactaagcaa ctcaaccata tttatattcg gcagtggcac    5160
cgccaactgc cactggcctt ccgttaagat aaacgcgtgg atctcacgtg actagtgata    5220
tctacgtaat cgatgaattc gatcccattt ttataactgg atctcaaaat acctataaac    5280
ccattgttct tctctttttag ctctaagaac aatcaattta taatatatt tattattatg    5340
```

```
ctataatata aatactatat aaatacatttt accttttat aaatacattt accttttttt    5400
taatttgcat gatttaatg cttatgctat ctttttatt tagtccataa aacctttaaa      5460 ggacctttc ttatgggata tttatatttt cctaacaaag caatcggcgt cataaacttt     5520
agttgcttac gacgcctgtg gacgtccccc ccttcccctt acgggcaagt aaacttaggg    5580 atttaatgc aataaataaa tttgtcctct tcgggcaaat gaattttagt atttaaatat     5640
gacaagggtg aaccattact tttgttaaca agtgatctta ccactcacta ttttgttga    5700 attttaaact tatttaaaat tctcgagaaa gatttaaaa ataaactttt ttaatctttt    5760
atttattttt tctttttcg tatggaattg cccaatatta ttcaacaatt tatcggaaac     5820
agcgttttag agccaaataa aattggtcag tcgccatcgg atgtttattc ttttaatcga    5880
aataatgaaa cttttttct taagcgatct agcactttat atacagagac cacatacagt     5940
gtctctcgtg aagcgaaaat gttgagttgg ctctctgaga aattaaaggt gcctgaactc    6000
atcatgactt tcaggatga gcagtttgaa tttatgatca ctaaagcgat caatgcaaaa    6060 ccaattcag cgctttttt aacagaccaa gaattgcttg ctatctataa ggaggcactc     6120
aatctgttaa attcaattgc tattattgat tgtccattta tttcaaacat tgatcatcgg    6180
ttaaaagagt caaatttt tattgataac caactccttg acgatataga tcaagatgat    6240
tttgacactg aattatgggg agaccataaa acttacctaa gtctatggaa tgagttaacc    6300
gagactcgtg ttgaagaaag attggttttt tctcatggcg atatcacgga tagtaatatt     6360
tttatagata aattcaatga aatttatttt ttagaccttg gtcgtgctgg gttagcagat    6420
gaatttgtag atatatcctt tgttgaacgt tgcctaagag aggatgcatc ggaggaaact    6480
gcgaaaatat ttttaaagca tttaaaaaat gatagacctg acaaaaggaa ttattttta     6540 aaacttgatg aattgaattg attccaagca ttatctaaaa tactctgcag gcacgctagc    6600
ttgtactcaa gctcgtaacg aaggtcgtga ccttgctcgt gaaggtggcg acgtaattcg    6660
ttcagcttgt aaatggtctc cagaacttgc tgctgcatgt gaagtttgga aagaaattaa    6720
attcgaattt gatactattg acaaacttta atttttattt ttcatgatgt ttatgtgaat    6780
agcataaaca tcgttttat ttttatggtg tttaggttaa atacctaaac atcatttac     6840 atttttaaaa ttaagttcta aagttatctt ttgttaat ttgcctgtct ttataaatta     6900
cgatgtgcca gaaaaataaa atcttagctt tttattatag aatttatctt tatgtattat    6960
attttataag ttataataaa agaaatagta acatactaaa gcggatgtag cgcgtttatc    7020
ttaacggaag gaattcggcg cctacgtacc cgggtcgcga ggatccacgc gttaatagct    7080
cacttttctt taaattaat ttttaattta aaggtgtaag caaattgcct gacgagagat     7140
ccacttaaag gatgacagtg gcgggctact gcctacttcc ctccgggata aaattatt     7200 gaaaaacgtt agttacttcc taacggagca ttgacatccc catatttata ttaggacgtc    7260
ccccttcggg aaataaattt tagtggacgt cccccttcgg gcaaataaatt ttagtggaca    7320 ataaataaat ttgttgcctg ccaactgcct aggcaagtaa acttgggagt attaaaatag    7380
gacgtcagtg gcagttgcct gccaactgcc tatatttata tactgcgaag caggcagtgg    7440
cggtaccact gccactggcg tcctaatata aatattgggc aactaaagtt tatagcagta    7500
ttaacatcct atatttatat actccgaagg aacttgttag ccgataggcg aggcaacaaa    7560
tttatttatt gtcccgtaaa aggatgcctc cagcatcgaa ggggaagggg acgtcctagg    7620
ccataaaact aaagggaaat ccatagtaac tgatgttata aatttataga ctccaaaaaa    7680
cagctgcgtt ataaataact tctgttaaat atggccaagg ggacagggc actttcaact    7740
```

| | | | | |
|---|---|---|---|---|
| aagtgtacat | taaaaattga | caattcaatt | tttttaatt | ataatatata | tttagtaaaa | 7800 |
| tataacaaaa | agcccccatc | gtctaggtag | aattccagct | ggcggccgcc | ctatg | 7855 |

<210> SEQ ID NO 5
<211> LENGTH: 8458
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | | | | | |
|---|---|---|---|---|---|
| tcgtgtagat | aactacgata | cgggagggct | taccatctgg | ccccagtgct | gcaatgatac | 60 |
| cgcgagaccc | acgctcaccg | gctccagatt | tatcagcaat | aaaccagcca | gccggaaggg | 120 |
| ccgagcgcag | aagtggtcct | gcaactttat | ccgcctccat | ccagtctatt | aattgttgcc | 180 |
| gggaagctag | agtaagtagt | tcgccagtta | atagtttgcg | caacgttgtt | gccattgcta | 240 |
| caggcatcgt | ggtgtcacgc | tcgtcgtttg | gtatggcttc | attcagctcc | ggttcccaac | 300 |
| gatcaaggcg | agttacatga | tcccccatgt | tgtgcaaaaa | agcggttagc | tccttcggtc | 360 |
| ctccgatcgt | tgtcagaagt | aagttggccg | cagtgttatc | actcatggtt | atggcagcac | 420 |
| tgcataattc | tcttactgtc | atgccatccg | taagatgctt | ttctgtgact | ggtgagtact | 480 |
| caaccaagtc | attctgagaa | tagtgtatgc | ggcgaccgag | ttgctcttgc | ccggcgtcaa | 540 |
| tacgggataa | taccgcgcca | catagcagaa | ctttaaaagt | gctcatcatt | ggaaaacgtt | 600 |
| cttcggggcg | aaaactctca | aggatcttac | cgctgttgag | atccagttcg | atgtaaccca | 660 |
| ctcgtgcacc | caactgatct | tcagcatctt | ttactttcac | cagcgtttct | gggtgagcaa | 720 |
| aaacaggaag | gcaaaatgcc | gcaaaaaagg | gaataagggc | gacacggaaa | tgttgaatac | 780 |
| tcatactctt | cctttttcaa | tattattgaa | gcatttatca | gggttattgt | ctcatgagcg | 840 |
| gatacatatt | tgaatgtatt | tagaaaaata | aacaaatagg | ggttccgcgc | acatttcccc | 900 |
| gaaaagtgcc | acctgacgtc | taagaaacca | ttattatcat | gacattaacc | tataaaaata | 960 |
| ggcgtatcac | gaggcccttt | cgtctcgcgc | gtttcggtga | tgacggtgaa | aacctctgac | 1020 |
| acatgcagct | cccggagacg | gtcacagctt | gtctgtaagc | ggatgccggg | agcagacaag | 1080 |
| cccgtcaggg | cgcgtcagcg | ggtgttggcg | ggtgtcgggg | ctggcttaac | tatgcggcat | 1140 |
| cagagcagat | tgtactgaga | gtgcaccata | gggcggccgc | ggcgcgccgt | tccggatctg | 1200 |
| catcctgcga | tgcagatccg | gaacataatg | gtgcagggcg | ctgacttccg | cgtttccaga | 1260 |
| ctttacgaaa | cacggaaacc | gaagaccatt | catgttgttg | ctcaggtcgc | agacgttttg | 1320 |
| cagcagcagt | cgcttcacgt | tcgctcgcgt | atcggtgatt | cattctgcta | accagtaagg | 1380 |
| caaccccgcc | agcctagccg | ggtcctcaac | gacaggagca | cgatcatgcg | cacccgtggc | 1440 |
| caggacccaa | cgctgcccga | gatgcgccgc | gtgcggctgc | tggagatggc | ggacgcgatg | 1500 |
| gatatgttct | gccaagggtt | ggtttgcgca | ttcacagttc | tccgcaagaa | ttgattggct | 1560 |
| ccaattcttg | gagtggtgaa | tccgttagcg | aggtgccgcc | ggcttccatt | caggtcgagg | 1620 |
| tggcccggct | ccatgcaccg | cgacgcaacg | cggggaggca | gacaaggtat | agggcggcgc | 1680 |
| ctacaatcca | tgccaacccg | ttccatgtgc | tcgccgaggc | ggcataaatc | gccgtgacga | 1740 |
| tcagcggtcc | aatgatcgaa | gttaggctgg | taagagccgc | gagcgatcct | tgaagctgtc | 1800 |
| cctgatggtc | gtcatctacc | tgcctggaca | gcatggcctg | caacgcgggc | atcccgatgc | 1860 |
| cgccggaagc | gagaagaatc | ataatgggga | aggccatcca | gcctcgcgtc | gcgaacgcca | 1920 |

```
gcaagacgta gcccagcgcg tcggccgcca tgccggcgat aatggcctgc ttctcgccga      1980
aacgtttggt ggcgggacca gtgacgaagg cttgagcgag ggcgtgcaag attccgaata      2040
ccgcaagcga caggccgatc atcgtcgcgc tccagcgaaa gcggtcctcg ccgaaaatga      2100
cccagagcgc tgccggcacc tgtcctacga gttgcatgat aaagaagaca gtcataagtg      2160
cggcgacgat agtcatgccc cgcgcccacc ggaaggagct gactgggttg aaggctctca      2220
agggcatcgg tcgagcttga cattgtagga cgtttaaaca ttaccctgtt atccctagga      2280
tcctacgtaa tcgatgaatt cgatcccatt tttataactg gatctcaaaa tacctataaa      2340
cccattgttc ttctcttta gctctaagaa caatcaattt ataaatatat ttattattat       2400
gctataatat aaatactata taaatacatt taccttttta taaatacatt tacctttttt      2460
ttaatttgca tgattttaat gcttatgcta tcttttttat ttagtccata aaacctttaa      2520
aggacctttt cttatgggat atttatattt tcctaacaaa gcaatcggcg tcataaactt      2580
tagttgctta cgacgcctgt ggacgtcccc cccttccct tacgggcaag taaacttagg       2640
gattttaatg caataaataa atttgtcctc ttcgggcaaa tgaattttag tatttaaata      2700
tgacaagggt gaaccattac ttttgttaac aagtgatctt accactcact attttgttg       2760 aattttaaac ttatttaaaa ttctcgagaa agattttaaa aataaacttt tttaatctt       2820 tatttatttt ttcttttttc gtatggaatt gcccaatatt attcaacaat ttatcggaaa      2880
cagcgtttta gagccaaata aaattggtca gtcgccatcg gatgtttatt cttttaatcg      2940
aaataatgaa acttttttc ttaagcgatc tagcacttta tatacagaga ccacatacag       3000
tgtctctcgt gaagcgaaaa tgttgagttg gctctctgag aaattaaagg tgcctgaact      3060
catcatgact tttcaggatg agcagtttga atttatgatc actaaagcga tcaatgcaaa      3120
accaatttca gcgcttttt taacagacca agaattgctt gctatctata aggaggcact       3180
caatctgtta aattcaattg ctattattga ttgtccattt atttcaaaca ttgatcatcg      3240
gttaaaagag tcaaaatttt ttattgataa ccaactcctt gacgatatag atcaagatga      3300
ttttgacact gaattatggg gagaccataa aacttaccta agtctatgga atgagttaac      3360
cgagactcgt gttgaagaaa gattggtttt ttctcatggc gatatcacgg atagtaatat      3420
ttttatagat aaaattcaatg aaatttattt tttagacctt ggtcgtgctg ggttagcaga     3480
tgaatttgta gatatatcct tgttgaacg ttgcctaaga gaggatgcat cggaggaaac       3540
tgcgaaaata ttttaaagc atttaaaaaa tgatagacct gacaaaagga attatttttt      3600
aaaacttgat gaattgaatt gattccaagc attatctaaa atactctgca ggcacgctag      3660
cttgtactca agctcgtaac gaaggtcgtg accttgctcg tgaaggtggc gacgtaattc      3720
gttcagcttg taaatggtct ccagaacttg ctgctgcatg tgaagtttgg aaagaaatta      3780
aattcgaatt tgatactatt gacaaacttt aatttttatt tttcatgatg tttatgtgaa      3840
tagcataaac atcgttttta ttttatggt gtttaggtta aatacctaaa catcatttta      3900
catttttaaa attaagttct aaagttatct tttgtttaaa tttgcctgtc tttataaatt     3960
acgatgtgcc agaaaaataa aatcttagct ttttattata gaatttatct ttatgtatta     4020 tatttataa gttataataa aagaaatagt aacatactaa agcggatgta gcgcgtttat       4080
cttaacggaa ggaattcggc gcctacgtat acatactccg aaggaggaca aatttattta     4140
ttgtggtaca ataaataagt ggtacaataa ataaattgta tgtaaacccc ttccccttcg     4200
ggacgtcccc ttcgggaat ataaatatta gtggcagttg cctgccaaca aatttattta      4260
ttgtattaac ataggcagtg gcggtaccac tgccactggc gtcctaatat aaatattggg     4320
```

```
caactaaagt ttatcgcagt attaacatag gcagtggcgg taccactgcc actggcgtcc    4380
tccttcggag tatgtaaacc tgctaccgca gcaaataaat tttattctat tttaatacta    4440
caatatttag attcccgtta ggggataggc caggcaattg tcactggcgt catagtatat    4500
caatattgta acagattgac accctttaag taaacatttt ttttaggatt catatgaaat    4560
taaatggata tttggtacat ttaattccac aaaaatgtcc aatacttaaa atacaaaatt    4620
aaaagtatta gttgtaaact tgactaacat tttaaatttt aaattttttc ctaattatat    4680
atttttacttg caaaatttat aaaaatttta tgcatttta tatcataata ataaaacctt    4740
tattcatggt ttataatata ataattgtga tgactatgca caaagcagtt ctagtcccat    4800
atatataact atatataacc cgtttaaaga tttatttaaa aatatgtgtg taaaaaatgc    4860
ttattttaa ttttatttta taagttat aatattaaat acacaatgat taaaattaaa    4920
taataataaa tttaacgtaa cgatgagttg ttttttttatt ttggagatac acgcaatgac    4980
aattgcgatc ggtacatatc aagagaaacg cacatggttc gatgacgctg atgactggct    5040
tcgtcaagac cgtttcgtat tcgtaggttg gtcaggttta ttactattcc cttgtgctta    5100
ctttgcaact ccggtccggc ggccgcctcg agacgacttg tccgcttcat cagacacggc    5160
tttcctaacc atcaatggtg gattttcagg aaagacgttt aaagaagtgg cataaagttt    5220
atttgttgaa gaattggttt tgtttccatt caaagaattg ttagggataa aactttgcat    5280
ttttttataa tttgttataa gttttttcaaa cttatatgtt tttaaaaatg catttaattg    5340
cttattaatg cgttcatttt gtaatgtttc aataggtctt gcttgcgcta atcgcagtat    5400
tcccgatact ttgtctgctt gttttttcggg tattgagaat aagtaagtat aatgatttaa    5460
aaaagtcatg ttttgattaa atctttttta tatggttaaa aacattatgg tatatctaaa    5520
taaatttatt ttttactaaa tctccaattt gcaatttaga gatataatta aaactataaa    5580
gttatttaag ttaatttgta atcaaatcca acacaaaaat gttttttatat agttaacatg    5640
ttaaatttaa catatgttaa acaactaaaa ttctgtaaca gagaacaata aaataaatgc    5700
tagattttgt gtaatgccga agtatattta tatacttccc tttcaaaaaa ataaatactc    5760
ttgccactaa aattcatttg cctaggacgt ccccttcccc ttacgggatg tttatatact    5820
aggacgtccc cttcccctta cgggatattt atatactccg aaggacgtcc ccttcgggca    5880
aataaattt agtggcagtt gcctgccaac tgcctaggca agtaaactta gggattttaa    5940
tgcaataaat aaatttgtcc ccttacggga cgtcagtggc agttgcctgc caactgccta    6000
atataaatat tagtggatat ttatatactc cgaaggaggc agttacctgc caactgccga    6060
ggcaaataaa ttttagtggc agtggtaccg ccactgcctg ctccctcctt cccttcggg    6120
caagtaaact tagcatgttg tcgacattac cctgttatcc ctaggccggc ctaagaaacc    6180
attattatca tgacattaac ctataaaaat aggcgtatca cgaggccctt tcgtcttcaa    6240
gaaattcggt cgaaaaaaga aaaggagagg gccaagaggg agggcattgg tgactattga    6300
gcacgtgagt atacgtgatt aagcacacaa aggcagcttg gagtatgtct gttattaatt    6360
tcacaggtag ttctggtcca ttggtgaaag tttgcggctt gcagagcaca gaggccgcag    6420
aatgtgctct agattccgat gctgacttgc tgggtattat atgtgtgccc aatagaaaga    6480
gaacaattga cccggttatt gcaaggaaaa tttcaagtct tgtaaaagca tataaaaata    6540
gttcaggcac tccgaaatac ttggttggcg tgtttcgtaa tcaacctaag gaggatgttt    6600
tggctctggt caatgattac ggcattgata tcgtccaact gcatggagat gagtcgtggc    6660
aagaatacca agagttcctc ggtttgccag ttattaaaag actcgtattt ccaaaagact    6720
```

-continued

```
gcaacatact actcagtgca gcttcacaga aacctcattc gtttattccc ttgtttgatt    6780
cagaagcagg tgggacaggt gaacttttgg attggaactc gatttctgac tgggttggaa    6840
ggcaagagag ccccgaaagc ttacatttta tgttagctgg tggactgacg ccagaaaatg    6900
ttggtgatgc gcttagatta aatggcgtta ttggtgttga tgtaagcgga ggtgtggaga    6960
caaatggtgt aaaagactct aacaaaatag caaatttcgt caaaaatgct aagaaatagg    7020
ttattactga gtagtattta tttaagtatt gtttgtgcac ttgcctgcag gccttttgaa    7080
aagcaagcat aaaagatcta aacataaaat ctgtaaaata acaagatgta aagataatgc    7140
taaatcattt ggctttttga ttgattgtac aggaaaatat acatcgttaa ttaagcggcc    7200
gcgagcttgg cgtaatcatg gtcatagctg tttcctgtgt gaaattgtta tccgctcaca    7260
attccacaca acatacgagc cggaagcata aagtgtaaag cctggggtgc ctaatgagtg    7320
agctaactca cattaattgc gttgcgctca ctgcccgctt tccagtcggg aaacctgtcg    7380
tgccagctgc attaatgaat cggccaacgc gcggggagag gcggtttgcg tattgggcgc    7440
tcttccgctt cctcgctcac tgactcgctg cgctcggtcg ttcggctgcg gcgagcggta    7500
tcagctcact caaaggcggt aatacggtta tccacagaat caggggataa cgcaggaaag    7560
aacatgtgag caaaaggcca gcaaaaggcc aggaaccgta aaaaggccgc gttgctggcg    7620 ttttccata ggctccgccc ccctgacgag catcacaaaa atcgacgctc aagtcagagg    7680
tggcgaaacc cgacaggact ataaagatac caggcgtttc cccctggaag ctccctcgtg    7740
cgctctcctg ttccgaccct gccgcttacc ggatacctgt ccgcctttct cccttcggga    7800
agcgtggcgc tttctcatag ctcacgctgt aggtatctca gttcggtgta ggtcgttcgc    7860
tccaagctgg gctgtgtgca cgaaccccc gttcagcccg accgctgcgc cttatccggt    7920
aactatcgtc ttgagtccaa cccggtaaga cacgacttat cgccactggc agcagccact    7980
ggtaacagga ttagcagagc gaggtatgta ggcggtgcta cagagttctt gaagtggtgg    8040
cctaactacg gctacactag aagaacagta tttggtatct gcgctctgct gaagccagtt    8100
accttcggaa aaagagttgg tagctcttga tccggcaaac aaaccaccgc tggtagcggt    8160
ggtttttttg tttgcaagca gcagattacg cgcagaaaaa aaggatctca agaagatcct    8220
ttgatctttt ctacggggtc tgacgctcag tggaacgaaa actcacgtta agggattttg    8280
gtcatgagat tatcaaaaag gatcttcacc tagatccttt taaattaaaa atgaagtttt    8340
aaatcaatct aaagtatata tgagtaaact tggtctgaca gttaccaatg cttaatcagt    8400
gaggcaccta tctcagcgat ctgtctattt cgttcatcca tagttgcctg actccccg      8458
```

<210> SEQ ID NO 6
<211> LENGTH: 22908
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
tgaatttatc agatctaact gaggagtaag aaacccccat gtcaaagaaa acagaccaa      60 caattgggcg aacccttaat ccttcaatat taagcggatt tgatagttct tcagcctctg    120
gcgatcgagt cgagcaggta ttcaagttat caactggtcg ccaggccaca tttattgaag    180
aggtaatacc tccgaaccag gtagaaagcg atacctttgt tgatcagcat aacaacgggc    240
gtgaccagga atctcttacg ccaaaatcat taaaaagtat ccgaagcact attaagcatc    300
agcaatttta ccctgcaata ggtgttagac gggctacagg gaaaattgaa attttggatg    360
```

```
gttcccggcg tcgagcttct gccatcttag agaacgtagg gttgcgggtt ttagtcacgg    420
accaggagat cagcgttcag gaagcgcaaa atttagcgaa agacgttcag acagcattgc    480
agcacagcat tcgagaaata ggtctgcgtt tgatgcgaat gaaaaatgat gggatgagtc    540
agaaggatat tgcagccaaa gaagggctgt ctcaggcgaa ggtcacgcgt gctctccagg    600
cagcgagtgc tccggaagaa ttagtcgccc ttttccctgt gcagtcggaa ttaaccttt     660 cggactacaa aacgctttgt gctgttggcg acgaaatggg gaacaagaat ttagagtttg    720
atcagcttat tcaaaacata tccccggaaa taaacgacat cttatccatt gaagaaatgg    780
ccgaagatga agttaaaaat aaaatcctgc gcttgataac aaaggaagcc tcactactca    840
cggataaagg ttctaaagat aagtccgtag ttactgaatt atggaaattt gaggacaagg    900
atcgctttgc aaggaagcgc gtgaaaggcc gtgcattttc ttatgagttt aatcgactct    960
caaaagagtt acaggaagaa ctcgacagga tgattgggca tatccttaga aagagcctcg    1020
ataaaaagcc gaagccttaa actttcgcca ttcaaatttc actattaact gactgttttt    1080
aaagtaaatt actctaaaat ttcaaggtga aatcgccacg atttcacctt ggattttacc    1140
ttcctcccct cctcccgaaa aaaataaaaa aattgcttgt cacgagaaag tcaacaagtg    1200
actttcaata aaatctcttc cgaaaaggga ttcacacaag tgccttgtgt ttaaggaaga    1260
gtaaattgag taacttacgc gaataccaga atcgtattgc agatatcgca aaacgctcta    1320
aagctgtgct tggctgggca agcactgcgc agttcggtac tgataaccaa ttcattaaag    1380
atgatgccgc gcgtgccgca tctatccttg aagctcacg  taaagacccg gttttttgcgg   1440 gtatctctga taatgccacc gctcaaatcg ctacagcgtg ggcaagtgca ctggctgact    1500
acgccgcagc acataaatct atgccgcgtc cggaaattct ggcctcctgc caccagacgc    1560
tggaaaactg cctgatagag tccacccgca atagcatgga tgccactaat aaagcgatgc    1620
tggaatctgt cgcagcagag atgatgagcg tttctgacgg tgttatgcgt ctgccttta    1680 tcctcgcgat gatcctgcct gttcagttgg gggcagctac cgctgatgcg tgtaccttca    1740
ttccggttac gcgtgaccag tccgacatct atgaagtctt taacgtgca ggttcatctt     1800 ttggttctta tgctgctggt gatgttctgg acatgcaatc cgtcggtgtg tacagccagt    1860
tacgtcgccg ctatgtgctg gtggcaagct ccgatggcac cagcaaaacc gcaaccttca    1920
agatggaaga cttcgaaggc cagaatgtac caatccgaaa aggtcgcact aacatctacg    1980
ttaaccgtat taagtctgtt gttgataacg gttccggcag cctacttcac tcgtttacta    2040
atgctgctgg tgagcaaatc actgttacct gctctctgaa ctacaacatt ggtcagattg    2100
ccctgtcgtt ctccaaagcg ccggataaag gcactgagat cgcaattgag acggaaatca    2160
atattgaagc cgctcctgag ctgatcccgc tgatcaacca cgaaatgaag aaatacaccc    2220
tgttcccaag tcagttcgtt atcgcggctg agcacacggt acaggcggcg tatgaagcac    2280
agcgtgaatt tggtctggac ctgggttccc tacagttccg caccctgaag gaatacctgt    2340
ctcatgaaca ggatatgctg cgtcttcgca tcatgatctg gcgcactctt gcgaccgaca    2400
cctttgacat cgctctgccg gttaaccagt cctttgatgt atgggcaacc atcattcgtg    2460
gcaaattcca gactgtatat cgcgacatta ttgagcgcgt taaatcttct ggtgcgatgg    2520
ggatgtttgc tggtgctgat gcagcatctt tcttcaaaca gttgccgaag gatttcttcc    2580
agccagccga agactatatc cagactccgt atgttcacta catcggtacc ccatttagga    2640
ccacccacag cacctaacaa aacggcatca gccttcttgg aggcttccag cgcctcatct    2700
ggaagtggaa cacctgtagc atcgacctgc aggggggggg gggcgctgag gtctgcctcg    2760
```

```
tgaagaaggt gttgctgact cataccaggc ctgaatcgcc ccatcatcca gccagaaagt    2820
gagggagcca cggttgatga gagctttgtt gtaggtggac cagttggtga ttttgaactt    2880
ttgctttgcc acggaacggt ctgcgttgtc gggaagatgc gtgatctgat ccttcaactc    2940
agcaaaagtt cgatttattc aacaaagccg ccgtcccgtc aagtcagcgt aatgctctgc    3000
cagtgttaca accaattaac caattctgat tagaaaaact catcgagcat caaatgaaac    3060
tgcaatttat tcatatcagg attatcaata ccatattttt gaaaaagccg tttctgtaat    3120
gaaggagaaa actcaccgag gcagttccat aggatggcaa gatcctggta tcggtctgcg    3180
attccgactc gtccaacatc aatacaacct attaatttcc cctcgtcaaa aataaggtta    3240
tcaagtgaga atcaccatg agtgacgact gaatccggtg agaatggcaa agcttatgc     3300 atttctttcc agacttgttc aacaggccag ccattacgct cgtcatcaaa atcactcgca    3360
tcaaccaaac cgttattcat tcgtgattgc gcctgagcga gacgaaatac gcgatcgctg    3420
ttaaaaggac aattacaaac aggaatcgaa tgcaaccggc gcaggaacac tgccagcgca    3480
tcaacaatat tttcacctga atcaggatat tcttctaata cctggaatgc tgttttcccg    3540
gggatcgcag tggtgagtaa ccatgcatca tcaggagtac ggataaaatg cttgatggtc    3600
ggaagaggca taaattccgt cagccagttt agtctgacca tctcatctgt aacatcattg    3660
gcaacgctac ctttgccatg tttcagaaac aactctggcg catcgggctt cccatacaat    3720
cgatagattg tcgcacctga ttgcccgaca ttatcgcgag cccatttata cccatataaa    3780
tcagcatcca tgttggaatt taatcgcggc ctcgagcaag acgtttcccg ttgaatatgg    3840
ctcataacac cccttgtatt actgtttatg taagcagaca gttttattgt tcatgatgat    3900
atatttttat cttgtgcaat gtaacatcag agattttgag acacaacgtg gctttccccc    3960
ccccccctgc aggtcgatag cagcaccacc aattaaatga ttttcgaaat cgaacttgac    4020
attggaacga acatcagaaa tagctttaag aaccttaatg gcttcggctg tgatttcttg    4080
accaacgtgg tcacctggca aaacgacgat cttcttaggg gcagacatta gaatggtata    4140
tccttgaaat atatatatat attgctgaaa tgtaaaaggt aagaaaagtt agaaagtaag    4200
acgattgcta accacctatt ggaaaaaaca ataggtcctt aaataatatt gtcaacttca    4260
agtattgtga tgcaagcatt tagtcatgaa cgcttctcta ttctatatga aaagccggtt    4320
ccggcgctct cacctttcct ttttctccca attttttcagt tgaaaaaggt atatgcgtca    4380
ggcgacctct gaaattaaca aaaaattttcc agtcatcgaa tttgattctg tgcgatagcg    4440
cccctgtgtg ttctcgttat gttgaggaaa aaaataatgg ttgctaagag attcgaactc    4500
ttgcatctta cgatacctga gtattcccac agttaactgc ggtcaagata tttcttgaat    4560
caggcgcctt agaccgctcg gccaaacaac caattacttg ttgagaaata gagtataatt    4620
atcctataaa tataacgttt ttgaacacac atgaacaagg aagtacagga caattgattt    4680
tgaagagaat gtggattttg atgtaattgt tgggattcca tttttaataa ggcaataata    4740
ttaggtatgt agatatacta gaagttctcc tcgacgctct cccttatgcg actcctgcat    4800
taggaagcag cccagtagta ggttgaggcc gttgagcacc gccgccgcaa ggaatggtgc    4860
atgcaaggag atggcgccca acagtccccc ggccacgggg cctgccacca tacccacgcc    4920
gaaacaagcg ctcatgagcc cgaagtgcg agcccgatct tccccatcgg tgatgtcggc     4980
gatataggcg ccagcaaccg cacctgtggc gccggtgatg ccggccacga tgcgtccggc    5040
gtagaggatc tacaactcca cttattgtta ggtagaattg tccgttagtt gtttattaat    5100
tgcaataatg gggcgtccag ttttggcaac agtgtcctct taccaggaca cctatgagtt    5160
```

```
tgcctcatgg caaactagag gtgttgaaag tatgcatggt tataattaga gcaattcatt   5220
accctctgaa tcctgccggt atacccatt gttcgttatc tttatttttg gctaaaaccg    5280
cattaagagc ttcgtttacc gtcatgcaat gcggtaggtt atcgaagttt gatatcccgc   5340
caatatcagg cgaacgcttg ttcttcaggt aagcatattt ccgcgcagcc gcctctactt   5400
tctgcttgaa ctcatgtttt tgagtgcgtt ttttggataa ccgcagattg tcagcctttg   5460
cttttgcctt agcgatccat gaagtcaatt ttttgaggct ggttgttccg gcaccgccgg   5520
aaactgatct ttttgttttt ttaacttgtg acttcttatt ctttattgcc acgtcatcct   5580
gacaggggga gggggtatca ttttgacatg ggggtgtgga taaaaaatta aataaagcca   5640
atgtcttagc gagaacagct ttaaccttgg ttgccgctga agagatcttt aatttgcttt   5700
ctatcagcgc attttggct tgttgtgcga aggccaaaaa ggatggtgta aaccggtaca    5760
ggttagcgcg acgttcacgg tgatcgccga taacaatctc tacagacaga attcctttgt   5820
ttacagcttc acggaatgca cgaacgacgg ttgattggct ataaccagtt tctgccgcga   5880
tcaggcggtg aggcttgtga atgaagtatt cactggttgt tgccgcgaga tttgcacatt   5940
gcgacaggat atgcccggcg ctacgggata daccggagtg tgttacaaag caggccaatt   6000
catagccaga aaaagtaaaa tcgctcatcg ttatacagct caggaaagtg actttagcca   6060
gcattacaat gctggtggtt cttactacgt ctgttagcgc gttgccgcga caggtaccag   6120
cacaccagca tcaagcaatc gcttcatcag ccactgctga cctttgccgg ttatacgagt   6180
cgtgaaagaa atcctgcttc cattgcttgt atcgatcacg gtttctttaa gggtgaaata   6240
cccacgagat atgtattctt gtttggggac gttcctgcgt tcaccggttg cgatcagaat   6300
tccgttatca cgcaaccagg tgaagagata gttttggccc aggccgagca ctttggcata   6360
gttgccgatt agaaccccgc tggcggtagc aacgcgttca gcgaattcga ctttaggtgc   6420
atccataagc attttttgct ccagccgttg cttttgctct gccaggtcgg cagccaaacg   6480
gagagcttca gggagactct gcggaatagc aggttgtaat cttccggttc gatagtcgat   6540
aaatgtctgg tttaccttca gccgaaacgc gggagaaatc cagcctgcgt actccacagc   6600
gagcaattca tgggcaaaag tgccgccgcc acggccttcg acctgcaggc atgcaagctt   6660
ggcgtaatca tggtcatagc tgtttcctgt gtgaaattgt tatccgctca caattccaca   6720
caacatacga gccggaagca taagtgtaa agcctggggt gcctaatgag tgagctaact    6780
cacattaatt gcgttgcgct cactgcccgc tttccagtcg ggaaacctgt cgtgccaggt   6840
agtcgatatg gtgcactctc agtacaatct gctctgatgc cgcatagtta agccagtata   6900
cactccgcta tcgctacgtg actgggtcat ggctgcgccc cgacacccgc caacacccgc   6960
tgacgcgccc tgacgggctt gtctgctccc ggcatccgct tacagacaag ctgtgaccgt   7020
ctccgggagc tgcatgtgtc agaggttttc accgtcatca ccgaaacgcg cgaggcagct   7080
gcggtaaagc tcatcagcgt ggtcgtgaag cgattcacag atgtctgcct gttcatccgc   7140
gtccagctcg ttgagtttct ccagaagcgt taatgtctgg cttctgataa agcgggccat   7200
gttaagggcg gttttttcct gtttggtcac tgatgcctcc gtgtaagggg gatttctgtt   7260 catggggta atgataccga tgaaacgaga gaggatgctc acgatacggg ttactgatga    7320
tgaacatgcc cggttactgg aacgttgtga gggtaaacaa ctggcggtat ggatgcggcg   7380
ggaccagaga aaaatcactc agggtcaatg ccagcgcttc gttaatacag atgtaggtgt   7440
tccacagggt agccagcagc atcctgcgat gcagatccgg aacataatgg tgcagggcgc   7500
tgacttccgc gtttccagac tttacgaaac acggaaaccg aagaccattc atgttgttgc   7560
```

```
tcaggtcgca gacgttttgc agcagcagtc gcttcacgtt cgctcgcgta tcggtgattc    7620
attctgctaa ccagtaaggc aaccccgcca gcctagccgg gtcctcaacg acaggagcac    7680
gatcatgcgc acccgtggcc aggacccaac gctgccgag atgcgccgcg tgcggctgct     7740
ggagatggcg gacgcgatgg atatgttctg ccaagggttg gtttgcgcat tcacagttct    7800
ccgcaagaat tgattggctc caattcttgg agtggtgaat ccgttagcga ggtgccgccg    7860
gcttccattc aggtcgaggt ggcccggctc catgcaccgc gacgcaacgc ggggaggcag    7920
acaaggtata gggcggcgcc tacaatccat gccaacccgt tccatgtgct cgccgaggcg    7980
gcataaatcg ccgtgacgat cagcggtcca atgatcgaag ttaggctggt aagagccgcg    8040
agcgatcctt gaagctgtcc ctgatggtcg tcatctacct gcctggacag catggcctgc    8100
aacgcgggca tcccgatgcc gccggaagcg agaagaatca taatgggaa ggccatccag     8160 cctcgcgtcg cgaacgccag caagacgtag cccagcgcgt cggccgccat gccggcgata    8220
atggcctgct tctcgccgaa acgtttggtg gcgggaccag tgacgaaggc ttgagcgagg    8280
gcgtgcaaga ttccgaatac cgcaagcgac aggccgatca tcgtcgcgct ccagcgaaag    8340
cggtcctcgc cgaaaatgac ccagagcgct gccggcacct gtcctacgag ttgcatgata    8400
aagaagacag tcataagtgc ggcgacgata gtcatgcccc gcgcccaccg gaaggagctg    8460
actgggttga ggctctcaag ggcatcggtc gagcttgaca ttgtaggacg tttaaacatt    8520
accctgttat ccctaggatc ctacgtaatc gatgaattcg atcccatttt tataactgga    8580
tctcaaaata cctataaacc cattgttctt ctcttttagc tctaagaaca atcaatttat    8640
aaatatattt attattatgc tataatataa atactatata aatacattta ccttttttata   8700 aatacattta ccttttttt aatttgcatg attttaatgc ttatgctatc tttttttattt    8760 agtccataaa acctttaaag gaccttttct tatgggatat ttatattttc ctaacaaagc    8820
aatcggcgtc ataaacttta gttgcttacg acgcctgtgg acgtccccc cttcccctta     8880 cgggcaagta aacttaggga ttttaatgca ataaataaat ttgtcctctt cgggcaaatg    8940
aattttagta tttaaatatg acaagggtga accattactt tgttaacaa gtgatcttac     9000 cactcactat ttttgttgaa ttttaaactt atttaaaatt ctcgagaaag atttaaaaa     9060 taaactttt taatctttta tttattttt ctttttcgt atggaattgc ccaatattat       9120
tcaacaattt atcggaaaca gcgttttaga gccaaataaa attggtcagt cgccatcgga    9180
tgtttattct tttaatcgaa ataatgaaac ttttttcct aagcgatcta gcactttata     9240
tacagagacc acatacagtg tctctcgtga agcgaaaatg ttgagttggc tctctgagaa    9300
attaaaggtg cctgaactca tcatgacttt tcaggatgag cagtttgaat ttatgatcac    9360
taaagcgatc aatgcaaaac caatttcagc gcttttttta acagaccaag aattgcttgc    9420
tatctataag gaggcactca atctgttaaa ttcaattgct attattgatt gtccatttat    9480
ttcaaacatt gatcatcggt taaaagagtc aaaatttttt attgataacc aactccttga    9540
cgatatagat caagatgatt ttgacactga attatgggga gaccataaaa cttacctaag    9600
tctatggaat gagttaaccg agactcgtgt tgaagaaaga ttggtttttt ctcatggcga    9660
tatcacggat agtaatatt ttatagataa attcaatgaa atttattttt tagaccttgg     9720
tcgtgctggg ttagcagatg aatttgtaga tatatccttt gttgaacgtt gcctaagaga    9780
ggatgcatcg gaggaaactg cgaaaatatt tttaaagcat ttaaaaaatg atagacctga    9840
caaaaggaat tatttttaa aacttgatga attgaattga ttccaagcat tatctaaaat     9900
actctgcagg cacgctagct tgtactcaag ctcgtaacga aggtcgtgac cttgctcgtg    9960
```

-continued

```
aaggtggcga cgtaattcgt tcagcttgta aatggtctcc agaacttgct gctgcatgtg    10020
aagtttggaa agaaattaaa ttcgaatttg atactattga caaactttaa tttttatttt    10080
tcatgatgtt tatgtgaata gcataaacat cgttttatt tttatggtgt ttaggttaaa    10140
tacctaaaca tcattttaca ttttttaaaat taagttctaa agttatcttt tgtttaaatt    10200
tgcctgtctt tataaattac gatgtgccag aaaaataaaa tcttagcttt ttattataga    10260
atttatcttt atgtattata ttttataagt tataataaaa gaaatagtaa catactaaag    10320
cggatgtagc gcgtttatct taacggaagg aattcggcgc ctacgtatac atactccgaa    10380
ggaggacaaa tttatttatt gtggtacaat aaataagtgg tacaataaat aaattgtatg    10440
taaacccctt cccccttcggg acgtcccctt acgggaatat aaatattagt ggcagttgcc    10500
tgccaacaaa tttatttatt gtattaacat aggcagtggc ggtaccactg ccactggcgt    10560
cctaatataa atattgggca actaaagttt atcgcagtat taacataggc agtggcggta    10620
ccactgccac tggcgtcctc cttcggagta tgtaaacctg ctaccgcagc aaataaattt    10680
tattctattt taatactaca atatttagat tcccgttagg ggataggcca ggcaattgtc    10740
actggcgtca tagtatatca atattgtaac agattgacac cctttaagta aacatttttt    10800
ttaggattca tatgaaatta aatggatatt tggtacattt aattccacaa aaatgtccaa    10860
tacttaaaat acaaaattaa aagtattagt tgtaaacttg actaacattt taaattttaa    10920
attttttcct aattatatat tttacttgca aaatttataa aaatttatg catttttata    10980 tcataataat aaaaccttta ttcatggttt ataatataat aattgtgatg actatgcaca    11040
aagcagttct agtcccatat atataactat atataacccg tttaaagatt tatttaaaaa    11100
tatgtgtgta aaaaatgctt atttttaatt ttattttata taagttataa tattaaatac    11160
acaatgatta aaattaaata ataataaatt taacgtaacg atgagttgtt tttttatttt    11220
ggagatacac gcaatgacaa ttgcgatcgg tacatatcaa gagaaacgca catggttcga    11280
tgacgctgat gactggcttc gtcaagaccg tttcgtattc gtaggttggt caggtttatt    11340
actattccct tgtgcttact ttgcaactcc ggtccggcgg ccgcctcgag acgacttgtc    11400
cgcttcatca gacacggctt tcctaaccat caatggtgga ttttcaggaa agacgtttaa    11460
agaagtggca taaagtttat ttgttgaaga attggttttg tttccattca aagaattgtt    11520
agggataaaa ctttgcattt ttttataatt tgttataagt ttttcaaact tatatgtttt    11580
taaaaatgca tttaattgct tattaatgcg ttcattttgt aatgtttcaa taggtcttgc    11640
ttgcgctaat cgcagtattc ccgatacttt gtctgcttgt ttttcgggta ttgagaataa    11700
gtaagtataa tgatttaaaa aagtcatgtt ttgattaaat ctttttttata tggttaaaaa    11760 cattatggta tatctaaata aatttatttt ttactaaatc tccaatttgc aatttagaga    11820
tataattaaa actataaagt tatttaagtt aatttgtaat caaatccaac acaaaaatgt    11880
ttttatatag ttaacatgtt aaatttaaca tatgttaaac aactaaaatt ctgtaacaga    11940
gaacaataaa ataaatgcta gattttgtgt aatgccgaag tatatttata tacttccctt    12000
tcaaaaaaat aaatactctt gccactaaaa ttcatttgcc taggacgtcc ccttcccctt    12060
acgggatgtt tatatactag gacgtcccct tccccttacg ggatatttat atactccgaa    12120
ggacgtcccc ttcgggcaaa taatttttag tggcagttgc ctgccaactg cctaggcaag    12180
taaacttagg gattttaatg caataaataa atttgtcccc ttacgggacg tcagtggcag    12240
ttgcctgcca actgcctaat ataaatatta gtggatattt atatactccg aaggaggcag    12300
ttacctgcca actgccgagg caaataaatt ttagtggcag tggtaccgcc actgcctgct    12360
```

```
ccctccttcc ccttcgggca agtaaactta gcatgttgtc gacattaccc tgttatccct   12420
aggccggcct aagaaaccat tattatcatg acattaacct ataaaaatag gcgtatcacg   12480
aggcccttcc gtcttcaaga aattcggtcg aaaaagaaa aggagagggc caagagggag   12540
ggcattggtg actattgagc acgtgagtat acgtgattaa gcacacaaag gcagcttgga   12600
gtatgtctgt tattaatttc acaggtagtt ctggtccatt ggtgaaagtt tgcggcttgc   12660
agagcacaga ggccgcagaa tgtgctctag attccgatgc tgacttgctg ggtattatat   12720
gtgtgcccaa tagaaagaga acaattgacc cggttattgc aaggaaaatt tcaagtcttg   12780
taaaagcata taaaaatagt tcaggcactc cgaaatactt ggttggcgtg tttcgtaatc   12840
aacctaagga ggatgttttg gctctggtca atgattacgg cattgatatc gtccaactgc   12900
atggagatga gtcgtggcaa gaataccaag agttcctcgg tttgccagtt attaaaagac   12960
tcgtatttcc aaaagactgc aacatactac tcagtgcagc ttcacagaaa cctcattcgt   13020
ttattccctt gtttgattca gaagcaggtg ggacaggtga acttttggat tggaactcga   13080
tttctgactg ggttggaagg caagagagcc ccgaaagctt acattttatg ttagctggtg   13140
gactgacgcc agaaaatgtt ggtgatgcgc ttagattaaa tggcgttatt ggtgttgatg   13200
taagcggagg tgtggagaca aatggtgtaa aagactctaa caaaatagca aatttcgtca   13260
aaaatgctaa gaaataggtt attactgagt agtatttatt taagtattgt ttgtgcactt   13320
gcctgcaggc ctttgaaaa gcaagcataa aagatctaaa cataaaatct gtaaaataac   13380
aagatgtaaa gataatgcta aatcatttgg ctttttgatt gattgtacag gaaaatatac   13440
atcgcagggg gttgacttt accatttcac cgcaatggaa tcaaacttgt tgaagagaat   13500
gttcacaggc gcatacgcta caatgacccg attcttgcta gccttttctc ggtcttgcaa   13560
acaaccgccg gcagcttagt atataaatac acatgtacat acctctctcc gtatcctcgt   13620
aatcattttc ttgtatttat cgtcttttcg ctgtaaaaac tttatcacac ttatctcaaa   13680
tacacttatt aaccgctttt actattatct tctacgctga cagtaatatc aaacagtgac   13740
acatattaaa cacagtggtt tctttgcata aacaccatca gcctcaagtc gtcaagtaaa   13800
gatttcgtgt tcatgcagat agataacaat ctatatgttg ataattagcg ttgcctcatc   13860
aatgcgagat ccgtttaacc ggaccctagt gcacttaccc cacgttcggt ccactgtgtg   13920
ccgaacatgc tccttcacta ttttaacatg tggaattaat tctaaatcct ctttatatga   13980
tctgccgata gatagttcta agtcattgag gttcatcaac aattggattt tctgtttact   14040
cgacttcagg taatgaaatg agatgatact tgcttatctc atagttaact ggcataaatt   14100
ttagtatagg ttaactctaa gaggtgatac ttatttactg taaaactgtg acgataaaac   14160
cggaaggaag aataagaaaa ctcgaactga tctataatgc ctattttctg taaagagttt   14220
aagctatgaa agcctcggca ttttggccgc tcctaggtag tgctttttt ccaaggacaa   14280 aacagtttct ttttcttgag caggtttat gtttcggtaa tcataaacaa taaataaatt   14340
atttcattta tgtttaaaaa taaaaaataa aaagtatttt taaatttta aaaagttga   14400 ttataagcat gtgacctttt gcaagcaatt aaattttgca atttgtgatt taggcaaaag   14460
ttactatttc tggctcgtgt aatatatgta tgctaatgtg aacttttaca aagtcgatat   14520
ggacttagtc aaaagaaatt ttcttaaaaa tatatagcac tagccaattt agcacttctt   14580
tatgagatat attatagact ttattaagcc agatttgtgt attatatgta tttaccggc   14640 gaatcatgga catacattct gaaataggta atattctcta tggtgagaca gcatagataa   14700
cctaggatac aagttaaaag ctagtactgt tttgcagtaa tttttttctt ttttataaga   14760
```

```
atgttaccac ctaaataagt tataaagtca atagttaagt ttgatatttg attgtaaaat    14820
accgtaatat atttgcatga tcaaaaggct caatgttgac tagccagcat gtcaaccact    14880
atattgatca ccgatattag gacttccaca ccaactagta atatgacaat aaattcaaga    14940
tattcttcat gagaatggcc cagctcatgt ttgacagctt atcatcgata agctttaatg    15000
cggtagttta tcacagttaa attgctaacg cagtcaggca ccgtgtatga aatctaacaa    15060
tgcgctcatc gtcatcctcg gcaccgtcac cctggatgct gtaggcatag gcttggttat    15120
gccggtactg ccgggcctct tgcgggatat cgtccattcc gacagcatcg ccagtcacta    15180
tggcgtgctg ctagcgctat atgcgttgat gcaatttcta tgcgcacccg ttctcggagc    15240
actgtccgac cgctttggcc gccgcccagt cctgctcgct tcgctacttg gagccactat    15300
cgactacgcg atcatggcga ccacacccgt cctgtggatc aattctttag tataaatttc    15360
actctgaacc atcttggaag gaccggataa ttatttgaaa tctcttttc aattgtatat    15420 gtgttatgta gtatactctt tcttcaacaa ttaaatactc tcggtagcca agttggttta    15480
aggcgcaaga ctttaattta tcactacgga attggcctat taggcctacc cactagtcaa    15540
ttcgggagga tcgaaacggc agatcgcaaa aaacagtaca tacagaagga gacatgaaca    15600
tgaacatcaa aaaaattgta aaacaagcca cagttctgac ttttacgact gcacttctgg    15660
caggaggagc gactcaagcc ttcgcgaaag aaaataacca aaaagcatac aaagaaacgt    15720
acggcgtctc tcatattaca cgccatgata tgctgcagat ccctaaacag cagcaaaacg    15780
aaaaatacca agtgcctcaa ttcgatcaat caacgattaa aaatattgag tctgcaaaag    15840
gacttgatgt gtgggacagc tggccgctgc aaaacgctga cggaacagta gctgaataca    15900
acggctatca cgttgtgttt gctcttgcgg gaagcccgaa agacgctgat gacacatcaa    15960
tctacatgtt ttatcaaaag gtcggcgaca actcaatcga cagctggaaa aacgcgggcc    16020 gtgtcttta agacagcgat aagttcgacg ccaacgatcc gatcctgaaa gatcagacgc    16080
aagaatggtc cggttctgca acctttacat ctgacggaaa aatccgttta ttctacactg    16140
actattccgg taaacattac ggcaaacaaa gcctgacaac agcgcaggta aatgtgtcaa    16200
aatctgatga cacactcaaa atcaacggag tggaagatca caaaacgatt tttgacggag    16260
acggaaaaac atatcagaac gttcagcagt ttatcgatga aggcaattat acatccggcg    16320
acaaccatac gctgagagac cctcactacg ttgaagacaa aggccataaa taccttgtat    16380
tcgaagccaa cacgggaaca gaaaacggat accaaggcga agaatcttta tttaacaaag    16440
cgtactacgg cggcggcacg aacttcttcc gtaaagaaag ccagaagctt cagcagagcg    16500
ctaaaaaacg cgatgctgag ttagcgaacg gcgccctcgg tatcatagag ttaaataatg    16560
attacacatt gaaaaaagta atgaagccgc tgatcacttc aaacacggta actgatgaaa    16620
tcgagcgcgc gaatgttttc aaaatgaacg gcaaatggta cttgttcact gattcacgcg    16680
gttcaaaaat gacgatcgat ggtattaact caaacgatat ttacatgctt ggttatgtat    16740
caaactcttt aaccgccct tacaagccgc tgaacaaaac agggcttgtg ctgcaaatgg    16800
gtcttgatcc aaacgatgtg acattcactt actctcactt cgcagtgccg caagccaaag    16860
gcaacaatgt ggttatcaca agctacatga caaacagagg cttcttcgag gataaaaagg    16920
caacatttgc gccaagcttc ttaatgaaca tcaaaggcaa taaacatcc gttgtcaaaa    16980 acagcatcct ggagcaagga cagctgacag tcaactaata acagcaaaaa gaaaatgccg    17040
atacttcatt ggcattttct tttatttctc aacaagatgg tgaattgact agtgggtaga    17100
tccacaggac gggtgtggtc gccatgatcg cgtagtcgat agtggctcca agtagcgaag    17160
```

```
cgagcaggac tgggcggcgg ccaaagcggt cggacagtgc tccgagaacg ggtgcgcata  17220
gaaattgcat caacgcatat agcgctagca gcacgccata gtgactggcg atgctgtcgg  17280
aatggacgat atcccgcaag aggcccggca gtaccggcat aaccaagcct atgcctacag  17340
catccagggt gacggtgccg aggatgacga tgagcgcatt gttagatttc atacacggtg  17400
cctgactgcg ttagcaattt aactgtgata aactaccgca ttaaagctta tcgatgataa  17460
gctgtcaaac atgagaattg atccggaacc cttaatataa cttcgtataa tgtatgctat  17520
acgaagttat taggtccctc gactacgtcg ttaaggccgt ttctgacaga gtaaaattct  17580
tgagggaact ttcaccatta tgggaaatgg ttcaagaagg tattgactta aactccatca  17640
aatggtcagg tcattgagtg ttttttattt gttgtatttt ttttttttag agaaaatcct  17700
ccaatatata aattaggaat catagtttca tgattttctg ttacacctaa cttttttgtgt 17760
ggtgccctcc tccttgtcaa tattaatgtt aaagtgcaat tctttttcct tatcacgttg  17820
agccattagt atcaatttgc ttacctgtat tcctttacat cctcctttt ctccttcttg  17880
ataaatgtat gtagattgcg tatatagttt cgtctaccct atgaacatat tccattttgt  17940
aatttcgtgt cgtttctatt atgaatttca tttataaagt ttatgtacaa atatcataaa  18000
aaaagagaat cttttttaagc aaggattttc ttaacttctt cggcgacagc atcaccgact  18060
tcggtggtac tgttggaacc acctaaatca ccagttctga tacctgcatc caaacccttt  18120
ttaactgcat cttcaatggc cttaccttct tcaggcaagt tcaatgacaa tttcaacatc  18180
attgcagcag acaagatagt ggcgataggg ttgaccttat tctttggcaa atctggagca  18240
gaaccgtggc atggttcgta caaccaaat gcggtgttct tgtctggcaa agaggccaag  18300
gacgcagatg gcaacaaacc caaggaacct gggataacgg aggcttcatc ggagatgata  18360
tcaccaaaca tgttgctggt gattataata ccatttaggt gggttgggtt cttaactagg  18420
atcatggcgg cagaatcaat caattgatgt tgaaccttca atgtagggaa ttcgttcttg  18480
atggtttcct ccacagtttt tctccataat cttgaagagg ccaaaacatt agctttatcc  18540
aaggaccaaa taggcaatgg tggctcatgt tgtagggcca tgaaagcggc cattcttgtg  18600
attctttgca cttctggaac ggtgtattgt tcactatccc aagcgacacc atcaccatcg  18660
tcttcctttc tcttaccaaa gtaaatacct cccactaatt ctctgacaac aacgaagtca  18720
gtacctttag caaattgtgg cttgattgga gataagtcta aaagagagtc ggatgcaaag  18780
ttacatggtc ttaagttggc gtacaattga agttctttac ggattttttag taaaccttgt  18840
tcaggtctaa cactaccggt accgcgcttg cggaagcatc agcaaataag gccagcacag  18900
ccagcgcagt tgccgctttg gttcctgatt ctgttcttga tgaattaaac aaagcggcac  18960
agtaacaaag gacttcattg ataattttc ttcaggagga agacatgtca ttctttttcta  19020
cgttaaaaac agctttgtct ttgaaggaga aacttgctgc tactggtgtt cttgttctga  19080
tttgcgcact tgttggtgct gggtttgcat gggaacgtca tcagctaaag caagccatag  19140
agaaaattgg cagtcttgat caggctgtta aggaacgtga taagtcaata atggatctta  19200
accagaccat tgagacgatg aacaaagcag agcaacattt tcacagccag gaagtgaaaa  19260
atgaatcaga acaagccaag tatgctgaca ggcaaatgga acgaaaagct gaagttcaga  19320
aacaactggt tgcggcgggt aatgttcgcc agcgtattcc tgctgacact cagcggttgc  19380
tccgggagtc gatcagcgaa tttaacgccg acgccgacaa aggttaacca ccctgccccc  19440
aaaagtgcat ttatgtgtag gatgccgagg tttagcagtg aatattttga tgatctgcca  19500
gcgtatatcc tcgatacaga aacgatgctg atggggatta acaggaagaa tcgcaacgtt  19560
```

```
aatgattaca accgagctat tagcggtaac taaaagggat ttttatgtct gataaagtaa    19620
cagtaaagca aactatcaac aaagcgactt caatctacaa aattgagcaa atcactgttg    19680
gcaagccagg atctgaacaa taccgtcgtg ctttcgagct tgccgatcag cttggtttaa    19740
aacacccgga ttgcattgag catgtatttc cgacctatgc tgatgagcaa tgtactcatg    19800
ttcttaccga agaggatttt ttcagcactg aagaacgaga aggcgttgat cgctgcattg    19860
gtgtgatttg ttcttcggta agtgatgagt tattccctaa tgtgcctgaa tatggtggta    19920
ttggatacca attcctgtac gagggcgatg agcttaaatg ctatgaacat ggtcttctca    19980
tcgaaagcgt agaataatac gactcccttc caaccggcta cgttggccgg tttttcactt    20040
atccacatta tccactggat agatccaata atcaggtcca tacagatccc aattagatcc    20100
atatagatcc ctgatcgttg caggccgcgc cacgtctggc ttagaagtgt atcgcgatgt    20160
gtgctggagg gaaaacgatg tgtgctggag ggataaaaat gtgtgctgac gggttgctaa    20220
tgtgtgctgg cgggatatag gatgtgtgtt gacgggaaag cttgggtagt tatcaccact    20280
tataaaaact atccacacaa ttcggaaaaa gtaatatgaa tcaatcattt atctccgata    20340
ttctttacgc agacattgaa agtaaggcaa agaactaac agttaattca aacaacactg    20400
tgcagcctgt agcgttgatg cgcttggggg tattcgtgcc gaagccatca agagcaaag    20460 gagaaagtaa agagattgat gccaccaaag cgttttccca gctggagata gctaaagccg    20520
agggttacga tgatattaaa atcaccggtc ctcgactcga tatggatact gatttcaaaa    20580
cgtggatcgg tgtcatctac gcgttcagca aatacggctt gtcctcaaac accatccagt    20640
tatcgtttca ggaattcgct aaagcctgtg gtttcccctc aaaacgtctg gatgcgaaac    20700
tgcgtttaac cattcatgaa tcacttggac gcttgcgtaa caagggtatc gcttttaagc    20760
gcggaaaaga tgctaaaggc ggctatcaga ctggtctgct gaaggtcggg cgttttgatg    20820
ctgaccttga tctgatagag ctggaggctg attcgaagtt gtgggagctg ttccagcttg    20880
attatcgcgt tctgttgcaa caccacgcct tgcgtgccct tccgaagaaa gaagctgcac    20940
aagccattta cactttcatc gaaagccttc cgcagaaccc gttgccgcta tcgttcgcgc    21000
gaatccgtga gcgcctggct ttgcagtcag ctgttggcga gcaaaaccgt atcattaaga    21060
aagcgataga acagcttaaa acaatcggct atctcgactg ttctattgag aagaaaggcc    21120
gggaaagttt tgtaatcgtc cattctcgca atccaaagct gaaactcccc gaataagtgt    21180
gtgctggagg gaaaccgcat taaaagatg tgtgctgccg ggaaggcttg tccaatttcc    21240
tgtttttgat gtgcgctgga gggggacgcc cctcagtttg cccagacttt ccctccagca    21300
cacatctgtc catccgcttt tccctccagt gcacatgtaa ttctctgcct ttccctccag    21360
cacacatatt tgataccagc gatccctcca cagcacataa ttcaatgcga cttccctcta    21420
tcgcacatct tagacttta ttctccctcc agcacacatc gaagctgccg ggcaagccgt    21480
tctcaccagt tgatagagag tgaagcttgg ctgcccattg aagcaggaaa tcaccaaaat    21540
gattcaggct acaacctgaa cgtagaagaa atccgcgtcc tttatgcgtg gaggatgcca    21600
aagcatgttg tgacacactt ggcaaaggag taagcatgca gagaatgcta tgtacaagca    21660
tctacgcata cattattatt ttatgcagca tttttaatta aattcaaaaa tacagcataa    21720
aggatgactt tcgatgagtg attccagcca gcttcacaag gttgctcaaa gagcaaacag    21780
aatgctcaat gttctgactg aacaagtaca gttgcaaaag gatgagctac acgcgaacga    21840
gttttaccag gtctatgcga aagcggcact ggcaaaattg cctctactga ctcgagcgaa    21900
cgttgactat gccgtaagtg aaatggaaga aaagggttat gttttcgata aacgccctgc    21960
```

```
tggctcttca atgaaatatg cgatgtcaat tcagaacatc attgacatat atgaacatcg    22020
cggagtgcca aaataccggg atcgctacag cgaagcgtat gtgattttca tctccaatct    22080
taaaggcggt gtgtcaaaaa ctgtatcgac ggtttctctg cgcatgcaa tgcgtgctca     22140 ccctcatctt cttatggagg atttaaggat tctggttatt gaccttgatc cgcaatcttc    22200
agcaacgatg ttttaagcc ataaacactc tattggtatc gtaaacgcaa catctgcaca    22260
ggctatgttg cagaatgtaa gccgtgaaga gctgttagag gagtttattg ttccttctgt    22320
tgtacctggg gttgacgtta tgcctgcgtc gattgacgat gcctttattg catccgattg    22380
gagagagctg tgcaatgagc atctaccggg tcagaacatc catgctgtcc tgaaagaaaa    22440
tgtgattgat aagctgaaga gcgattatga ctttatcctc gttgatagtg gtcctcacct    22500
tgacgccttc ctgaaaaatg cttttggcct ggccaatata ctgtttacac ctctgccgcc    22560
agcaactgtc gatttccact catcgcttaa atacgttgcc cgccttcctg agttggtgaa    22620
actcatttcg gatgaaggct gcgagtgcca gcttgcgact aacattggtt ttatgtccaa    22680
gttgagtaac aaggcagacc ataagtattg ccatagcctg gctaaagaag tgttcggtgg    22740
ggatatgctt gatgtcttcc tccctcgcct tgacggtttt gaacgctgcg gcgagtcttt    22800
tgacactgtt atttcagcta acccggcaac gtatgttggt agtgctgatg cattgaagaa    22860
cgcgcgaatt gccgcggaag attttgctaa agcagttttt gaccgtat                 22908
```

<210> SEQ ID NO 7
<211> LENGTH: 7870
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
gtgcactctc agtacaatct gctctgatgc cgcatagtta agccagcccc gacacccgcc      60
aacacccgct gacgcgccct gacgggcttg tctgctcccg gcatccgctt acagacaagc     120
tgtgaccgtc tccgggagct gcatgtgtca gaggttttca ccgtcatcac cgaaacgcgc     180
gagacgaaag ggcctcgtga tacgcctatt tttataggtt aatgtcatga taataatggt     240
ttcttagacg tcaggtggca cttttcgggg aaatgtgcgc ggaaccccta tttgtttatt     300
tttctaaata cattcaaata tgtatccgct catgagacaa taaccctgat aaatgcttca     360
ataatattga aaaaggaaga gtatgagtat tcaacatttc cgtgtcgccc ttattccctt     420
ttttgcggca ttttgccttc ctgttttttgc tcacccagaa acgctggtga agtaaaaga     480 tgctgaagat cagttgggtg cacgagtggg ttacatcgaa ctggatctca acagcggtaa     540
gatccttgag agttttcgcc ccgaagaacg ttttccaatg atgagcactt ttaaagttct     600
gctatgtggc gcggtattat cccgtattga cgccgggcaa gagcaactcg gtcgccgcat     660
acactattct cagaatgact tggttgagta ctcaccagtc acagaaaagc atcttacgga     720
tggcatgaca gtaagagaat tatgcagtgc tgccataacc atgagtgata acactgcggc     780
caacttactt ctgacaacga tcggaggacc gaaggagcta accgcttttt tgcacaacat     840
gggggatcat gtaactcgcc ttgatcgttg ggaaccggag ctgaatgaag ccataccaaa     900
cgacgagcgt gacaccacga tgcctgtagc aatggcaaca acgttgcgca aactattaac     960
tggcgaacta cttactctag cttcccggca acaattaata gactggatgg aggcggataa    1020
agttgcagga ccacttctgc gctcggccct tccggctggc tggtttattg ctgataaatc    1080
```

```
tggagccggt gagcgtgggt ctcgcggtat cattgcagca ctggggccag atggtaagcc    1140
ctcccgtatc gtagttatct acacgacggg gagtcaggca actatggatg aacgaaatag    1200
acagatcgct gagataggtg cctcactgat taagcattgg taactgtcag accaagttta    1260
ctcatatata ctttagattg atttaaaact tcatttttaa tttaaaagga tctaggtgaa    1320
gatccttttt gataatctca tgaccaaaat cccttaacgt gagttttcgt tccactgagc    1380
gtcagacccc gtagaaaaga tcaaaggatc ttcttgagat cctttttttc tgcgcgtaat    1440
ctgctgcttg caaacaaaaa aaccaccgct accagcggtg gtttgtttgc cggatcaaga    1500
gctaccaact cttttccga aggtaactgg cttcagcaga gcgcagatac caaatactgt     1560
tcttctagtg tagccgtagt taggccacca cttcaagaac tctgtagcac cgcctacata    1620
cctcgctctg ctaatcctgt taccagtggc tgctgccagt ggcgataagt cgtgtcttac    1680
cgggttggac tcaagacgat agttaccgga taaggcgcag cggtcgggct gaacggggggg    1740 ttcgtgcaca gcccagct tggagcgaac gacctacacc gaactgagat acctacagcg      1800
tgagctatga gaaagcgcca cgcttcccga agggagaaag gcggacaggt atccggtaag    1860
cggcagggtc ggaacaggag agcgcacgag ggagcttcca gggggaaacg cctggtatct    1920
ttatagtcct gtcgggtttc gccacctctg acttgagcgt cgatttttgt gatgctcgtc    1980
aggggggcgg agcctatgga aaaacgccag caacgcggcc ttttttacggt tcctggcctt    2040 ttgctggcct tttgctcaca tgttctttcc tgcgttatcc cctgattctg tggataaccg    2100
tattaccgcc tttgagtgag ctgataccgc tcgccgcagc cgaacgaccg agcgcagcga    2160
gtcagtgagc gaggaagcgg aagagcgccc aatacgcaaa ccgcctctcc ccgcgcgttg    2220
gccgattcat taatgcagct ggcacgacag gtttcccgac tggaaagcgg gcagtgagcg    2280
caacgcaatt aatgtgagtt agctcactca ttaggcaccc caggctttac actttatgct    2340
tccggctcgt atgttgtgtg gaattgtgag cggataacaa tttcacacag gaaacagcta    2400
tgaccatgat tacgccaagc tcgcggccgc agtactctgc agatttttatg caaaattaaa    2460 gtcttgtgac aacagctttc tccttaagtg caaatatcgc ccattctttc ctcttttcgt    2520
atataaatgc tgtaatagta ggatgtcgta cccgtaaagg tacgacattg aatattaata    2580
tactcctaag tttactttcc caatatttat attaggacgt ccccttcggg taaataaatt    2640
ttagtggcag tggtaccgcc actccctatt ttaatactgc gaaggaggca gttggcaggc    2700
aactcgtcgt tcgcagtata taaatatcca ctaatattta tattcccgta aggggacgtc    2760
ccgaagggga aggggaaaga agcagtcgcc tccttgcgaa aaggtttact tgcccgacca    2820
gtgaaaagca tgctgtaaga tataaatcta ccctgaaagg gatgcatttc accataatac    2880
tatacaaatg gtgttacct ttgaggatca taacggtgct actggaatat atggtctctt     2940
catggataga cgatagccat ttatttaccc attaagggga cattagtggc ctgtcactgc    3000
tccttacgag acgccagtgg acgttcgtcc tagaaaattt atgcgctgcc tagaagcccc    3060
aaaagggaag tttactgact cgttagagcg tgcgctaaca ggtttaaata cttcaatatg    3120
tatattagga cgccggtggc agtggtaccg ccactgccac cgtcggagga cgtcccttac    3180
ggtatattat atactaggat tttaatactc cgaaggaggc agtggcggta ccactgccac    3240
taatatttat attcccgtaa gggacgtcct ccttcggagt atgtaaacat tctaagttta    3300
cttgcccaat atttatatta ggcagttggc aggcaactgc tagctctcct ccttcggagt    3360
atgtaaacat cgcagtatat aaatatccac taatatttat attcccgtaa ggggacgtcc    3420
cgaaggggaa ggggaaggac gtcagtggca gttgcctgcc aactgcctag gcaagtaaac    3480
```

```
ttaggagtat ataaatatag gcagtcgcgg taccactgcc actgacgtcc tgccaactgc    3540
ctaggcaagt aaacttaagt ggcactaaaa tgcatttgcc cgaaggggaa ggaggacgcc    3600
agtggcagtg gtaccgccac tgcctccttc ggagtattaa aatcctagta tgtaaatctg    3660
ctagcgcagg aaataaattt tattctattt atatactccg ttaggaggta agtaaacccc    3720
ttccccttcg ggacgtcagt gcagttgcct gccaactgcc taatataaat attagaccac    3780
taaagtttgg caactgccaa ctgttgtcct tcggaggaaa aaaaatggtt aactcgcaag    3840
cagttaacat aactaaagtt tgttacttta ccgaagacgt ttacccttc tcggttaagg     3900 agacggagac agttgcactg tgactgccta gtatagcaat tttgtttttg tttatatgct    3960
cgacaaaatg actttcataa aaatataaag tagttagcta gttattttat atcactataa    4020
ctagggttct cagaggcacc gaagtcactt gtaaaaatag tacttttta cttgtttaat     4080 cttcgtgttc ttcaaaagga tcacgtaatt tttttgaagg tggaccaaaa ctaacataaa    4140
ctgaatagcc agttacactt aacagaagaa accataaaaa aaaggtaaag aaaaaagctg    4200
gactttccat agctcatta ataataaaat tattctcttt tcaacatatc tcttagatag     4260
ttcaaaagac ttgacgactg tgtcccacat ttttaaacaa aattaatcta ctcaaaattt    4320
tgccctgaga aagaataact tacttcgttt ttgcagtagc cattcatgtc actttgaaac    4380
tgtccttaca aagttaaaca ttaattaaaa attatttaat ttttatataa caaatattat    4440
attaaataaa aaatgaacaa agaacttcta agatcgtctt tagtgagtaa ttaaagagtt    4500
ttacttacca gacaaggcag ttttttcatt cttttaaagc aggcagttct gaaggggaaa    4560
agggactgcc tactgcggtc ctaggtaaat acattttat gcaatttatt tcttgtgcta     4620
gtaggtttct atactcacaa gaagcaaccc cttgacgaga gaacgttatc ctcagagtat    4680
ttataatcct gagagggaat gcactgaaga atattttcct tatttttac agaaagtaaa     4740 taaaatagcg ctaataacgc ttaattcatt taatcaatta tggcaacagg aacttctaaa    4800
gctaaaccat caaaagtaaa ttcagacttc caagaacctg gtttagttac accattaggt    4860
actttattac gtccacttaa ctcagaagca ggtaaagtat taccaggctg gggtacaact    4920
gttttaatgg ctgtatttat cctttattt gcagcattct tattaatcat tttagaaatt     4980
tacaacagtt ctttaatttt agatgacgtt tctatgagtt gggaaacttt agctaaagtt    5040
tcttaatttt atttaacaca aacataaaat ataaaactgt tgttaaggc tagctgctaa     5100 gtcttctttt cgctaaggta aactaagcaa ctcaaccata tttatattcg gcagtggcac    5160
cgccaactgc cactggcctt ccgttaagat aaacgcgtgg atctcacgtg actagtgata    5220
tctacgtaat cgatgaattc gatcccattt ttataactgg atctcaaaat acctataaac    5280
ccattgttct tctcttttag ctctaagaac aatcaattta taaatatatt tattattatg    5340
ctataatata aatactatat aaatacattt acctttttat aaatacattt acctttttt    5400 taatttgcat gattaatg cttatgctat cttttttatt tagtccataa aacctttaaa     5460 ggacctttc ttatgggata tttatatttt cctaacaaag caatcggcgt cataaacttt     5520
agttgcttac gacgcctgtg gacgtccccc ccttcccctt acgggcaagt aaacttaggg    5580 atttaatgc aataaataaa tttgtcctct tcgggcaaat gaattttagt atttaaatat     5640
gacaagggtg aaccattact tttgttaaca agtgatctta ccactcacta tttttgttga    5700
attttaaact tatttaaaat tctcgagaaa gatttaaaa ataaacttt ttaatctttt      5760 atttattttt tctttttcg tatggctcgt gaagcggtta tcgccgaagt atcaactcaa     5820
ctatcagagg tagttggcgt catcgagcgc catctcgaac cgacgttgct ggccgtacat    5880
```

```
ttgtacggct ccgcagtgga tggcggcctg aagccacaca gtgatattga tttgctggtt    5940
acggtgaccg taaggcttga tgaaacaacg cggcgagctt tgatcaacga ccttttggaa    6000
acttcggctt cccctggaga gagcgagatt ctccgcgctg tagaagtcac cattgttgtg    6060
cacgacgaca tcattccgtg gcgttatcca gctaagcgcg aactgcaatt tggagaatgg    6120
cagcgcaatg acattcttgc aggtatcttc gagccagcca cgatcgacat tgatctggct    6180
atcttgctga caaaagcaag agaacatagc gttgccttgg taggtccagc ggcggaggaa    6240
ctctttgatc cggttcctga acaggatcta tttgaggcgc taaatgaaac cttaacgcta    6300
tggaactcgc cgcccgactg ggctggcgat gagcgaaatg tagtgcttac gttgtcccgc    6360
atttggtaca gcgcagtaac cggcaaaatc gcgccgaagg atgtcgctgc cgactgggca    6420
atggagcgcc tgccggccca gtatcagccc gtcatacttg aagctagaca ggcttatctt    6480
ggacaagaag aagatcgctt ggcctcgcgc gcagatcagt tggaagaatt tgtccactac    6540
gtgaaaggcg agatcactaa ggtagttggc aaataattcc aagcattatc taaaatactc    6600
tgcaggcacg ctagcttgta ctcaagctcg taacgaaggt cgtgaccttg ctcgtgaagg    6660
tggcgacgta attcgttcag cttgtaaatg gtctccagaa cttgctgctg catgtgaagt    6720
ttggaaagaa attaaattcg aatttgatac tattgacaaa ctttaatttt tattttttcat   6780
gatgtttatg tgaatagcat aaacatcgtt tttattttta tggtgtttag gttaaatacc    6840
taaacatcat tttacatttt taaaattaag ttctaaagtt atcttttgtt taaatttgcc    6900
tgtctttata aattacgatg tgccagaaaa ataaaatctt agcttttttat tatagaattt   6960
atctttatgt attatatttt ataagttata ataaaagaaa tagtaacata ctaaagcgga    7020
tgtagcgcgt ttatcttaac ggaaggaatt cggcgcctac gtacccgggt cgcgaggatc    7080
cacgcgttaa tagctcactt ttctttaaat ttaattttta atttaaaggt gtaagcaaat    7140
tgcctgacga gagatccact taaggatgac cagtggcggg ctactgccta cttccctccg    7200
ggataaaatt tatttgaaaa acgttagtta cttcctaacg gagcattgac atccccatat    7260
ttatattagg acgtcccctt cgggtaaata aattttagtg gacgtcccct tcgggcaaat    7320
aaattttagt ggacaataaa taaatttgtt gcctgccaac tgcctaggca agtaaacttg    7380
ggagtattaa aataggacgt cagtggcagt tgcctgccaa ctgcctatat ttatatactg    7440
cgaagcaggc agtggcggta ccactgccac tggcgtccta atataaatat tgggcaacta    7500
aagtttatag cagtattaac atcctatatt tatatactcc gaaggaactt gttagccgat    7560
aggcgaggca acaaatttat ttattgtccc gtaaaaggat gcctccagca tcgaggggga    7620
aggggacgtc ctaggccata aaactaaagg gaaatccata gtaactgatg ttataaattt    7680
atagactcca aaaacagct gcgttataaa taacttctgt taaatatggc caaggggaca    7740
ggggcacttt caactaagtg tacattaaaa attgacaatt caatttttt taattataat    7800
atatatttag taaatataa caaaagccc ccatcgtcta ggtagaattc cagctggcgg    7860
ccgccctatg                                                          7870
```

<210> SEQ ID NO 8
<211> LENGTH: 1353
<212> TYPE: DNA
<213> ORGANISM: Saccharomyces cerevisiae

<400> SEQUENCE: 8

```
tcgcgcgttt cggtgatgac ggtgaaaacc tctgacacat gcagctcccg gagacggtca     60
cagcttgtct gtaagcggat gccgggagca gacaagcccg tcagggagcg cgtcagcggg    120
```

| | |
|---|---:|
| tgttggcggg tgtcggggct ggcttaacta tgcggcatca gagcagattg tactgagagt | 180 |
| gcaccatacc acagcttttc aattcaattc atcattttt tttattctt tttttttgatt | 240 |
| tcggtttctt tgaaattttt ttgattcggt aatctccgaa cagaaggaag aacgaaggaa | 300 |
| ggagcacaga cttagattgg tatatatacg catatgtagt gttgaagaaa catgaaattg | 360 |
| cccagtattc ttaacccaac tgcacagaac aaaaacctgc aggaaacgaa gataaatcat | 420 |
| gtcgaaagct acatataagg aacgtgctgc tactcatcct agtcctgttg ctgccaagct | 480 |
| atttaatatc atgcacgaaa agcaaacaaa cttgtgtgct tcattggatg ttcgtaccac | 540 |
| caaggaatta ctggagttag ttgaagcatt aggtcccaaa atttgtttac taaaaacaca | 600 |
| tgtggatatc ttgactgatt tttccatgga gggcacagtt aagccgctaa aggcattatc | 660 |
| cgccaagtac aattttttac tcttcgaaga cagaaaattt gctgacattg gtaatacagt | 720 |
| caaattgcag tactctgcgg gtgtatacag aatagcagaa tgggcagaca ttacgaatgc | 780 |
| acacggtgtg gtgggcccag gtattgttag cggtttgaag caggcggcag aagaagtaac | 840 |
| aaaggaacct agaggccttt tgatgttagc agaattgtca tgcaagggct ccctatctac | 900 |
| tggagaatat actaagggta ctgttgacat tgcgaagagc gacaaagatt ttgttatcgg | 960 |
| ctttattgct caaagagaca tgggtggaag agatgaaggt tacgattggt tgattatgac | 1020 |
| acccggtgtg ggtttagatg acaagggaga cgcattgggt caacagtata gaaccgtgga | 1080 |
| tgatgtggtc tctacaggat ctgacattat tattgttgga agaggactat ttgcaaaggg | 1140 |
| aagggatgct aaggtagagg gtgaacgtta cagaaaagca ggctgggaag catatttgag | 1200 |
| aagatgcggc cagcaaaact aaaaaactgt attataagta aatgcatgta tactaaactc | 1260 |
| acaaattaga gcttcaattt aattatatca gttattaccc tatgcggtgt gaaataccgc | 1320 |
| acagatgcgt aaggagaaaa taccgcatca gga | 1353 |

<210> SEQ ID NO 9
<211> LENGTH: 2474
<212> TYPE: DNA
<213> ORGANISM: Saccharomyces cerevisiae

<400> SEQUENCE: 9

| | |
|---|---:|
| tcctgatgcg gtattttctc cttacgcatc tgtgcggtat ttcacaccgc atatcgacgg | 60 |
| tcgaggagaa cttctagtat atccacatac ctaatattat tgccttatta aaatgaatt | 120 |
| cccaacaatt acatcaaaat ccacattctc ttcaaaatca attgtcctgt acttccttgt | 180 |
| tcatgtgtgt tcaaaaacgt tatatttata ggataattat actctatttc tcaacaagta | 240 |
| attggttgtt tggccgagcg gtctaaggcg cctgattcaa gaaatatctt gaccgcagtt | 300 |
| aactgtggga atactcaggt atcgtaagat gcaagagttc gaatctctta gcaaccatta | 360 |
| ttttttttcct caacataacg agaacacaca ggggcgctat cgcacagaat caaattcgat | 420 |
| gactggaaat ttttgttaa tttcagaggt cgcctgacgc atataccttt ttcaactgaa | 480 |
| aaattgggag aaaaaggaaa ggtgagaggc cggaaccggc ttttcatata gaatagagaa | 540 |
| gcgttcatga ctaaatgctt gcatcacaat acttgaagtt gacaatatta tttaaggacc | 600 |
| tattgttttt tccaataggt ggttagcaat cgtcttactt tctaactttt cttacctttt | 660 |
| acatttcagc aatatatata tatatttcaa ggatataccca ttctaatgtc tgcccctatg | 720 |
| tctgccccta agaagatcgt cgttttgcca ggtgaccacg ttggtcaaga atcacagcc | 780 |
| gaagccatta aggttcttaa agctattttct gatgttcgtt ccaatgtcaa gttcgatttc | 840 |
| gaaaatcatt taattggtgg tgctgctatc gatgctacag gtgtcccact tccagatgag | 900 |

| | |
|---|---|
| gcgctggaag cctccaagaa ggttgatgcc gttttgttag gtgctgtggg tggtcctaaa | 960 |
| tggggtaccg gtagtgttag acctgaacaa ggtttactaa aaatccgtaa agaacttcaa | 1020 |
| ttgtacgcca acttaagacc atgtaacttt gcatccgact ctcttttaga cttatctcca | 1080 |
| atcaagccac aatttgctaa aggtactgac ttcgttgttg tcagagaatt agtgggaggt | 1140 |
| atttactttg gtaagagaaa ggaagacgat ggtgatggtg tcgcttggga tagtgaacaa | 1200 |
| tacaccgttc cagaagtgca aagaatcaca agaatggccg cttttcatgg cctacaacat | 1260 |
| gagccaccat tgcctatttg gtccttggat aaagctaatg ttttggcctc ttcaagatta | 1320 |
| tggagaaaaa ctgtggagga aaccatcaag aacgaattcc ctacattgaa ggttcaacat | 1380 |
| caattgattg attctgccgc catgatccta gttaagaacc caacccacct aaatggtatt | 1440 |
| ataatcacca gcaacatgtt tggtgatatc atctccgatg aagcctccgt tatcccaggt | 1500 |
| tccttgggtt tgttgccatc tgcgtccttg gcctctttgc cagacaagaa caccgcattt | 1560 |
| ggtttgtacg aaccatgcca cggttctgct ccagatttgc caagaataaa ggttgaccct | 1620 |
| atcgccacta tcttgtctgc tgcaatgatg ttgaaattgt cattgaactt gcctgaagaa | 1680 |
| ggtaaggcca ttgaagatgc agttaaaaag gttttggatg caggtatcag aactggtgat | 1740 |
| ttaggtggtt ccaacagtac caccgaagtc ggtgatgctg tcgccgaaga agttaagaaa | 1800 |
| atccttgctt aaaaagattc tcttttttta tgatatttgt acataaactt tataaatgaa | 1860 |
| attcataata gaaacgacac gaaattacaa aatggaatat gttcataggg tagacgaaac | 1920 |
| tatatacgca atctcatatac atttatcaag aaggagaaaa aggaggatag taaaggaata | 1980 |
| caggtaagca aattgatact aatggctcaa cgtgataagg aaaagaatt gcactttaac | 2040 |
| attaatattg acaaggagga gggcaccaca caaaaagtta ggtgtaacag aaaatcatga | 2100 |
| aactacgatt cctaatttga tattggagga ttttctctaa aaaaaaaaaa atacaacaaa | 2160 |
| taaaaaacac tcaatgacct gaccattga tggagtttaa gtcaatacct tcttgaacca | 2220 |
| tttcccataa tggtgaaagt tccctcaaga attttactct gtcagaaacg gccttacgac | 2280 |
| gtagtcgata tggtgcactc tcagtacaat ctgctctgat gccgcatagt taagccagcc | 2340 |
| ccgacacccg ccaacacccg ctgacgcgcc ctgacgggct tgtctgctcc cggcatccgc | 2400 |
| ttacagacaa gctgtgaccg tctccgggag ctgcatgtgt cagaggtttt caccgtcatc | 2460 |
| accgaaacgc gcga | 2474 |

<210> SEQ ID NO 10
<211> LENGTH: 1177
<212> TYPE: DNA
<213> ORGANISM: Saccharomyces cerevisiae

<400> SEQUENCE: 10

| | |
|---|---|
| aattcccgtt ttaagagctt ggtgagcgct aggagtcact gccaggtatc gtttgaacac | 60 |
| ggcattagtc agggaagtca taacacagtc ctttcccgca attttctttt tctattactc | 120 |
| ttggcctcct ctagtacact ctatattttt ttatgcctcg gtaatgattt tcattttttt | 180 |
| ttttccccta gcggatgact cttttttttt cttagcgatt ggcattatca cataatgaat | 240 |
| tatacattat ataaagtaat gtgatttctt cgaagaatat actaaaaaat gagcaggcaa | 300 |
| gataaacgaa ggcaaagatg acagagcaga aagccctagt aaagcgtatt acaaatgaaa | 360 |
| ccaagattca gattgcgatc tctttaaagg gtggtcccct agcgatagag cactcgatct | 420 |
| tcccagaaaa agaggcagaa gcagtagcag aacaggccac acaatcgcaa gtgattaacg | 480 |
| tccacacagg tatagggttt ctggaccata tgatacatgc tctggccaag cattccggct | 540 |

```
ggtcgctaat cgttgagtgc attggtgact tacacataga cgaccatcac accactgaag    600
actgcgggat tgctctcggt caagcttta aagaggccct actggcgcgt ggagtaaaaa    660
ggtttggatc aggatttgcg cctttggatg aggcactttc cagagcggtg gtagatcttt    720
cgaacaggcc gtacgcagtt gtcgaacttg gtttgcaaag ggagaaagta ggagatctct    780
cttgcgagat gatcccgcat tttcttgaaa gctttgcaga ggctagcaga attaccctcc    840
acgttgattg tctgcgaggc aagaatgatc atcaccgtag tgagagtgcg ttcaaggctc    900
ttgcggttgc cataagagaa gccacctcgc ccaatggtac caacgatgtt ccctccacca    960
aaggtgttct tatgtagtga caccgattat ttaaagctgc agcatacgat atatatacat   1020
gtgtatatat gtatacctat gaatgtcagt aagtatgtat acgaacagta tgatactgaa   1080
gatgacaagg taatgcatca ttctatacgt gtcattctga acgaggcgcg ctttcctttt   1140 ttcttttgc ttttctttt tttttctctt gaactcg                              1177

<210> SEQ ID NO 11
<211> LENGTH: 3008
<212> TYPE: DNA
<213> ORGANISM: Saccharomyces cerevisiae

<400> SEQUENCE: 11
tgggcaattt catgtttctt caacactaca tatgcgtata tataccaatc taagtctgtg     60
ctccttcctt cgttcttcct tctgttcgga gattaccgaa tcaaaaaaat ttcaaggaaa    120
ccgaaatcaa aaaaagaat aaaaaaaaaa tgatgaattg aaaccccccc cccccccccc    180
gatgcgccgc gtgcggctgc tggagatggc ggacgcgatg gatatgttct gccaagggtt    240
gggtcgacgc taccttaaga gagacgcgtg cggccgcaag cttgcatgcc tgcaggtcga    300
tcgactctag aaatcgatag atctgaatta attcttgaat aatacataac ttttcttaaa    360
agaatcaaag acagataaaa tttaagagat attaaatatt agtgagaagc cgagaatttt    420
gtaacaccaa cataacactg acatctttaa caactttaa ttatgataca tttcttacgt     480
catgattgat tattacagct atgctgacaa atgactcttg ttgcatggct acgaaccggg    540
taatactaag tgattgactc ttgctgacct tttattaaga actaaatgga caatattatg    600
gagcatttca tgtataaatt ggtgcgtaaa atcgttggat ctctcttcta agtacatcct    660
actataacaa tcaagaaaaa caagaaaatc ggacaaaaca atcaagtatg gattctagaa    720
cagttggtat attaggaggg ggacaattgg gacgtatgat tgttgaggca gcaaacaggc    780
tcaacattaa gacggtaata ctagatgctg aaaattctcc tgccaaacaa ataagcaact    840
ccaatgacca cgttaatggc tccttttcca atcctcttga tatcgaaaaa ctagctgaaa    900
aatgtgatgt gctaacgatt gagattgagc atgttgatgt tcctacacta aagaatcttc    960
aagtaaaaca tcccaaatta aaaatttacc cttctccaga acaatcaga ttgatacaag   1020 acaaatatat tcaaaaagag catttaatca aaaatggtat agcagttacc caaagtgttc   1080
ctgtggaaca agccagtgag acgtccctat gaatgttgg aagagatttg gttttccat    1140 tcgtcttgaa gtcgaggact ttggcatacg atggaagagg taacttcgtt gtaaagaata   1200
aggaaatgat tccggaagct ttggaagtac tgaaggatcg tccttttgtac gccgaaaaat   1260 gggcaccatt tactaaagaa ttagcagtca tgattgtgag gtctgttaac ggtttagtgt   1320
tttcttaccc aattgtagag actatccaca aggacaatat ttgtgactta tgttatgcgc   1380
ctgctagagt tccggactcc gttcaactta aggcgaagtt gttggcagaa aatgcaatca   1440
aatcttttcc cggttgtggt atatttggtg tggaaatgtt ctatttagaa acaggggaat   1500
```

| | |
|---|---:|
| tgcttattaa cgaaattgcc ccaaggcctc acaactctgg acattatacc attgatgctt | 1560 |
| gcgtcacttc tcaatttgaa gctcatttga gatcaatatt ggatttgcca atgccaaaga | 1620 |
| atttcacatc tttctccacc attacaacga acgccattat gctaaatgtt cttggagaca | 1680 |
| aacatacaaa agataaagag ctagaaactt gcgaaagagc attggcgact ccaggttcct | 1740 |
| cagtgtactt atatggaaaa gagtctagac ctaacagaaa agtaggtcac ataaatatta | 1800 |
| ttgcctccag tatggcggaa tgtgaacaaa ggctgaacta cattacaggt agaactgata | 1860 |
| ttccaatcaa aatctctgtc gctcaaaagt tggacttgga agcaatggtc aaaccattgg | 1920 |
| ttggaatcat catgggatca gactctgact tgccggtaat gtctgccgca tgtgcggttt | 1980 |
| taaaagattt tggcgttcca tttgaagtga caatagtctc tgctcataga actccacata | 2040 |
| ggatgtcagc atatgctatt tccgcaagca agcgtgaaat taaaacaatt atcgctggag | 2100 |
| ctggtggggc tgctcacttg ccaggtatgg tggctgcaat gacaccactt cctgtcatcg | 2160 |
| gtgtgcccgt aaaaggttct tgtctagatg gagtagattc tttacattca attgtgcaaa | 2220 |
| tgcctagagg tgttccagta gctaccgtcg ctattaataa tagtacgaac gctgcgctgt | 2280 |
| tggctgtcag actgcttggc gcttatgatt caagttatac aacgaaaatg gaacagtttt | 2340 |
| tattaaagca agaagaagaa gttcttgtca aagcacaaaa gttagaaact gtcggttacg | 2400 |
| aagcttatct agaaaacaag taatatataa gtttattgat atacttgtac agcaaataat | 2460 |
| tataaaatga tatacctatt ttttaggctt tgttatgatt acatcaaatg tggacttcat | 2520 |
| acatagaaat caacgcttac aggtgtcctt ttttaagaat ttcatacata agatctctcg | 2580 |
| aggatccccg ggtaccgagc tcgaattcgc ggccgcccgc gggttaaccc tagggcatgc | 2640 |
| actagtggcc taattggccg acgtcaggtg gcacttttcg gggaaatgtg cgcggaaccc | 2700 |
| ctatttgttt attttttctaa atacattcaa atatgtatcc gctcatgaga caataaccct | 2760 |
| gataaatgct tcaataatat tgaaaaagga agagtatgag tattcaacat ttccgtgtcg | 2820 |
| cccttattcc cttttttgcg gcattttgcc ttcctgtttt tgctcaccca gaaacgctgg | 2880 |
| tgaaagtaaa agatgctgaa gatcagttgg gtgcacgagt gggttacatc gaactggatc | 2940 |
| tcaacagcgg taagatcctt gagagttttc gccccgaaga acgttttcca atgatgagca | 3000 |
| cttttaaa | 3008 |

<210> SEQ ID NO 12
<211> LENGTH: 4879
<212> TYPE: DNA
<213> ORGANISM: Saccharomyces cerevisiae

<400> SEQUENCE: 12

| | |
|---|---:|
| agcagttgct ttctcctatg ggaagagctt tctaagtctg aagaagtaaa cagttctttg | 60 |
| ctatttcaca cttcctggtt gatggtcact tgctgcctga aatatatata tatgtatgac | 120 |
| atatgtactt gttttctttt ttgtgccttt gttacgtcta tattcattga aactgattat | 180 |
| tcgattttct tcttgctgac cgcttctaga ggcatcgcac agttttagcg aggaaaactc | 240 |
| ttcaatagtt ttgccagcgg aattccactt gcaattacat aaaaaattcc ggcggttttt | 300 |
| cgcgtgtgac tcaatgtcga aatacctgcc taatgaacat gaacatcgcc caaatgtatt | 360 |
| tgaagacccg ctgggagaag ttcaagatat ataagtaaca agcagccaat agtataaaaa | 420 |
| aaaatctgag tttattacct ttcctggaat ttcagtgaaa aactgctaat tatagagaga | 480 |
| tatcacagag ttactcacta atgactaacg aaaaggtctg gatagagaag ttggataatc | 540 |
| caactctttc agtgttacca catgactttt tacgcccaca acaagaacct tatacgaaac | 600 |

-continued

```
aagctacata ttcgttacag ctacctcagc tcgatgtgcc tcatgatagt ttttctaaca    660
aatacgctgt cgctttgagt gtatgggctg cattgatata tagagtaacc ggtgacgatg    720
atattgttct ttatattgcg aataacaaaa tcttaagatt caatattcaa ccaacgtggt    780
catttaatga gctgtattct acaattaaca atgagttgaa caagctcaat tctattgagg    840
ccaattttc ctttgacgag ctagctgaaa aaattcaaag ttgccaagat ctggaaagga     900
cccctcagtt gttccgtttg gccttttgg aaaaccaaga tttcaaatta gacgagttca     960
agcatcattt agtggacttt gctttgaatt tggataccag taataatgcg catgttttga   1020
acttaattta taacagctta ctgtattcga atgaaagagt aaccattgtt gcggaccaat   1080
ttactcaata tttgactgct gcgctaagcg atccatccaa ttgcataact aaaatctctc   1140
tgatcaccgc atcatccaag gatagtttac ctgatccaac taagaacttg gctggtgcg    1200
atttcgtggg gtgtattcac gacatttcc aggacaatgc tgaagccttc ccagagagaa    1260
cctgtgttgt ggagactcca acactaaatt ccgacaagtc ccgttctttc acttatcgcg   1320
acatcaaccg cacttctaac atagttgccc attatttgat taaaacaggt atcaaaagag   1380
gtgatgtagt gatgatctat tcttctaggg gtgtggattt gatggtatgt gtgatgggtg   1440
tcttgaaagc cggcgcaacc ttttcagtta tcgaccctgc atatccccca gccagacaaa   1500
ccatttactt aggtgttgct aaaccacgtg ggttgattgt tattagagct gctgacaat    1560
tggatcaact agtagaagat tacatcaatg atgaattgga gattgtttca agaatcaatt   1620
ccatcgctat tcaagaaaat ggtaccattg aaggtggcaa attggacaat ggcgaggatg   1680
ttttggctcc atatgatcac tacaaagaca ccagaacagg tgttgtagtt ggaccagatt   1740
ccaacccaac cctatctttc acatctggtt ccgaaggtat tcctaagggt gttcttggta   1800
gacattttc cttggcttat tatttcaatt ggatgtccaa aaggttcaac ttaacagaaa    1860
atgataaatt cacaatgctg agcggtattg cacatgatcc aattcaaaga gatatgttta   1920
caccattatt tttaggtgcc caattgtatg tccctactca agatgatatt ggtacaccgg   1980
gccgtttagc ggaatggatg agtaagtatg gttgcacagt tacccattta acacctgcca   2040
tgggtcaatt acttactgcc caagctacta caccattccc taagttacat catgcgttct   2100
ttgtgggtga cattttaaca aaacgtgatt gtctgaggtt acaaaccttg gcagaaaatt   2160
gccgtattgt taatatgtac ggtaccactg aaacacagcg tgcagtttct tatttcgaag   2220
ttaaatcaaa aaatgacgat ccaaactttt tgaaaaaatt gaaagatgtc atgcctgctg   2280
gtaaaggtat gttgaacgtt cagctactag ttgttaacag gaacgatcgt actcaaatat   2340
gtggtattgg cgaaataggt gagatttatg ttcgtgcagg tggtttggcc gaaggttata   2400
gaggattacc agaattgaat aaagaaaaat ttgtgaacaa ctggtttgtt gaaaaagatc   2460
actggaatta tttggataag gataatggtg aaccttggag acaattctgg ttaggtccaa   2520
gagatagatt gtacagaacg ggtgatttag gtcgttatct accaaacggt gactgtgaat   2580
gttgcggtag ggctgatgat caagttaaaa ttcgtgggtt cagaatcgaa ttaggagaaa   2640
tagatacgca catttcccaa catccattgg taagagaaaa cattacttta gttcgcaaaa   2700
atgccgacaa tgagccaaca ttgatcacat ttatggtccc aagatttgac aagccagatg   2760
acttgtctaa gttccaaagt gatgttccaa aggaggttga aactgaccct atagttaagg   2820
gcttaatcgg ttaccatctt ttatccaagg acatcaggac tttcttaaag aaaagattgg   2880
ctagctatgc tatgccttcc ttgattgtgg ttatggataa actaccattg aatccaaatg   2940
gtaaagttga taagcctaaa cttcaattcc caactcccaa gcaattaaat ttggtagctg   3000
```

```
aaaatacagt ttctgaaact gacgactctc agtttaccaa tgttgagcgc gaggttagag    3060
acttatggtt aagtatatta cctaccaagc cagcatctgt atcaccagat gattcgtttt    3120
tcgatttagg tggtcattct atcttggcta ccaaaatgat tttaccttaa agaaaaagc    3180 tgcaagttga tttaccattg gcacaatttt caagtatcc aacgataaag cctttgccg     3240 cggaaattga cagaattaaa tcatcgggtg gatcatctca aggtgaggtc gtcgaaaatg    3300
tcactgcaaa ttatgcggaa gacgccaaga aattggttga gacgctacca agttcgtacc    3360
cctctcgaga atattttgtt gaacctaata gtgccgaagg aaaaacaaca attaatgtgt    3420
ttgttaccgg tgtcacagga tttctgggct cctacatcct tgcagatttg ttaggacgtt    3480
ctccaaagaa ctacagtttc aaagtgtttg cccacgtcag ggccaaggat gaagaagctg    3540
catttgcaag attacaaaag gcaggtatca cctatggtac ttggaacgaa aaatttgcct    3600
caaatattaa agttgtatta ggcgatttat ctaaaagcca atttggtctt tcagatgaga    3660
agtggatgga tttggcaaac acagttgata taattatcca taatggtgcg ttagttcact    3720
gggtttatcc atatgccaaa ttgagggatc caaatgttat ttcaactatc aatgttatga    3780
gcttagccgc cgtcggcaag ccaaagttct ttgactttgt ttcctccact tctactcttg    3840
acactgaata ctactttaat ttgtcagata aacttgttag cgaagggaag ccaggcattt    3900
tagaatcaga cgatttaatg aactctgcaa gcgggctcac tggtggatat ggtcagtcca    3960
aatgggctgc tgagtacatc attagacgtg caggtgaaag gggcctacgt gggtgtattg    4020
tcagaccagg ttacgtaaca ggtgcctctg ccaatggttc ttcaaacaca gatgatttct    4080
tattgagatt tttgaaaggt tcagtccaat taggtaagat tccagatatc gaaaattccg    4140
tgaatatggt tccagtagat catgttgctc gtgttgttgt tgctacgtct ttgaatcctc    4200
ccaaagaaaa tgaattggcc gttgctcaag taacgggtca cccaagaata ttattcaaag    4260
actacttgta tactttacac gattatggtt acgatgtcga aatcgaaagc tattctaaat    4320
ggaagaaatc attggaggcg tctgttattg acaggaatga agaaaatgcg ttgtatcctt    4380
tgctacacat ggtcttagac aacttacctg aaagtaccaa agctccggaa ctagacgata    4440
ggaacgccgt ggcatcttta aagaaagaca ccgcatggac aggtgttgat tggtctaatg    4500
gaataggtgt tactccagaa gaggttggta tatatattgc attttttaaac aaggttggat    4560 ttttaccctcc accaactcat aatgacaaac ttccactgcc aagtatagaa ctaactcaag    4620
cgcaaataag tctagttgct tcaggtgctg gtgctcgtgg aagctccgca gcagcttaag    4680
gttgagcatt acgtatgata tgtccatgta caataattaa atatgaatta ggagaaagac    4740
ttagcttctt ttcgggtgat gtcacttaaa aactccgaga ataatatata ataagagaat    4800
aaaatattag ttattgaata agaactgtaa atcagctggc gttagtctgc taatggcagc    4860
ttcatcttgg tttattgta                                                4879

<210> SEQ ID NO 13
<211> LENGTH: 1475
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
ttaggtctag agatctgttt agcttgcctc gtccccgccg ggtcacccgg ccagcgacat      60
ggaggcccag aataccctcc ttgacagtct tgacgtgcgc agctcagggg catgatgtga     120
ctgtcgcccg tacatttagc ccatacatcc ccatgtataa tcatttgcat ccatacattt     180
```

```
tgatggccgc acggcgcgaa gcaaaaatta cggctcctcg ctgcagacct gcgagcaggg      240
aaacgctccc ctcacagacg cgttgaattg tccccacgcc gcgccctgt agagaaatat       300 aaaaggttag gatttgccac tgaggttctt ctttcatata cttccttta aaatcttgct       360 aggatacagt tctcacatca catccgaaca taaacaacca tgggtaagga aaagactcac      420
gtttcgaggc cgcgattaaa ttccaacatg gatgctgatt tatatgggta taaatgggct     480
cgcgataatg tcgggcaatc aggtgcgaca atctatcgat tgtatgggaa gcccgatgcg     540
ccagagttgt ttctgaaaca tggcaaaggt agcgttgcca atgatgttac agatgagatg     600
gtcagactaa actggctgac ggaatttatg cctcttccga ccatcaagca ttttatccgt     660
actcctgatg atgcatggtt actcaccact gcgatccccg gcaaaacagc attccaggta     720
ttagaagaat atcctgattc aggtgaaaat attgttgatg cgctggcagt gttcctgcgc     780
cggttgcatt cgattcctgt ttgtaattgt ccttttaaca gcgatcgcgt atttcgtctc    840
gctcaggcgc aatcacgaat gaataacggt ttggttgatg cgagtgattt tgatgacgag    900
cgtaatggct ggcctgttga acaagtctgg aaagaaatgc ataagctttt gccattctca    960
ccggattcag tcgtcactca tggtgatttc tcacttgata accttatttt tgacgagggg  1020
aaattaatag gttgtattga tgttggacga gtcggaatcg cagaccgata ccaggatctt   1080
gccatcctat ggaactgcct cggtgagttt ctccttcat acagaaacg gcttttcaa     1140 aaatatggta ttgataatcc tgatatgaat aaattgcagt tcatttgat gctcgatgag     1200 tttttctaat cagtactgac aataaaaaga ttccttgtttt caagaacttg tcatttgtat   1260
agttttttta tattgtagtt gttctatttt aatcaaatgt tagcgtgatt tatatttttt    1320
ttcgcctcga catcatctgc ccagatgcga agttaagtgc gcagaaagta atatcatgcg   1380
tcaatcgtat gtgaatgctg gtcgctatac tgctgtcgat tcgatactaa cgccgccatc   1440
cagtgtcgaa aacgagctct cgagaaccct taata                              1475
```

<210> SEQ ID NO 14
<211> LENGTH: 931
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
ttcaaatatg tatccgctca tgagacaata accctgataa atgcttcaat aatattgaaa       60
aaggaagagt atgagtattc aacatttccg tgtcgccctt attccctttt ttgcggcatt     120
ttgccttcct gtttttgctc acccagaaac gctggtgaaa gtaaagatg ctgaagatca      180 gttgggtgca cgagtgggtt acatcgaact ggatctcaac agcggtaaga tccttgagag    240
ttttcgcccc gaagaacgtt ttccaatgat gagcactttt aaagttctgc tatgtggcgc    300
ggtattatcc cgtattgacg ccgggcaaga gcaactcggt cgccgcatac actattctca   360
gaatgacttg gttgagtact caccagtcac agaaaagcat cttacggatg gcatgacagt   420
aagagaatta tgcagtgctg ccataaccat gagtgataac actgcggcca acttacttct   480
gacaacgatc ggaggaccga aggagctaac cgcttttttg cacaacatgg ggatcatgt    540 aactcgcctt gatcgttggg aaccggagct gaatgaagcc ataccaaacg acgagcgtga    600
caccacgatg cctgcagcaa tggcaacaac gttgcgcaaa ctattaactg gcgaactact    660
tactctagct tcccggcaac aattaataga ctggatggag gcggataaag ttgcaggacc    720
```

```
acttctgcgc tcggcccttc cggctggctg gtttattgct gataaatctg gagccggtga      780
gcgtgggtct cgcggtatca ttgcagcact ggggccagat ggtaagccct cccgtatcgt      840
agttatctac acgacgggga gtcaggcaac tatggatgaa cgaaatagac agatcgctga      900
gataggtgcc tcactgatta agcattggta a                                     931
```

<210> SEQ ID NO 15
<211> LENGTH: 1382
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
ttctcatgtt tgacagctta tcatcgataa gctttaatgc ggtagtttat cacagttaaa       60
ttgctaacgc agtcaggcac cgtgtatgaa atctaacaat gcgctcatcg tcatcctcgg      120
caccgtcacc ctggatgctg taggcatagg cttggttatg ccggtactgc cgggcctctt      180
gcgggatatc gtccattccg acagcatcgc cagtcactat ggcgtgctgc tagcgctata      240
tgcgttgatg caatttctat gcgcacccgt tctcggagca ctgtccgacc gctttggccg      300
ccgcccagtc ctgctcgctt cgctacttgg agccactatc gactacgcga tcatggcgac      360
cacacccgtc ctgtggatcc tctacgccgg acgcatcgtg gccggcatca ccggcgccac      420
aggtgcggtt gctggcgcct atatcgccga catcaccgat ggggaagatc gggctcgcca      480
cttcgggctc atgagcgctt gtttcggcgt gggtatggtg caggccccg tggcgggggg      540 actgttgggc gccatctcct tgcatgcacc attccttgcg gcggcggtgc tcaacggcct      600
caacctacta ctgggctgct tcctaatgca ggagtcgcat aagggagagc gtcgaccgat      660
gcccttgaga gccttcaacc cagtcagctc cttccggtgg gcgcggggca tgactatcgt      720
cgccgcactt atgactgtct tctttatcat gcaactcgta ggacaggtgc cggcagcgct      780
ctgggtcatt ttcggcgagg accgctttcg ctggagcgcg acgatgatcg gcctgtcgct      840
tgcggtattc ggaatcttgc acgccctcgc tcaagccttc gtcactggtc cgccaccaa      900 acgtttcggc gagaagcagg ccattatcgc cggcatggcg gccgacgcgc tgggctacgt      960
cttgctggcg ttcgcgacgc gaggctggat ggccttcccc attatgattc ttctcgcttc     1020
cggcggcatc gggatgcccg cgttgcaggc catgctgtcc aggcaggtag atgacgacca     1080
tcagggacag cttcaaggat cgctcgcggc tcttaccagc ctaacttcga tcattggacc     1140
gctgatcgtc acggcgattt atgccgcctc ggcgagcaca tggaacgggt tggcatggat     1200
tgtaggcgcc gccctatacc ttgtctgcct ccccgcgttg cgtcgcggtg catggagccg     1260
ggccacctcg acctgaatgg aagccggcgg cacctcgcta acggattcac cactccaaga     1320
attggagcca atcaattctt gcggagaact gtgaatgcgc aaaccaaccc ttggcagaac     1380
at                                                                   1382
```

<210> SEQ ID NO 16
<211> LENGTH: 679
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
cccaatggca tcgtaaagaa cattttgagg catttcagtc agttgctcaa tgtacctata       60
```

-continued

```
accagaccgt tcagctggat attacggcct ttttaaagac cgtaaagaaa aataagcaca    120
agttttatcc ggcctttatt cacattcttg cccgcctgat gaatgctcat ccggaattcc    180
gtatggcaat gaaagacggt gagctggtga tatgggatag tgttcaccct tgttacaccg    240
ttttccatga gcaaactgaa acgttttcat cgctctggag tgaataccac gacgatttcc    300
ggcagtttct acacatatat tcgcaagatg tggcgtgtta cggtgaaaac ctggcctatt    360
tccctaaagg gtttattgag aatatgtttt tcgtctcagc caatccctgg gtgagtttca    420
ccagttttga tttaaacgtg gccaatatgg acaacttctt cgcccccgtt ttcaccatgg    480
gcaaatatta tacgcaaggc gacaaggtgc tgatgccgct ggcgattcag gttcatcatg    540
ccgtttgtga tggcttccat gtcggcagaa tgcttaatga attacaacag tactgcgatg    600
agtggcaggg cggggcgtaa ttttttttaag gcagttattg gtgcccttaa acgcctggtt    660
gctacgcctg aataagtga                                                 679
```

<210> SEQ ID NO 17
<211> LENGTH: 875
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
ttgccgggtg acgcacaccg tggaaacgga tgaaggcacg aacccagttg acataagcct     60
gttcggttcg taaactgtaa tgcaagtagc gtatgcgctc acgcaactgg tccagaacct    120
tgaccgaacg cagcggtggt aacggcgcag tggcggtttt catggcttgt tatgactgtt    180
tttttgtaca gtctatgcct cgggcatcca agcagcaagc gcgttacgcc gtgggtcgat    240
gtttcatgtt atggagcagc aacgatgtta cgcagcagca acgatgttac gcagcagggc    300
agtcgcccta aaacaaagtt aggtggctca agtatgggca tcattcgcac atgtaggctc    360
ggccctgacc aagtcaaatc catgcgggct gctcttgatc ttttcggtag tgagttcgga    420
gacgtagcca cctactccca acatcagccg gactccgatt acctcgggaa cttgctccgt    480
agtaagacat tcatcgcgct tgctgccttc gaccaagaag cggttgttgg cgctctcgcg    540
gcttacgttc tgcccaggtt tgagcagccg cgtagtgaga tctatatcta tgatctcgca    600
gtctccggcg agcaccggag gcagggcatt gccaccgcgc tcatcaatct cctcaagcat    660
gaggccaacg cgcttggtgc ttatgtgatc tacgtgcaag cagattacgg tgacgatccc    720
gcagtggctc tctatacaaa gttgggcata cgggaagaag tgatgcactt tgatatcgac    780
ccaagtaccg ccacctaaca attcgttcaa gccgagatcg gcttccggc cgcggagttg    840 ttcggtaaat tgtcacaacg ccgcggccat cggca                               875
```

<210> SEQ ID NO 18
<211> LENGTH: 1582
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
actagtatga aattaaatgg atatttggta catttaattc cacaaaaatg tccaatactt     60
aaaatacaaa attaaaagta ttagttgtaa acttgactaa catttaaat tttaaatttt    120 ttcctaatta tatattttac ttgcaaaatt tataaaaatt ttatgcattt ttatatcata    180
```

-continued

| | |
|---|---|
| ataataaaac ctttattcat ggtttataat ataataattg tgatgactat gcacaaagca | 240 |
| gttctagtcc catatatata actatatata acccgtttaa agatttattt aaaaatatgt | 300 |
| gtgtaaaaaa tgcttatttt taatttatt ttatataagt tataatatta aatacacaat | 360 |
| gattaaaatt aaataataat aaatttaacg taacgatgag ttgttttttt attttggaga | 420 |
| tacacgcata tggtaccagt atctttcaca agtcttttag cagcatctcc accttcacgt | 480 |
| gcaagttgcc gtccagctgc tgaagtggaa tcagttgcag tagaaaaacg tcaaacaatt | 540 |
| caaccaggta caggttacaa taacggttac ttttattctt actggaatga tggacacggt | 600 |
| ggtgttacat atactaatgg acctggtggt caatttagtg taaattggag taactcaggc | 660 |
| aattttgttg gaggaaaagg ttggcaacct ggtacaaaga ataaggtaat caatttctct | 720 |
| ggtagttaca accctaatgg taattcttat ttaagtgtat acggttggag ccgtaaccca | 780 |
| ttaattgaat attatattgt agagaacttt ggtacataca acccttcaac aggtgctact | 840 |
| aaattaggtg aagttacttc agatggatca gtttatgata tttatcgtac tcaacgcgta | 900 |
| aatcaaccat ctataattgg aactgccact ttctaccaat actggagtgt aagacgtaat | 960 |
| catcgttcaa gtggtagtgt taatacagca aaccactttta atgcatgggc tcaacaaggt | 1020 |
| ttaacattag gtacaatgga ctatcaaatt gtagctgttg aaggttatt ttcatcaggt | 1080 |
| agtgcttcta tcactgttag cggtaccggt gaaaacttat actttcaagg ctcaggtggc | 1140 |
| ggtggaagtg attacaaaga tgatgatgat aaaggaaccg ttaatctag acttagcttc | 1200 |
| aactaactct agctcaaaca actaattttt ttttaaacta aaataaatct ggttaaccat | 1260 |
| acctggttta tttagttta gtttatacac acttttcata tatatatact taatagctac | 1320 |
| cataggcagt tggcaggacg tccccttacg ggacaaatgt atttattgtt gcctgccaac | 1380 |
| tgcctaatat aaatattagt ggacgtcccc ttccccttac gggcaagtaa acttaggat | 1440 |
| tttaatgctc cgttaggagg caaataaatt ttagtggcag ttgcctcgcc tatcggctaa | 1500 |
| caagttcctt cggagtatat aaatatcctg ccaactgccg atatttatat actaggcagt | 1560 |
| ggcggtacca ctcgacacta gt | 1582 |

<210> SEQ ID NO 19
<211> LENGTH: 2017
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 19

| | |
|---|---|
| actagtatga aattaaatgg atatttggta catttaattc cacaaaaatg tccaatactt | 60 |
| aaaatacaaa attaaaagta ttagttgtaa acttgactaa catttaaat tttaaatttt | 120 |
| ttcctaatta tatatttac ttgcaaaatt tataaaaatt ttatgcattt ttatatcata | 180 |
| ataataaaac ctttattcat ggtttataat ataataattg tgatgactat gcacaaagca | 240 |
| gttctagtcc catatatata actatatata acccgtttaa agatttattt aaaaatatgt | 300 |
| gtgtaaaaaa tgcttatttt taatttatt ttatataagt tataatatta aatacacaat | 360 |
| gattaaaatt aaataataat aaatttaacg taacgatgag ttgttttttt attttggaga | 420 |
| tacacgcata tggtaccaca caagttcaca ggtgttaacg ctaaattcca gcaaccagca | 480 |
| ttaagaaatt tatctccagt ggtagttgag cgcgaacgtg aggaatttgt aggattcttt | 540 |
| ccacaaattg ttcgtgactt aactgaagat ggtattggtc atccagaagt aggtgacgct | 600 |
| gtagctcgtc ttaaagaagt attacaatac aacgcacctg gtggtaaatg caatagaggt | 660 |

```
ttaacagttg ttgcagctta ccgtgaactt tctggaccag gtcaaaaaga cgctgaaagt    720
cttcgttgtg ctttagcagt aggatggtgt attgaattat tccaagcctt tttcttagtt    780
gctgacgata taatggacca gtcattaact agacgtggtc aattatgttg gtacaagaaa    840
gaaggtgttg gtttagatgc aataaatgat tcttttcttt tagaaagctc tgtgtatcgc    900
gttcttaaaa agtattgccg tcaacgtcca tattatgtac atttattaga gcttttctt    960 caaacagctt accaaacaga attaggacaa atgttagatt taatcactgc tcctgtatct   1020
aaggtagatt taagccattt ctcagaagaa cgttacaaag ctattgttaa gtataaaact   1080
gctttctatt cattctattt accagttgca gcagctatgt atatggttgg tatagattct   1140
aaagaagaac atgaaaacgc aaaagctatt ttacttgaga tgggtgaata cttccaaatt   1200
caagatgatt atttagattg ttttggcgat cctgctttaa caggtaaagt aggtactgat   1260
attcaagata caaatgttc atggttagtt gtgcaatgct acaaagagt aacaccagaa    1320 caacgtcaac ttttagaaga taattacggt cgtaaagaac cagaaaagt tgctaaagtt   1380 aaagaattat atgaggctgt aggtatgaga gccgcctttc aacaatacga agaaagtagt   1440
taccgtcgtc ttcaagagtt aattgagaaa cattctaatc gtttaccaaa agaaattttc   1500
ttaggtttag ctcagaaaat atacaaacgt caaaaggta ccggtgaaaa cttatacttt    1560
caaggctcag gtggcggtgg aagtgattac aagatgatg atgataaagg aaccggttaa    1620
tctagactta gcttcaacta actctagctc aaacaactaa ttttttttta aactaaaata   1680
aatctggtta accatacctg gtttatttta gtttagttta tacacacttt tcatatatat   1740
atacttaata gctaccatag gcagttggca ggacgtcccc ttacgggaca aatgtattta   1800
ttgttgcctg ccaactgcct aatataaata ttagtggacg tccccttccc cttacgggca   1860
agtaaactta gggattttaa tgctccgtta ggaggcaaat aaattttagt ggcagttgcc   1920
tcgcctatcg gctaacaagt tccttcggag tatataaata tcctgccaac tgccgatatt   1980
tatatactag gcagtggcgg taccactcga cactagt                            2017
```

<210> SEQ ID NO 20
<211> LENGTH: 6521
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
tcgtgtagat aactacgata cgggagggct taccatctgg ccccagtgct gcaatgatac     60
cgcgagaccc acgctcaccg gctccagatt tatcagcaat aaaccagcca gccggaaggg    120
ccgagcgcag aagtggtcct gcaactttat ccgcctccat ccagtctatt aattgttgcc    180
gggaagctag agtaagtagt tcgccagtta atagtttgcg caacgttgtt gccattgcta    240
caggcatcgt ggtgtcacgc tcgtcgtttg gtatggcttc attcagctcc ggttcccaac    300
gatcaaggcg agtacatga tcccccatgt tgtgcaaaaa agcggttagc tccttcggtc     360
ctccgatcgt tgtcagaagt aagttggccg cagtgttatc actcatggtt atggcagcac    420
tgcataattc tcttactgtc atgccatccg taagatgctt ttctgtgact ggtgagtact    480
caaccaagtc attctgagaa tagtgtatgc ggcgaccgag ttgctcttgc ccggcgtcaa    540
tacgggataa taccgcgcca catagcagaa ctttaaaagt gctcatcatt ggaaaacgtt    600
cttcggggcg aaaactctca aggatcttac cgctgttgag atccagttcg atgtaaccca    660
```

```
ctcgtgcacc caactgatct tcagcatctt ttactttcac cagcgtttct gggtgagcaa    720
aaacaggaag gcaaaatgcc gcaaaaaagg gaataagggc gacacggaaa tgttgaatac    780
tcatactctt cctttttcaa tattattgaa gcatttatca gggttattgt ctcatgagcg    840
gatacatatt tgaatgtatt tagaaaaata aacaaatagg ggttccgcgc acatttcccc    900
gaaaagtgcc acctgacgtc taagaaacca ttattatcat gacattaacc tataaaaata    960
ggcgtatcac gaggcccttt cgtctcgcgc gtttcggtga tgacggtgaa aacctctgac   1020
acatgcagct cccggagacg gtcacagctt gtctgtaagc ggatgccggg agcagacaag   1080
cccgtcaggg cgcgtcagcg ggtgttggcg ggtgtcgggg ctggcttaac tatgcggcat   1140
cagagcagat tgtactgaga gtgcaccata ggcggccgcg gcgcgccgtt ccggatctgc   1200
atcctgcgat gcagatccgg aacataatgg tgcaggcgc tgacttccgc gtttccagac    1260
tttacgaaac acggaaaccg aagaccattc atgttgttgc tcaggtcgca gacgttttgc   1320
agcagcagtc gcttcacgtt cgctcgcgta tcggtgattc attctgctaa ccagtaaggc   1380
aaccccgcca gcctagccgg gtcctcaacg acaggagcac gatcatgcgc acccgtggcc   1440
aggacccaac gctgcccgag atgcgccgcg tgcggctgct ggagatggcg gacgcgatgg   1500
atatgttctg ccaagggttg gtttgcgcat tcacagttct ccgcaagaat tgattggctc   1560
caattcttgg agtggtgaat ccgttagcga ggtgccgccg gcttccattc aggtcgaggt   1620
ggcccggctc catgcaccgc gacgcaacgc ggggaggcag acaaggtata gggcggcgcc   1680
tacaatccat gccaacccgt tccatgtgct cgccgaggcg gcataaatcg ccgtgacgat   1740
cagcggtcca atgatcgaag ttaggctggt aagagccgcg agcgatcctt gaagctgtcc   1800
ctgatggtcg tcatctacct gcctggacag catggcctgc aacgcgggca tcccgatgcc   1860
gccggaagcg agaagaatca taatgggaa ggccatccag cctcgcgtcg cgaacgccag     1920
caagacgtag cccagcgcgt cggccgccat gccggcgata atggcctgct tctcgccgaa   1980
acgtttggtg gcgggaccag tgacgaaggc ttgagcgagg gcgtgcaaga ttccgaatac   2040
cgcaagcgac aggccgatca tcgtcgcgct ccagcgaaag cggtcctcgc cgaaaatgac   2100
ccagagcgct gccggcacct gtcctacgag ttgcatgata aagaagacag tcataagtgc   2160
ggcgacgata gtcatgcccc gcgcccaccg gaaggagctg actgggttga aggctctcaa   2220
gggcatcggt cgagcttgac attgtaggac gtttaaacat taccctgtta tccctaggat   2280
cctacgtata catactccga aggaggacaa atttatttat tgtggtacaa taaataagtg   2340
gtacaataaa taaattgtat gtaaacccct tccccttcgg gacgtcccct tacgggaata   2400
taaatattag tggcagttgc ctgccaacaa atttatttat tgtattaaca taggcagtgg   2460
cggtaccact gccactggcg tcctaatata aatattgggc aactaaagtt tatcgcagta   2520
ttaacatagg cagtggcggt accactgcca ctggcgtcct ccttcggagt atgtaaacct   2580
gctaccgcag caaataaatt ttattctatt ttaatactac aatatttaga ttcccgttag   2640
gggataggcc aggcaattgt cactggcgtc atagtatatc aatattgtaa cagattgaca   2700
ccctttaagt aaacattttt tttaggattc atatgaaatt aaatggatat ttggtacatt   2760
taattccaca aaaatgtcca atacttaaaa tacaaaatta aaagtattag ttgtaaactt   2820
gactaacatt ttaaattta aatttttcc taattatata ttttacttgc aaaatttata    2880 aaaatttat gcatttttat atcataataa taaaaccttt attcatggtt tataatataa    2940
taattgtgat gactatgcac aaagcagttc tagtcccata tatataacta tatataaccc   3000
gtttaaagat ttatttaaaa atatgtgtgt aaaaaatgct tattttaat tttatttat     3060
```

```
ataagttata atattaaata cacaatgatt aaaattaaat aataataaat ttaacgtaac    3120
gatgagttgt ttttttattt tggagataca cgcaatgaca attgcgatcg gtacatatca    3180
agagaaacgc acatggttcg atgacgctga tgactggctt cgtcaagacc gtttcgtatt    3240
cgtaggttgg tcaggtttat tactattccc ttgtgcttac tttgcaactc cggtccggcg    3300
gccgcctcga gacgcttacc agacaaggca gttttttcat tcttttaaag caggcagttc    3360
tgaagggaa aagggactgc ctactgcggt cctaggtaaa tacattttta tgcaatttat     3420
ttcttgtgct agtaggtttc tatactcaca agaagcaacc ccttgacgag agaacgttat    3480
cctcagagta tttataatcc tgagagggaa tgcactgaag aatatttttcc ttattttta    3540
cagaaagtaa ataaaatagc gctaataacg cttaattcat ttaatcaatt atggcaacag    3600
gaacttctaa agctaaacca tcaaaagtaa attcagactt ccaagaacct ggtttagtta    3660
caccattagg tactttatta cgtccactta actcagaagc aggtaaagta ttaccaggct    3720
ggggtacaac tgttttaatg gctgtattta tccttttatt tgcagcattc ttattaatca    3780
ttttagaaat ttacaacagt tctttaattt tagatgacgt ttctatgagt tgggaaactt    3840
tagctaaagt ttcttaattt tatttaacac aaacataaaa tataaaactg tttgttaagg    3900
ctagctgcta agtcttcttt tcgctaaggt aaactaagca actcaaccat atttatattc    3960
ggcagtggca ccgccactgc cactggcctt ccgttaagat aaacgcgtta atagctcact    4020
tttctttaaa tttaattttt aatttaaagg tgtaagcaaa ttgcctgacg agagatccac    4080
ttaaggatg acagtggcgg gctactgcct acttccctcc gggataaaat ttatttgaaa     4140
aacgttagtt acttcctaac ggagcattga catccccata tttatattag gacgtccct     4200
tcgtcgacat taccctgtta tccctaggcc ggcctaagaa accattatta tcatgacatt    4260
aacctataaa aataggcgta tcacgaggcc ctttcgtctt caagaaattc ggtcgaaaaa    4320
agaaaaggag agggccaaga gggagggcat tggtgactat tgagcacgtg agtatacgtg    4380
attaagcaca caaaggcagc ttggagtatg tctgttatta atttcacagg tagttctggt    4440
ccattggtga agtttgcgg cttgcagagc acagaggccg cagaatgtgc tctagattcc     4500
gatgctgact tgctgggtat tatatgtgtg cccaatagaa agaacaat tgacccggtt      4560
attgcaagga aaatttcaag tcttgtaaaa gcatataaaa atagttcagg cactccgaaa    4620
tacttggttg gcgtgtttcg taatcaacct aaggaggatg ttttggctct ggtcaatgat    4680
tacggcattg atatcgtcca actgcatgga gatgagtcgt ggcaagaata ccaagagttc    4740
ctcggtttgc cagttattaa aagactcgta tttccaaaag actgcaacat actactcagt    4800
gcagcttcac agaaacctca ttcgtttatt cccttgtttg attcagaagc aggtgggaca    4860
ggtgaacttt tggattggaa ctcgatttct gactgggttg gaaggcaaga gagccccgaa    4920
agcttacatt ttatgttagc tggtggactg acgccagaaa atgttggtga tgcgcttaga    4980
ttaaatggcg ttattggtgt tgatgtaagc ggaggtgtgg agacaaatgg tgtaaaagac    5040
tctaacaaaa tagcaaattt cgtcaaaaat gctaagaaat aggttattac tgagtagtat    5100
ttatttaagt attgtttgtg cacttgcctg caggcctttt gaaaagcaag cataaaagat    5160
ctaaacataa aatctgtaaa ataacaagat gtaaagataa tgctaaatca tttggctttt    5220
tgattgattg tacaggaaaa tatacatcgt taattaagcg gccgcgagct tggcgtaatc    5280
atggtcatag ctgtttcctg tgtgaaattg ttatccgctc acaattccac acaacatacg    5340
agccggaagc ataagtgta aagcctgggg tgcctaatga gtgagctaac tcacattaat    5400
tgcgttgcgc tcactgcccg ctttccagtc gggaaacctg tcgtgccagc tgcattaatg    5460
```

-continued

```
aatcggccaa cgcgcgggga gaggcggttt gcgtattggg cgctcttccg cttcctcgct    5520
cactgactcg ctgcgctcgg tcgttcggct gcggcgagcg gtatcagctc actcaaaggc    5580
ggtaatacgg ttatccacag aatcagggga taacgcagga agaacatgt gagcaaaagg     5640 ccagcaaaag gccaggaacc gtaaaaaggc cgcgttgctg gcgttttcc ataggctccg     5700 cccccctgac gagcatcaca aaaatcgacg ctcaagtcag aggtggcgaa acccgacagg    5760
actataaaga taccaggcgt ttccccctgg aagctccctc gtgcgctctc ctgttccgac    5820
cctgccgctt accggatacc tgtccgcctt tctcccttcg ggaagcgtgg cgctttctca    5880
tagctcacgc tgtaggtatc tcagttcggt gtaggtcgtt cgctccaagc tgggctgtgt    5940
gcacgaaccc cccgttcagc ccgaccgctg cgccttatcc ggtaactatc gtcttgagtc    6000
caacccggta agacacgact tatcgccact ggcagcagcc actggtaaca ggattagcag    6060
agcgaggtat gtaggcggtg ctacagagtt cttgaagtgg tggcctaact acggctacac    6120
tagaagaaca gtatttggta tctgcgctct gctgaagcca gttaccttcg gaaaaagagt    6180
tggtagctct tgatccggca aacaaaccac cgctggtagc ggtggttttt tgtttgcaa     6240 gcagcagatt acgcgcagaa aaaaaggatc tcaagaagat cctttgatct ttctacggg     6300 gtctgacgct cagtggaacg aaaactcacg ttaagggatt ttggtcatga gattatcaaa    6360
aaggatcttc acctagatcc ttttaaatta aaaatgaagt tttaaatcaa tctaaagtat    6420
atatgagtaa acttggtctg acagttacca atgcttaatc agtgaggcac ctatctcagc    6480
gatctgtcta tttcgttcat ccatagttgc ctgactcccc g                        6521
```

<210> SEQ ID NO 21
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
ttggttgcgg ccgcttaatt aacgatgtat attttcctgt acaatc                    46
```

<210> SEQ ID NO 22
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
gtttaaacat taccctgtta tccctaggcc ggcctaagaa accattatta tcatgaca      58
```

<210> SEQ ID NO 23
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
ggccggccta gggataacag ggtaatgttt aaacgtccta caatgtcaag ctcgaccg      58
```

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ttggttgcgg ccgcggcgcg ccgttccgga tctgcatcgc aggatg           46

<210> SEQ ID NO 25
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ttggtttagg gataacaggg taatgtcgac aacatgctaa gtttacttgc ccga       54

<210> SEQ ID NO 26
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
actccggtcc ggcggccgcc tcgagacgac ttgtccgctt catcagacac gg         52

<210> SEQ ID NO 27
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
cgtctcgagg cggccgccgg accggagttg caaagtaagc acaagggaat ag         52

<210> SEQ ID NO 28
<211> LENGTH: 59
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
tggttattac cctgttatcc ctaggatcct acgtatacat actccgaagg aggacaaat    59

<210> SEQ ID NO 29
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
cgtctcgagg cggccgccgg accggagtca tccgccccat ctaataaa              48

<210> SEQ ID NO 30
<211> LENGTH: 56
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ttggttatta ccctgttatc cctaggatcc tacgtacagt ggcggtacca caataa         56

<210> SEQ ID NO 31
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttggtttagg gataacaggg taatgtcgac gtatgtaaac cccttcgggc aac            53

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
actccggtcc ggcggccgcc tcgagacgcc gtaaacagat aggaatgacg                50

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgtctcgagg cggccgccgg accggagtga atccaggcat cttgggta                  48

<210> SEQ ID NO 34
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ttggttatta ccctgttatc cctaggatcc tacgtaggga aggtgcaac tacctg          56

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttggtttagg gataacaggg taatgtcgac aacatgcttg gcactggttt                50

<210> SEQ ID NO 36
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 36
actccggtcc ggcggccgcc tcgagacgtg gtaatttatt tggtaatttg gtca          54

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cgtctcgagg cggccgccgg accggagtaa ccaaccattg tgtgacca                 48

<210> SEQ ID NO 38
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttggttatta ccctgttatc cctaggatcc tacgtaagag tacgggatgt gggatg        56

<210> SEQ ID NO 39
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ttggtttagg gataacaggg taatgtcgac ccataagtaa actcccttttt gga           53

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
actccggtcc ggcggccgcc tcgagacgta aaattgtttg tgtggtctgg               50

<210> SEQ ID NO 41
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cgtctcgagg cggccgccgg accggagtaa atgtaacttt tgttgtcgat cc            52

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
```

```
ttggttatta ccctgttatc cctaggatcc tacgtagggt aaataaattt tagtggacgt       60
```

<210> SEQ ID NO 43
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
ttggtttagg gataacaggg taatgtcgac gaaggggacg tcctaatata aata       54
```

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

```
actccggtcc ggcggccgcc tcgagacgct taccagacaa ggcagttttt              50
```

<210> SEQ ID NO 45
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

```
cgtctcgagg cggccgccgg accggagtgc tgctggttat gcagttga                 48
```

<210> SEQ ID NO 46
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

```
ttggttatta ccctgttatc cctaggatcc tacgtagagg accaaatcct gcgtta       56
```

<210> SEQ ID NO 47
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

```
ttggtttagg gataacaggg taatgtcgac tttgcttgcc tacaagagca              50
```

<210> SEQ ID NO 48
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

```
actccggtcc ggcggccgcc tcgagacgtt gcattaaaat ccggaagg                 48
```

```
<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttggttcccg ggtcgcgcgt ttcggtgatg acggtg                            36

<210> SEQ ID NO 50
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttggttgtcg acccgcggtg atgcggtatt ttctccttac gc                     42

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ttggttcccg ggtcctgatg cggtattttc tcctta                            36

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttggttcccg ggtcgcgcgt ttcggtgatg acggtg                            36

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ttggttcccg ggaagcttgc atgcctgcag gtcgat                            36

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ttggttcccg ggagcagttg ctttctccta tgggaa                            36

<210> SEQ ID NO 55
```

```
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ttggttcccg ggttaggtct agagatctgt ttagct                              36

<210> SEQ ID NO 56
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ttggttgtcg acggccggcc actagttcgc gcgtttcggt gatgacggtg              50

<210> SEQ ID NO 57
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ttggttgtcg acggccggcc actagttgat gcggtatttt ctccttacgc              50

<210> SEQ ID NO 58
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ttggttgtcg acggccggcc actagtgatc ctcgagagat cttatgtatg              50

<210> SEQ ID NO 59
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ttggttgtcg acggccggcc actagttaca ataaaccaag atgaagctgc              50

<210> SEQ ID NO 60
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ttggttgtcg acggccggcc actagttatt aagggttctc gagagctcgt              50

<210> SEQ ID NO 61
<211> LENGTH: 39
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 61
ttggttcccg gggatatcaa tacattcaaa tatgtatcc    39

<210> SEQ ID NO 62
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
ttggttcccg gggatatcat cctttttaaat taaaaatgaa g    41

<210> SEQ ID NO 63
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
ttggttcccg gggatatctt ctcatgtttg acagcttatc at    42

<210> SEQ ID NO 64
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
aaccaacccg gggatatcat gttctgccaa gggttggttt gc    42

<210> SEQ ID NO 65
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
ttggttcccg gggatatccc caatccaggt cctgaccgtt ct    42

<210> SEQ ID NO 66
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
aaccaacccg gggatatctc acttattcag gcgtagcaac ca    42

<210> SEQ ID NO 67
<211> LENGTH: 42
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 67
ttggttcccg gggatatctt gccgggtgac gcacaccgtg ga                              42

<210> SEQ ID NO 68
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
aaccaacccg gggatatctg ccgatggccg cggcgttgtg ac                              42

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
catactactc agtgcagctt cac                                                   23

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gtgaaggagc atgttcggca cacag                                                 25

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ctgtgtgccg aacatgctcc ttcac                                                 25

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ttgtcatatt actagttggt gtgg                                                  24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 73
ggtcggcgac aactcaatcg acag                                          24

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
caacggatgt tttattgcct ttg                                           23

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gcaaggattt tcttaacttc ttcg                                          24

<210> SEQ ID NO 76
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
atgaagtcct tgttactgt gccgc                                          25

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
caggaattcg ctaaagcctg tgg                                           23

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gagaataaaa gtctaagatg tgcg                                          24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
```

```
gacatatatg aacatcgcgg agtg                                          24
```

```
<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cttcaatgca tcagcactac caac                                          24
```

```
<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ggtcagattg ccctgtcgtt ctc                                           23
```

```
<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cagtttcatt tgatgctcga tgag                                          24
```

```
<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ggtagaattg tccgttagtt gttta                                         25
```

```
<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
aacagacgta gtaagaacca ccagc                                         25
```

```
<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ctccagaagc gttaatgtct ggctt                                         25
```

```
<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cgaccatcag ggacagcttc aagg                                          24

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ggtctccaga acttgctgct                                               20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cctatcccct aacgggaatc                                               20

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
agattttgtg taatgccgaa gt                                            22

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tgccgtaatc attgaccaga                                               20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ggtgcgtaaa atcgttggat                                               20
```

```
<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tttttcggcg tacaaaggac                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ctcgcctatc ggctaacaag                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cacaagaagc aacccttga                                               20

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
aaatttaacg taacgatgag ttg                                          23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gcactacctg atgaaaaata acc                                          23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ggaaggggac gtaggtacat aaa                                          23
```

```
<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ttagaacgtg ttttgttccc aat                                            23

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cgttcttctg agaaatggct ta                                             22
```